(12) United States Patent
Mason et al.

(10) Patent No.: US 10,913,802 B2
(45) Date of Patent: Feb. 9, 2021

(54) MONOCLONAL ANTIBODY INHIBITOR OF FACTOR XIIA

(71) Applicant: Dyax Corp., Lexington, MA (US)

(72) Inventors: Shauna Mason, Arlington, MA (US);
Jon A. Kenniston, Hingham, MA (US);
Andrew Nixon, Hanover, MA (US);
Daniel J. Sexton, Melrose, MA (US);
Stephen R. Comeau, Avon, NY (US);
Burt Adelman, Concord, MA (US)

(73) Assignee: Dyax Corp., Lexington, MA (US)

( * ) Notice: Subject to any disclaimer, the term of this patent is extended or adjusted under 35 U.S.C. 154(b) by 168 days.

(21) Appl. No.: 15/746,048

(22) PCT Filed: Jul. 21, 2016

(86) PCT No.: PCT/US2016/043265
§ 371 (c)(1),
(2) Date: Jan. 19, 2018

(87) PCT Pub. No.: WO2017/015431
PCT Pub. Date: Jan. 26, 2017

(65) Prior Publication Data
US 2019/0002584 A1  Jan. 3, 2019

Related U.S. Application Data

(60) Provisional application No. 62/316,310, filed on Mar. 31, 2016, provisional application No. 62/273,657, filed on Dec. 31, 2015, provisional application No. 62/194,957, filed on Jul. 21, 2015.

(51) Int. Cl.
| | | |
|---|---|---|
| *C07K 16/36* | (2006.01) | |
| *A61K 39/00* | (2006.01) | |
| *A61P 7/02* | (2006.01) | |
| *A61P 9/00* | (2006.01) | |
| *A61P 11/00* | (2006.01) | |

(52) U.S. Cl.
CPC ........ *C07K 16/36* (2013.01); *A61K 2039/505* (2013.01); *C07K 2317/21* (2013.01); *C07K 2317/24* (2013.01); *C07K 2317/34* (2013.01); *C07K 2317/55* (2013.01); *C07K 2317/76* (2013.01); *C07K 2317/90* (2013.01); *C07K 2317/92* (2013.01); *C07K 2317/94* (2013.01)

(58) Field of Classification Search
CPC . A61K 2039/505; A61K 39/3955; A61P 7/02; A61P 9/00; A61P 11/00; C07K 2317/76; C07K 2317/24; C07K 2317/21; C07K 2317/94; C07K 2317/55; C07K 2317/90

See application file for complete search history.

(56) References Cited

U.S. PATENT DOCUMENTS

| | | |
|---|---|---|
| 4,963,657 A | 10/1990 | Pixley |
| 5,500,349 A | 3/1996 | Esnouf |
| 2008/0254039 A1 | 10/2008 | Nieswandt et al. |
| 2009/0304685 A1 | 12/2009 | Pritchard |
| 2011/0200611 A1 | 8/2011 | Sexton |
| 2011/0201017 A1 | 8/2011 | Greenfield et al. |
| 2012/0201756 A1 | 8/2012 | Sexton |
| 2014/0199361 A1 | 7/2014 | Panousis et al. |
| 2018/0118851 A1 | 3/2018 | Comeau et al. |

FOREIGN PATENT DOCUMENTS

| | | |
|---|---|---|
| CN | 102439036 A | 5/2012 |
| CN | 103635489 A | 3/2014 |
| CN | 103687878 A | 3/2014 |
| CN | 104011221 A | 8/2014 |
| JP | H04-503006 A | 6/1992 |
| JP | 2014-506257 A | 3/2014 |
| JP | 2014-523253 A | 9/2014 |
| JP | 2016-513682 A | 5/2016 |
| JP | 2016-525551 A | 8/2016 |
| JP | 2017-501968 A | 1/2017 |
| WO | WO 90/08835 A1 | 8/1990 |
| WO | WO 91/17258 A1 | 11/1991 |
| WO | WO 97/42507 A1 | 11/1997 |
| WO | WO 2012/094587 A1 | 7/2012 |
| WO | WO 2013/014092 A1 | 1/2013 |
| WO | WO 2013/014902 A1 | 1/2013 |
| WO | WO 2013/051294 A1 | 4/2013 |
| WO | WO 2014/019644 A1 | 2/2014 |
| WO | WO 2014/113701 A1 | 7/2014 |
| WO | WO 2014/152232 A2 | 9/2014 |
| WO | WO 2014/207199 A1 | 12/2014 |
| WO | WO 2015/013671 A1 | 1/2015 |

(Continued)

OTHER PUBLICATIONS

Bendig, M.M. Humanization of rodent monoclonal antibodies by CDR grafting. Methods: A Comparision to Methods in Enzymology, 1995, 8:83-93.*

(Continued)

*Primary Examiner* — Vanessa L. Ford
*Assistant Examiner* — Bruce D. Hissong
(74) *Attorney, Agent, or Firm* — Wolf, Greenfield & Sacks, P.C.

(57) ABSTRACT

Disclosed herein are anti-Factor XIIa antibodies and methods of using such for treating diseases associated with Factor XII, including diseases associated with contact system activation, plasma prekallikrein signaling (e.g., hereditary angioedema), and ocular diseases.

15 Claims, 33 Drawing Sheets
Specification includes a Sequence Listing.

(56) References Cited

FOREIGN PATENT DOCUMENTS

| WO | WO 2016/109774 A1 | 7/2016 |
|---|---|---|
| WO | WO 2017/015431 A1 | 1/2017 |

OTHER PUBLICATIONS

Casset, F.,et al. A peptide mimetic of an anti-CD4 monoclonal antibody by rational design. Biochem. Biophys. Res. Comm., 2003, 307:198-205.*

MacCallum, R.M., et al. Antibody-antigen interactions: Contact analysis and binding site topography. J. Mol. Biol., 1996, 262:732-745.*

Paul, W.E., Fundamental Immunology, 3rd Edition, 1993, pp. 292-295.*

Rudikoff, S., et al. Single amino acid substitution altering antigen-binding specificity. Immunology, 1982, 79:1979-1983.*

Esnouf et al., A monoclonal antibody raised against human beta-factor XIIa which also recognizes alpha-factor XIIa but not factor XII or complexes of factor XIIa with C1 esterase inhibitor. Thromb Haemost. Jun. 2000;83(6):874-81.

Kenniston et al., Inhibition of plasma kallikrein by a highly specific active site blocking antibody. J Biol Chem. Aug. 22, 2014;289(34):23596-608. doi: 10.1074/jbc.M114.569061. Epub Jun. 26, 2014.

Kontermann, Dual targeting strategies with bispecific antibodies. MAbs. Mar.-Apr. 2012;4(2):182-97. doi: 10.4161/mabs.4.2.19000. Epub Mar. 1, 2012.

Larsson et al., A factor XIIa inhibitory antibody provides thromboprotection in extracorporeal circulation without increasing bleeding risk. Sci Transl Med. Feb. 5, 2014;6(222):222ra17. doi: 10.1126/scitranslmed.3006804.

Mason et al., Discovery and Characterization of a Highly Specific Antibody Inhibitor of Factor XIIa, and the Subsequent Generation of a Factor XIIa/Plasma Kallikrein Bispecific Antibody. Blood. Dec. 2015;126(23):2268.

Coloma et al. Design and production of novel tetravalent bispecific antibodies. Nat Biotechnol. Feb. 1997;15(2):159-63. doi: 10.1038/nbt0297-159.

Holliger et al., Engineered antibody fragments and the rise of single domains. Nat Biotechnol. Sep. 2005;23(9):1126-36. doi: 10.1038/nbt1142.

Kuo et al., Neonatal Fc receptor and IgG-based therapeutics. MAbs. Sep.-Oct. 2011;3(5):422-30. doi: 10.4161/mabs.3.5.16983. Epub Sep. 1, 2011.

Orcutt et al., A modular IgG-scFv bispecific antibody topology. Protein Eng Des Sel. Apr. 2010;23(4):221-8. doi: 10.1093/protein/gzp077. Epub Dec. 17, 2009.

Takehisa et al., A bispecific antibody to factors IXa and X restores factor VIII hemostatic activity in a hemophilia A model. Nat Med. Oct. 2012;18(10):1570-4. doi: 10.1038/nm.2942. Epub Sep. 30, 2012.

* cited by examiner

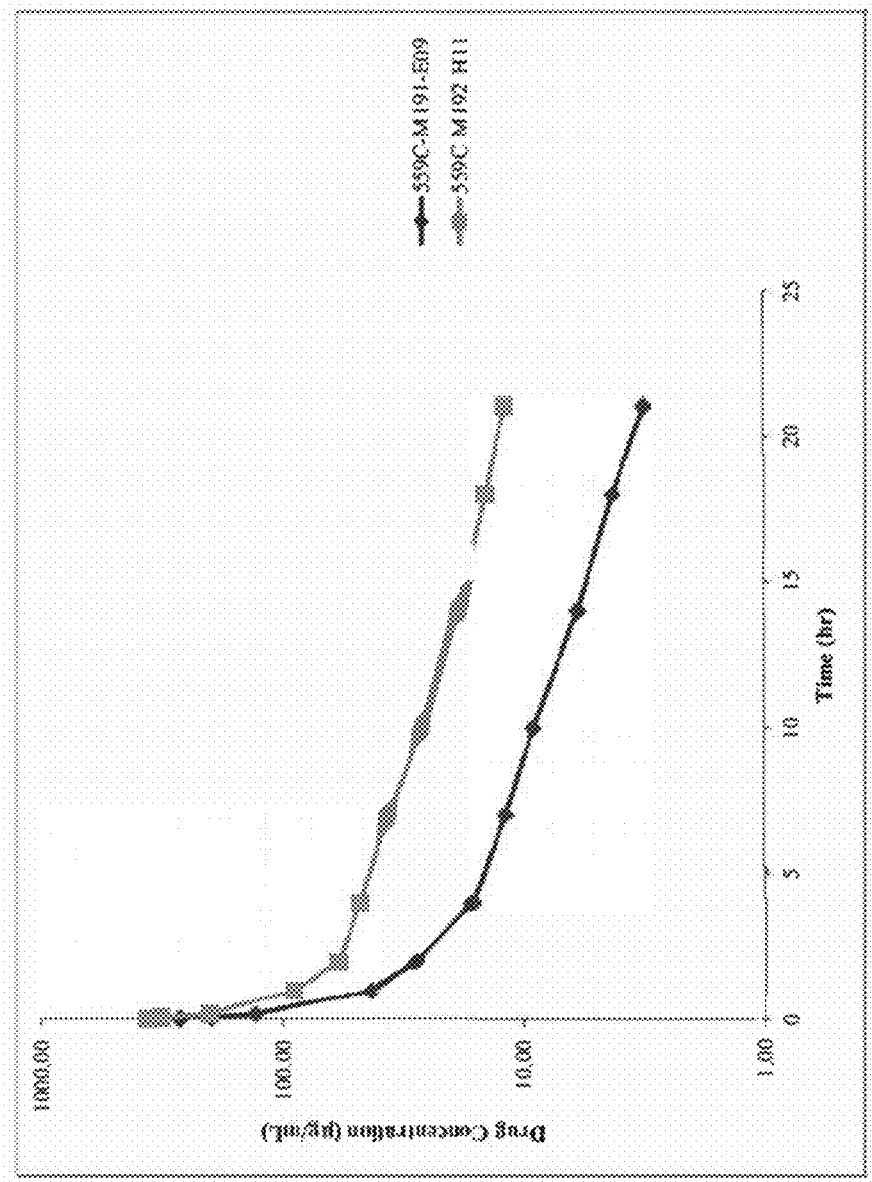

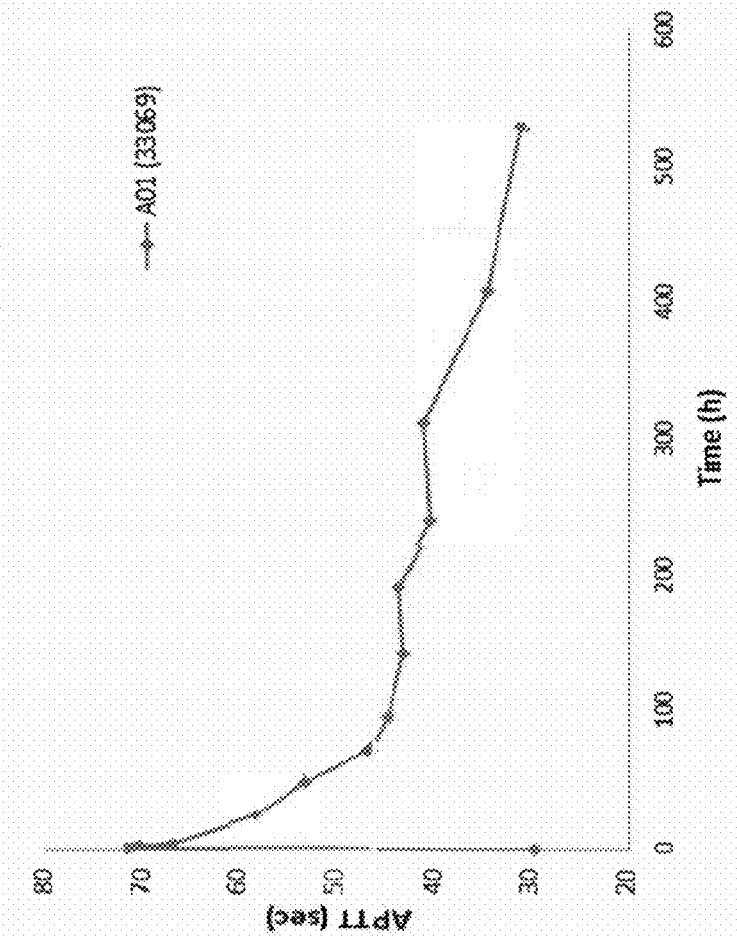

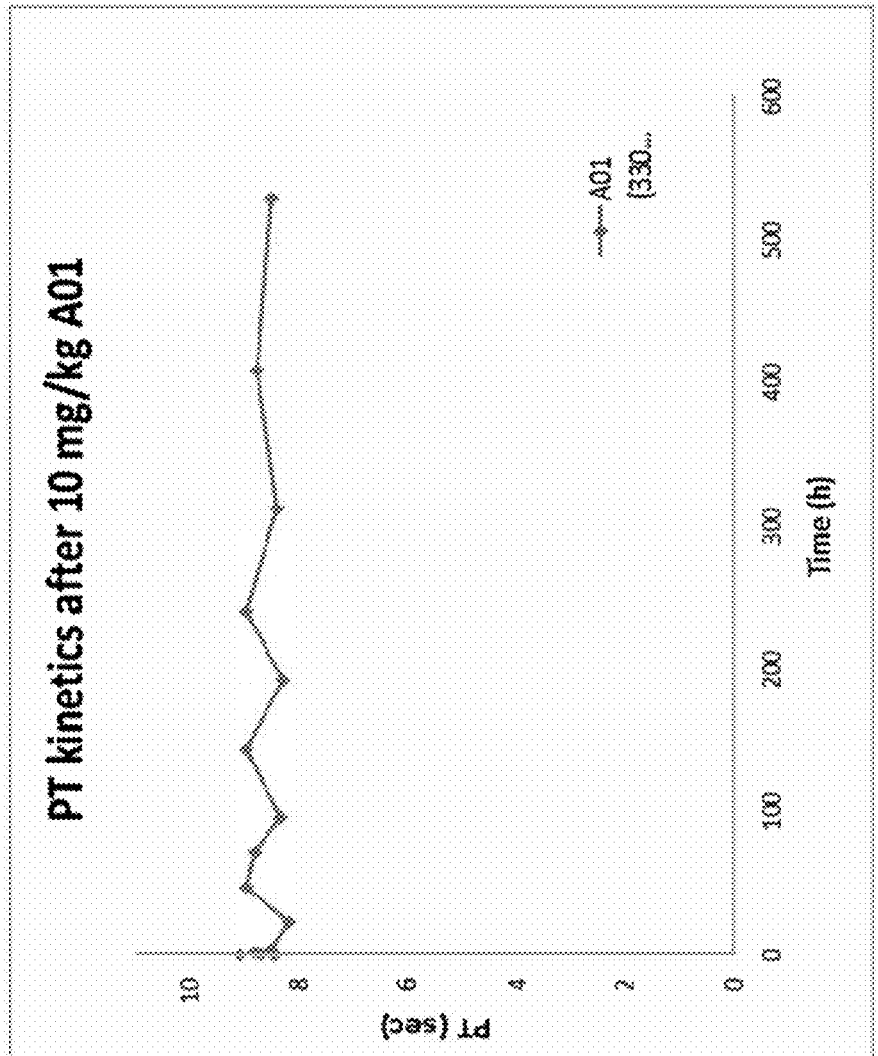

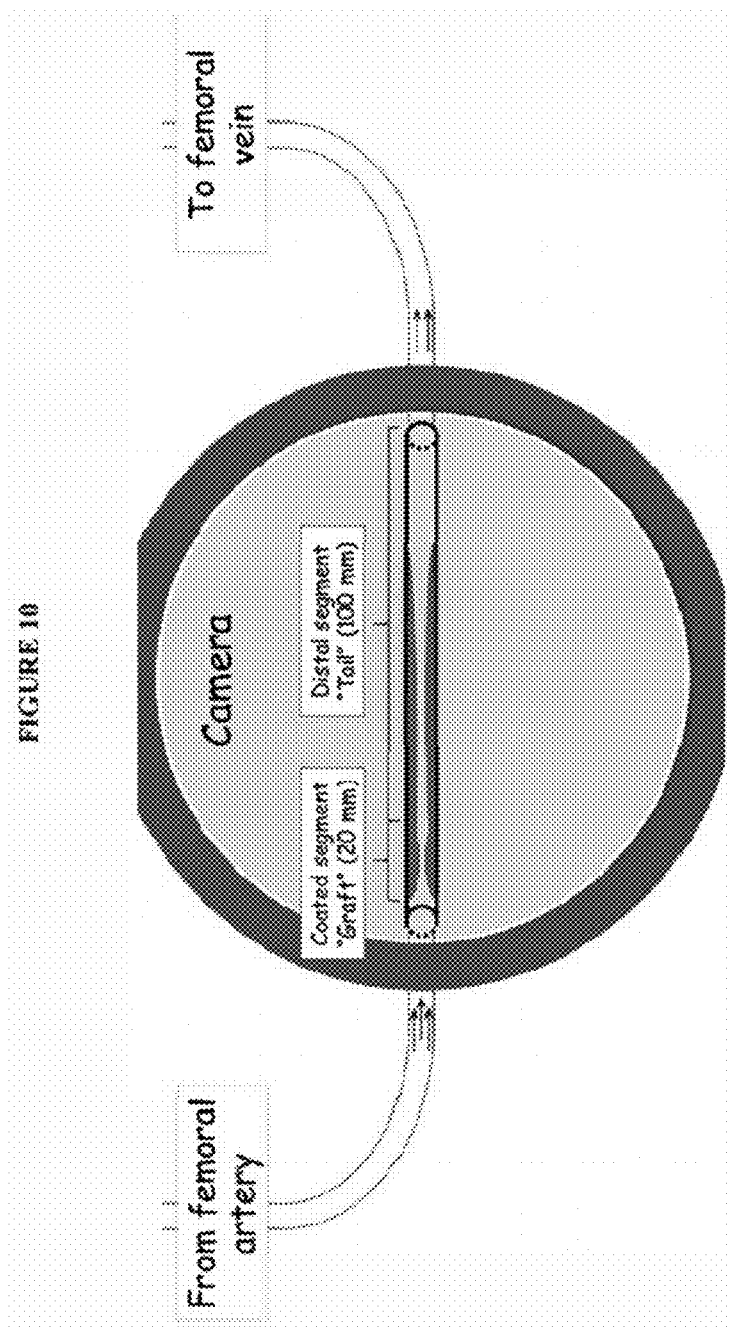

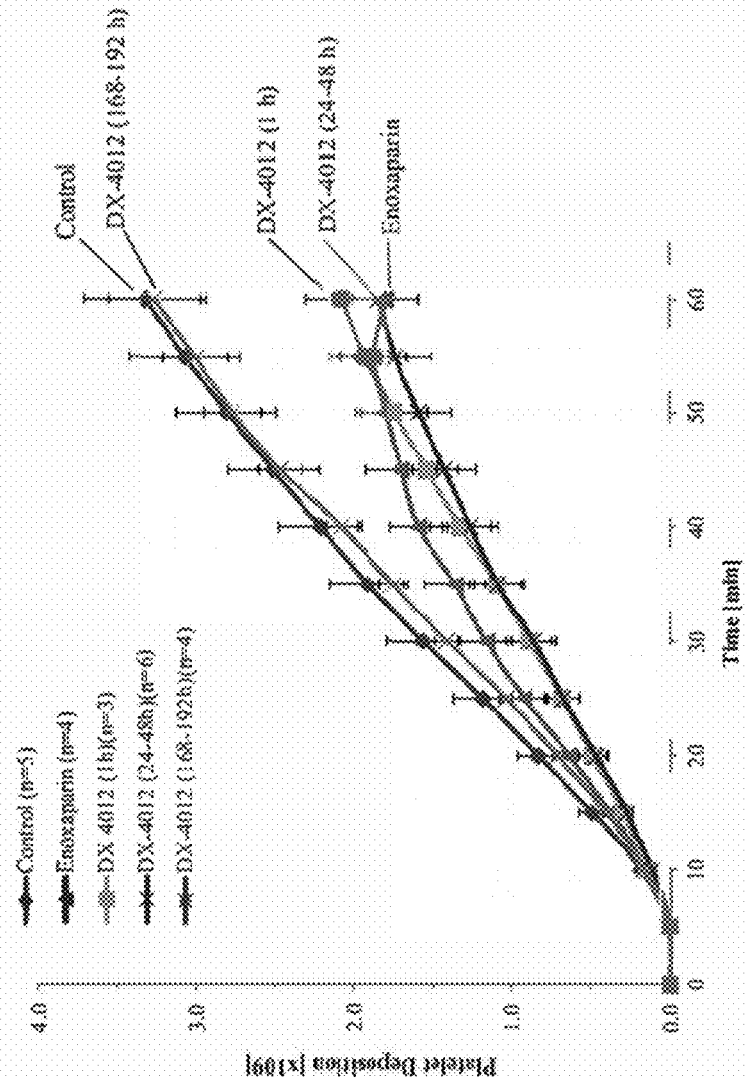

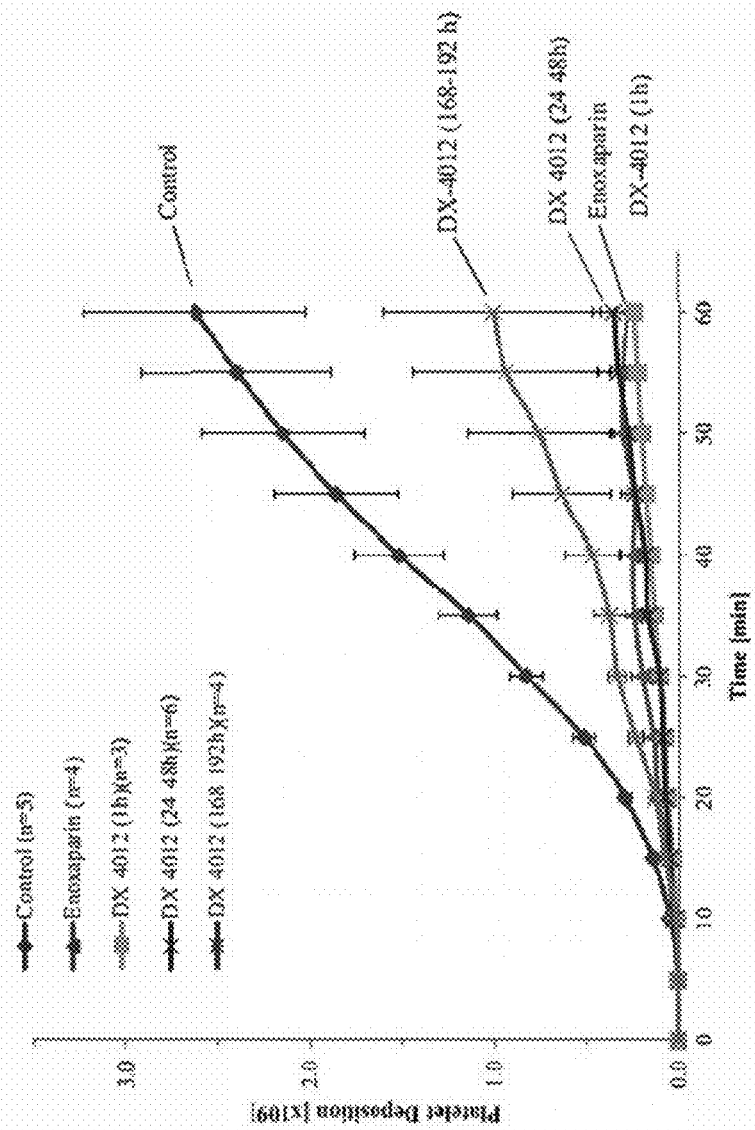

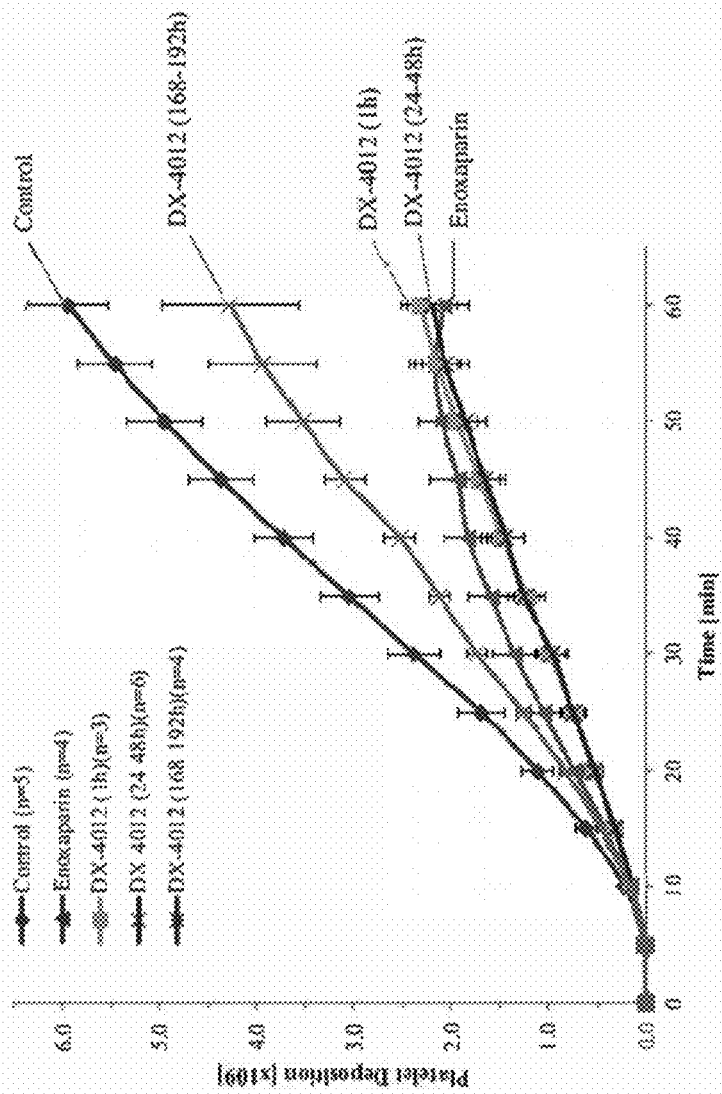

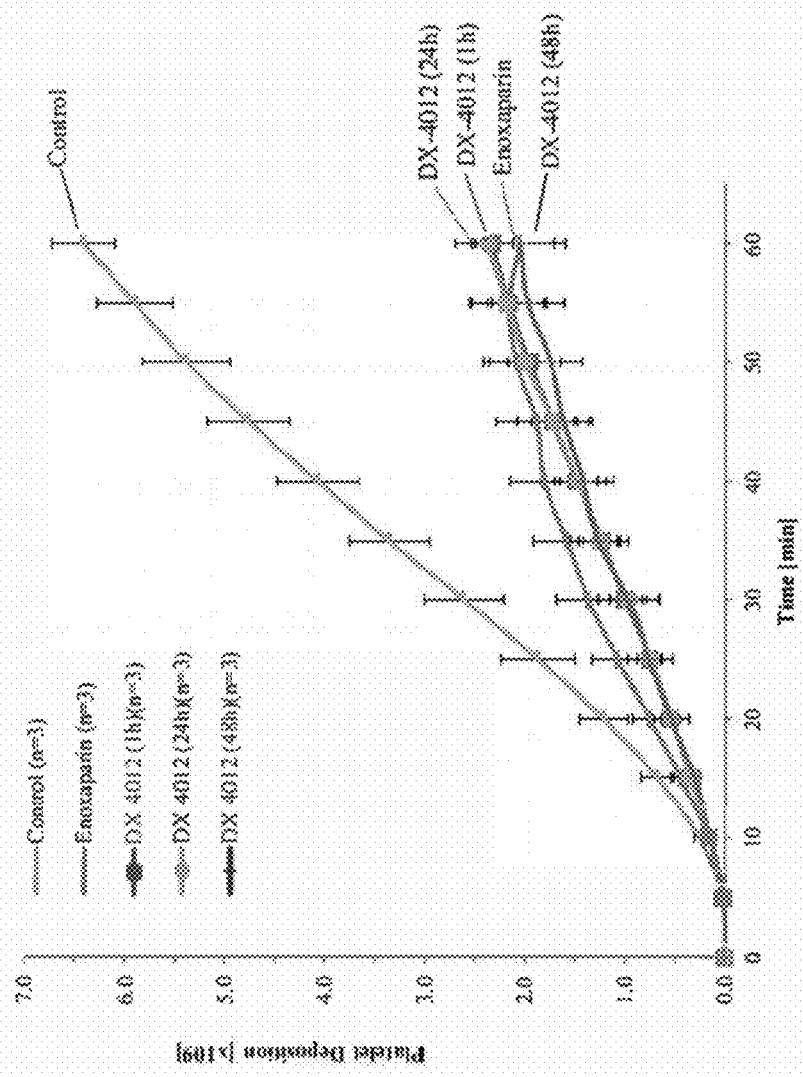

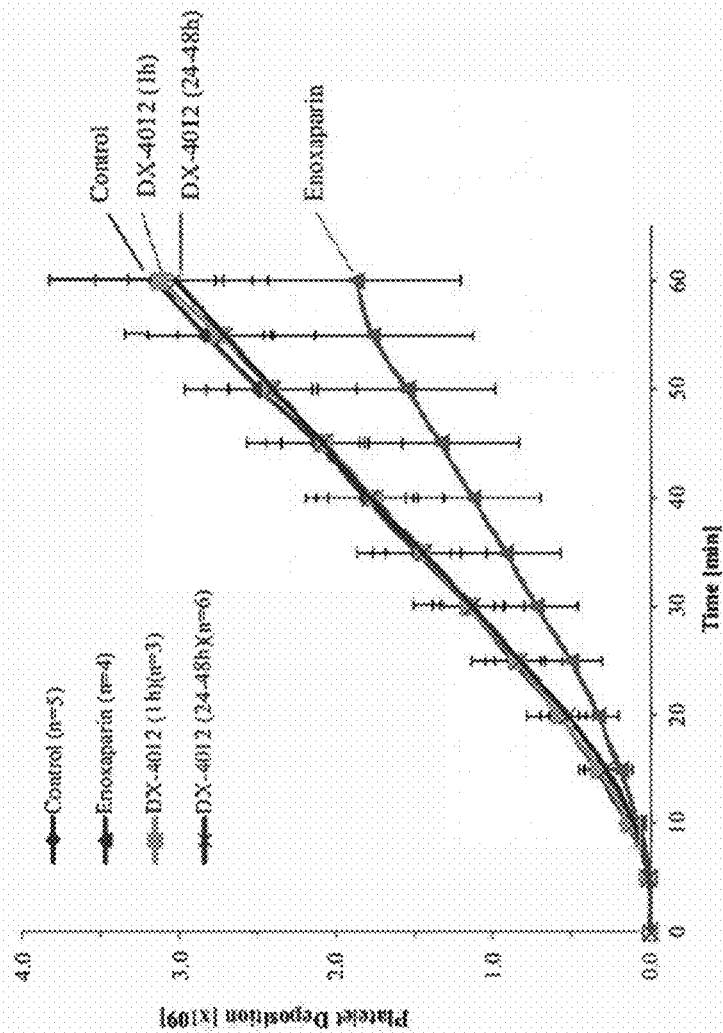

FIGURE 22
A.
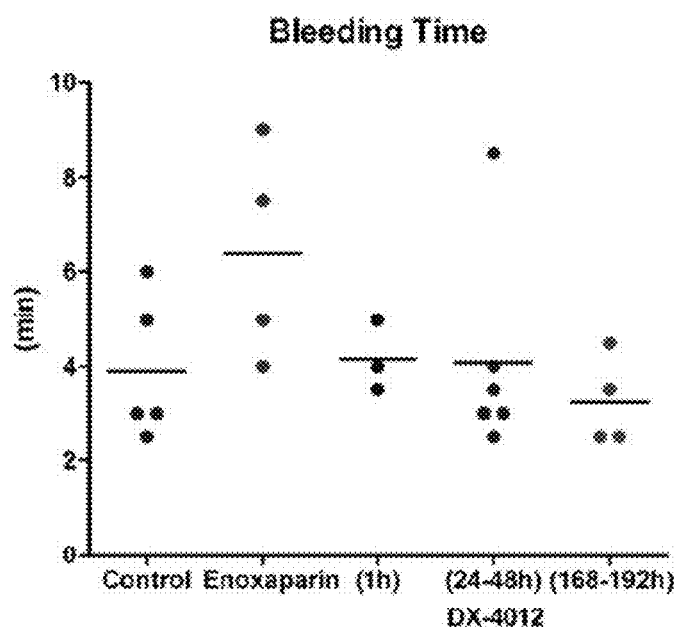
B.
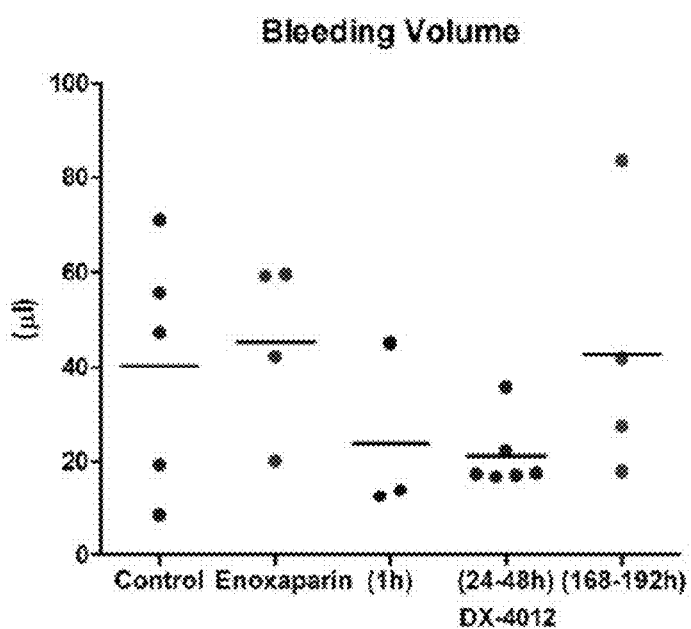

SEQUENCE LISTING

```
<160> NUMBER OF SEQ ID NOS: 128

<210> SEQ ID NO 1
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met His Trp Val Arg Gln Ala Pro Gly Lys Gly Leu Glu Trp Val
        35                  40                  45

Ser Val Ile Tyr Pro Ser Gly Gly Lys Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Tyr Met Asp Val
            100                 105                 110

Trp Gly Lys Gly Thr Thr Val Thr Val Ser Ser
        115                 120

<210> SEQ ID NO 2
<211> LENGTH: 123
<212> TYPE: PRT
<213> ORGANISM: Artificial Sequence
<220> FEATURE:
<223> OTHER INFORMATION: Synthetic Polypeptide
```

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Val Met His Trp Val Arg Gln Ala Pro Gly Lys Gly Leu Glu Trp Val
        35                  40                  45

Ser Ser Ile Trp Pro Ser Gly Gly His Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
                100                 105                 110

Trp Gly Lys Gly Thr Thr Val Thr Val Ser Ser
            115                 120
```

<210> SEQ ID NO 3
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 3

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met His Trp Val Arg Gln Ala Pro Gly Lys Gly Leu Glu Trp Val
        35                  40                  45

Ser Gly Ile Trp Pro Ser Gly Gly Arg Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
                100                 105                 110

Trp Gly Lys Gly Thr Thr Val Thr Val Ser Ser
            115                 120
```

<210> SEQ ID NO 4
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 4

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Val Met His Trp Val Arg Gln Ala Pro Gly Lys Gly Leu Glu Trp Val
        35                  40                  45
```

Ser Ser Ile Trp Pro Ser Gly Gly Lys Thr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Tyr Met Asp Ala
            100                 105                 110

Trp Gly Gln Gly Thr Thr Val Thr Val Ser Ser
            115                 120

<210> SEQ ID NO 5
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 5

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Met Tyr
                20                  25                  30

Thr Met Asn Trp Val Arg Gln Ala Pro Gly Lys Gly Leu Glu Trp Val
            35                  40                  45

Ser Arg Ile Tyr Pro Ser Gly Gly Lys Thr Leu Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Tyr Met Asp Val
            100                 105                 110

Trp Gly Lys Gly Thr Thr Val Thr Val Ser Ser
            115                 120

<210> SEQ ID NO 6
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 6

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gln Tyr
                20                  25                  30

Val Met Ser Trp Val Arg Gln Ala Pro Gly Lys Gly Leu Glu Trp Val
            35                  40                  45

Ser Arg Ile Tyr Pro Ser Gly Gly Val Thr Lys Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Tyr Met Asp Val

```
                    100                 105                 110

Trp Gly Lys Gly Thr Thr Val Thr Val Ser Ser
            115                 120

<210> SEQ ID NO 7
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Asn Met His Trp Val Arg Gln Ala Pro Gly Lys Gly Leu Glu Trp Val
        35                  40                  45

Ser Tyr Ile Ser Pro Ser Gly Lys Thr Lys Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
            100                 105                 110

Trp Gly Lys Gly Thr Thr Val Thr Val Ser Ser
            115                 120

<210> SEQ ID NO 8
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ile Met His Trp Val Arg Gln Ala Pro Gly Lys Gly Leu Glu Trp Val
        35                  40                  45

Ser Ser Ile Tyr Pro Ser Gly Val Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
            100                 105                 110

Trp Gly Lys Gly Thr Thr Val Thr Val Ser Ser
            115                 120

<210> SEQ ID NO 9
<211> LENGTH: 123
<212> TYPE: PRT
<213> ORGANISM: Artificial Sequence
<220> FEATURE:
```

-continued

<223> OTHER INFORMATION: Synthetic Polypeptide

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ile Met Gly Trp Val Arg Gln Ala Pro Gly Lys Gly Leu Glu Trp Val
        35                  40                  45

Ser Ser Ile Tyr Pro Ser Gly Gly Val Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Tyr Met Asp Val
            100                 105                 110

Trp Gly Lys Gly Thr Thr Val Thr Val Ser Ser
        115                 120

<210> SEQ ID NO 10
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Asn Met Val Trp Val Arg Gln Ala Pro Gly Lys Gly Leu Glu Trp Val
        35                  40                  45

Ser Arg Ile Trp Pro Ser Gly Gly Lys Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Tyr Met Asp Val
            100                 105                 110

Trp Gly Lys Gly Thr Thr Val Thr Val Ser Ser
        115                 120

<210> SEQ ID NO 11
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Val Trp Val Arg Gln Ala Pro Gly Lys Gly Leu Glu Trp Val

```
                35                  40                  45
Ser Arg Ile Tyr Pro Ser Gly Gly Met Thr Gln Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Thr Arg Gln Arg Tyr Arg Gly Pro Lys Tyr Tyr Tyr Tyr Met Asp Val
            100                 105                 110
Trp Gly Lys Gly Thr Thr Val Thr Val Ser Ser
            115                 120

<210> SEQ ID NO 12
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 12

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Ser Trp Tyr
             20                  25                  30
Asn Met Ala Trp Val Arg Gln Ala Pro Gly Lys Gly Leu Glu Trp Val
         35                  40                  45
Ser Arg Ile Tyr Pro Ser Gly Gly Met Thr Gln Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Thr Arg Gln Arg Tyr Arg Gly Pro Lys Tyr Tyr Tyr Tyr Met Asp Val
            100                 105                 110
Trp Gly Lys Gly Thr Thr Val Thr Val Ser Ser
            115                 120

<210> SEQ ID NO 13
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 13

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Ser Gln Tyr
             20                  25                  30
Ile Met His Trp Val Arg Gln Ala Pro Gly Lys Gly Leu Glu Trp Val
         35                  40                  45
Ser Ser Ile Tyr Pro Ser Gly Gly Asn Thr Lys Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
```

Thr Arg Gln Arg Tyr Arg Gly Pro Lys Tyr Tyr Tyr Met Asp Val
            100                 105                 110

Trp Gly Lys Gly Thr Thr Val Thr Val Ser Ser
        115                 120

<210> SEQ ID NO 14
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Val Met His Trp Val Arg Gln Ala Pro Gly Lys Gly Leu Glu Trp Val
        35                  40                  45

Ser Ser Ile Tyr Pro Ser Gly Gly Leu Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
            100                 105                 110

Trp Gly Lys Gly Thr Thr Val Thr Val Ser Ser
        115                 120

<210> SEQ ID NO 15
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Thr Met His Trp Val Arg Gln Ala Pro Gly Lys Gly Leu Glu Trp Val
        35                  40                  45

Ser Ser Ile Tyr Pro Ser Gly Gly Phe Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
            100                 105                 110

Trp Gly Lys Gly Thr Thr Val Thr Val Ser Ser
        115                 120

<210> SEQ ID NO 16
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

His Met His Trp Val Arg Gln Ala Pro Gly Lys Gly Leu Glu Trp Val
        35                  40                  45

Ser Arg Ile Val Pro Ser Gly Gly Met Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Tyr Met Asp Val
            100                 105                 110

Trp Gly Lys Gly Thr Thr Val Thr Val Ser Ser
        115                 120

<210> SEQ ID NO 17
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Ser Met His Trp Val Arg Gln Ala Pro Gly Lys Gly Leu Glu Trp Val
        35                  40                  45

Ser Arg Ile Tyr Pro Ser Gly Gly Val Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Tyr Met Asp Val
            100                 105                 110

Trp Gly Lys Gly Thr Thr Val Thr Val Ser Ser
        115                 120

<210> SEQ ID NO 18
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Val Met His Trp Val Arg Gln Ala Pro Gly Lys Gly Leu Glu Trp Val
        35                  40                  45

Ser Ser Ile Trp Pro Ser Gly Gly Lys Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Thr Arg Gln Arg Tyr Arg Gly Pro Lys Tyr Tyr Tyr Met Asp Val
                100                 105                 110

Trp Gly Lys Gly Thr Thr Val Thr Val Ser Ser
            115                 120

<210> SEQ ID NO 19
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Val Met His Trp Val Arg Gln Ala Pro Gly Lys Gly Leu Glu Trp Val
        35                  40                  45

Ser Ser Ile Trp Pro Ser Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Thr Arg Gln Arg Tyr Arg Gly Pro Lys Tyr Tyr Tyr Met Asp Val
                100                 105                 110

Trp Gly Lys Gly Thr Thr Val Thr Val Ser Ser
            115                 120

<210> SEQ ID NO 20
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Asn Met His Trp Val Arg Gln Ala Pro Gly Lys Gly Leu Glu Trp Val
        35                  40                  45

Ser Ser Ile Tyr Pro Ser Gly Val Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Thr Arg Gln Arg Tyr Arg Gly Pro Lys Tyr Tyr Tyr Met Asp Val
                100                 105                 110

Trp Gly Lys Gly Thr Thr Val Thr Val Ser Ser
        115                 120

<210> SEQ ID NO 21
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met His Trp Val Arg Gln Ala Pro Gly Lys Gly Leu Glu Trp Val
        35                  40                  45

Ser Ser Ile Tyr Pro Ser Gly Gly Lys Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
                100                 105                 110

Trp Gly Lys Gly Thr Thr Val Thr Val Ser Ser
        115                 120

<210> SEQ ID NO 22
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Ile Met His Trp Val Arg Gln Ala Pro Gly Lys Gly Leu Glu Trp Val
        35                  40                  45

Ser Val Ile Tyr Pro Ser Gly Ser Lys Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
                100                 105                 110

Trp Gly Lys Gly Thr Thr Val Thr Val Ser Ser
        115                 120

<210> SEQ ID NO 23
<211> LENGTH: 123
<212> TYPE: PRT

<213> ORGANISM: Artificial Sequence
<220> FEATURE:
<223> OTHER INFORMATION: Synthetic Polypeptide

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Arg Trp Val Arg Gln Ala Pro Gly Lys Gly Leu Glu Trp Val
        35                  40                  45

Ser Ser Ile Trp Pro Ser Gly Gly Met Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
            100                 105                 110

Trp Gly Gln Gly Thr Thr Val Thr Val Ser Ser
        115                 120

<210> SEQ ID NO 24
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Val Met His Trp Val Arg Gln Ala Pro Gly Lys Gly Leu Glu Trp Val
        35                  40                  45

Ser Ser Ile Tyr Pro Ser Gly Gly Leu Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
            100                 105                 110

Trp Gly Gln Gly Thr Thr Val Thr Val Ser Ser
        115                 120

<210> SEQ ID NO 25
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ile Met Gly Trp Val Arg Gln Ala Pro Gly Lys Gly Leu Glu Trp Val
         35                  40                  45

Ser Tyr Ile Tyr Pro Ser Gly Gly Asn Thr Arg Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Thr Arg Gln Arg Tyr Arg Gly Pro Lys Tyr Tyr Tyr Tyr Met Asp Val
             100                 105                 110

Trp Gly Lys Gly Thr Thr Val Thr Val Ser Ser
         115                 120

<210> SEQ ID NO 26
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 26

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
             20                  25                  30

Val Met His Trp Val Arg Gln Ala Pro Gly Lys Gly Leu Glu Trp Val
         35                  40                  45

Ser Ser Ile Trp Pro Ser Gly Gly Met Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Thr Arg Gln Arg Tyr Arg Gly Pro Lys Tyr Tyr Tyr Tyr Met Asp Val
             100                 105                 110

Trp Gly Lys Gly Thr Thr Val Thr Val Ser Ser
         115                 120

<210> SEQ ID NO 27
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 27

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Phe Tyr
             20                  25                  30

Ile Met Gly Trp Val Arg Gln Ala Pro Gly Lys Gly Leu Glu Trp Val
         35                  40                  45

Ser Arg Ile Tyr Pro Ser Gly Gly Ala Thr Gln Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys

```
                    85                  90                  95
Thr Arg Gln Arg Tyr Arg Gly Pro Lys Tyr Tyr Tyr Met Asp Val
                100                 105                 110

Trp Gly Lys Gly Thr Thr Val Thr Val Ser Ser
        115                 120

<210> SEQ ID NO 28
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Val Met Gly Trp Val Arg Gln Ala Pro Gly Lys Gly Leu Glu Trp Val
        35                  40                  45

Ser Arg Ile Tyr Pro Ser Gly Gly Leu Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
                100                 105                 110

Trp Gly Lys Gly Thr Thr Val Thr Val Ser Ser
        115                 120

<210> SEQ ID NO 29
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Ser Met His Trp Val Arg Gln Ala Pro Gly Lys Gly Leu Glu Trp Val
        35                  40                  45

Ser Arg Ile Tyr Pro Ser Gly Ile Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
                100                 105                 110

Trp Gly Lys Gly Thr Thr Val Thr Val Ser Ser
        115                 120

<210> SEQ ID NO 30
<211> LENGTH: 123
```

<212> TYPE: PRT
<213> ORGANISM: Artificial Sequence
<220> FEATURE:
<223> OTHER INFORMATION: Synthetic Polypeptide

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Ile Met His Trp Val Arg Gln Ala Pro Gly Lys Gly Leu Glu Trp Val
        35                  40                  45

Ser Ser Ile Tyr Pro Ser Gly Met Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
            100                 105                 110

Trp Gly Lys Gly Thr Thr Val Thr Val Ser Ser
        115                 120

<210> SEQ ID NO 31
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Val Met His Trp Val Arg Gln Ala Pro Gly Lys Gly Leu Glu Trp Val
        35                  40                  45

Ser Ser Ile Tyr Pro Ser Gly Gly Leu Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
            100                 105                 110

Trp Gly Lys Gly Thr Thr Val Thr Val Ser Ser
        115                 120

<210> SEQ ID NO 32
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr

```
                     20                  25                  30
Val Met His Trp Val Arg Gln Ala Pro Gly Lys Gly Leu Glu Trp Val
            35                  40                  45

Ser Arg Ile Tyr Pro Ser Gly Gly Leu Thr Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Tyr Met Asp Val
            100                 105                 110

Trp Gly Lys Gly Thr Thr Val Thr Val Ser Ser
            115                 120

<210> SEQ ID NO 33
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 33

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
                20                  25                  30

Val Met Gln Trp Val Arg Gln Ala Pro Gly Lys Gly Leu Glu Trp Val
            35                  40                  45

Ser Ser Ile Tyr Pro Ser Gly Gly Met Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Tyr Met Asp Val
            100                 105                 110

Trp Gly Lys Gly Thr Thr Val Thr Val Ser Ser
            115                 120

<210> SEQ ID NO 34
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 34

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
                20                  25                  30

Ile Met Gly Trp Val Arg Gln Ala Pro Gly Lys Gly Leu Glu Trp Val
            35                  40                  45

Ser Arg Ile Tyr Pro Ser Gly Gly Ser Thr His Tyr Ala Asp Ser Val
 50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Thr Arg Gln Arg Tyr Arg Gly Pro Arg Tyr Tyr Tyr Ile Asp Ala
            100                 105                 110

Trp Gly Gln Gly Thr Thr Val Thr Val Ser Ser
        115                 120
```

<210> SEQ ID NO 35
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 35

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Thr Met Val Trp Val Arg Gln Ala Pro Gly Lys Gly Leu Glu Trp Val
        35                  40                  45

Ser Arg Ile Tyr Pro Ser Gly Val Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
            100                 105                 110

Trp Gly Lys Gly Thr Thr Val Thr Val Ser Ser
        115                 120
```

<210> SEQ ID NO 36
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 36

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met Tyr Trp Val Arg Gln Ala Pro Gly Lys Gly Leu Glu Trp Val
        35                  40                  45

Ser Arg Ile Tyr Pro Ser Gly Ile Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
            100                 105                 110

Trp Gly Lys Gly Thr Thr Val Thr Val Ser Ser
        115                 120
```

<210> SEQ ID NO 37

```
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Phe Tyr
            20                  25                  30

Val Met Leu Trp Val Arg Gln Ala Pro Gly Lys Gly Leu Glu Trp Val
        35                  40                  45

Ser Ser Ile Trp Pro Ser Gly Gly Val Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
            100                 105                 110

Trp Gly Lys Gly Thr Thr Val Thr Val Ser Ser
        115                 120

<210> SEQ ID NO 38
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Val Met Gln Trp Val Arg Gln Ala Pro Gly Lys Gly Leu Glu Trp Val
        35                  40                  45

Ser Tyr Ile Tyr Pro Ser Gly Gly His Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
            100                 105                 110

Trp Gly Lys Gly Thr Thr Val Thr Val Ser Ser
        115                 120

<210> SEQ ID NO 39
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 39

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Arg Tyr
            20                  25                  30

Ser Met Asn Trp Val Arg Gln Ala Pro Gly Lys Gly Leu Glu Trp Val
        35                  40                  45

Ser Gly Ile Tyr Pro Ser Gly Gly Lys Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
            100                 105                 110

Trp Gly Lys Gly Thr Thr Val Thr Val Ser Ser
        115                 120

<210> SEQ ID NO 40
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 40

Asp Ile Gln Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 41
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 41

Trp Tyr Ser Met His
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 42

Gln Tyr Val Met His
1               5

```
<210> SEQ ID NO 43
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 43

Trp Tyr Val Met His
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 44

Asn Tyr Val Met His
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 45

Met Tyr Thr Met Asn
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 46

Gln Tyr Val Met Ser
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 47

Trp Tyr Asn Met His
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 48

Arg Tyr Ile Met His
1               5

<210> SEQ ID NO 49
```

```
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 49

Arg Tyr Ile Met Gly
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 50

Gln Tyr Asn Met Val
1               5

<210> SEQ ID NO 51
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 51

Arg Tyr Val Met Val
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 52

Trp Tyr Asn Met Ala
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 53

Gln Tyr Ile Met His
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 54

His Tyr Val Met His
1               5

<210> SEQ ID NO 55
<211> LENGTH: 5
```

```
<212> TYPE: PRT
<213> ORGANISM: Artificial Sequence
<220> FEATURE:
<223> OTHER INFORMATION: Synthetic Polypeptide

<400> SEQUENCE: 55

Trp Tyr Thr Met His
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 56

Phe Tyr His Met His
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 57

Phe Tyr Ser Met His
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 58

Gln Tyr Val Met His
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 59

Phe Tyr Asn Met His
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 60

Pro Tyr Ile Met His
1               5

<210> SEQ ID NO 61
<211> LENGTH: 5
<212> TYPE: PRT
```

```
<213> ORGANISM: Artificial Sequence
<220> FEATURE:
<223> OTHER INFORMATION: Synthetic Polypeptide

<400> SEQUENCE: 61

Arg Tyr Thr Met Arg
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 62

Trp Tyr Ile Met Gly
1               5

<210> SEQ ID NO 63
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 63

Arg Tyr Val Met His
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 64

Phe Tyr Ile Met Gly
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 65

Phe Tyr Val Met Gly
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 66

Phe Tyr Ser Met His
1               5

<210> SEQ ID NO 67
<211> LENGTH: 5
<212> TYPE: PRT
<213> ORGANISM: Artificial Sequence
```

<220> FEATURE:
<223> OTHER INFORMATION: Synthetic Polypeptide

<400> SEQUENCE: 67

Met Tyr Ile Met His
1               5

<210> SEQ ID NO 68
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 68

Met Tyr Val Met His
1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 69

Trp Tyr Val Met Gln
1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 70

Gln Tyr Thr Met Val
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 71

Trp Tyr Val Met Tyr
1               5

<210> SEQ ID NO 72
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 72

Phe Tyr Val Met Leu
1               5

<210> SEQ ID NO 73
<211> LENGTH: 5
<212> TYPE: PRT
<213> ORGANISM: Artificial Sequence
<220> FEATURE:

```
<223> OTHER INFORMATION: Synthetic Polypeptide

<400> SEQUENCE: 73

Arg Tyr Ser Met Asn
1               5

<210> SEQ ID NO 74
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 74

Val Ile Tyr Pro Ser Gly Gly Lys Thr Arg Tyr Ala Asp Ser Val Lys
1               5                   10                  15
Gly

<210> SEQ ID NO 75
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 75

Ser Ile Trp Pro Ser Gly Gly His Thr Arg Tyr Ala Asp Ser Val Lys
1               5                   10                  15
Gly

<210> SEQ ID NO 76
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 76

Gly Ile Trp Pro Ser Gly Gly Arg Thr Lys Tyr Ala Asp Ser Val Lys
1               5                   10                  15
Gly

<210> SEQ ID NO 77
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 77

Ser Ile Trp Pro Ser Gly Gly Lys Thr Lys Tyr Ala Asp Ser Val Lys
1               5                   10                  15
Gly

<210> SEQ ID NO 78
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 78

Arg Ile Tyr Pro Ser Gly Gly Lys Thr Leu Tyr Ala Asp Ser Val Lys
1               5                   10                  15
```

Gly

<210> SEQ ID NO 79
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 79

Arg Ile Tyr Pro Ser Gly Gly Val Thr Lys Tyr Ala Asp Ser Val Lys
1               5                   10                  15
Gly

<210> SEQ ID NO 80
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 80

Tyr Ile Ser Pro Ser Gly Gly Lys Thr Lys Tyr Thr Asp Ser Val Lys
1               5                   10                  15
Gly

<210> SEQ ID NO 81
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 81

Ser Ile Tyr Pro Ser Gly Gly Val Thr Lys Tyr Ala Asp Ser Val Lys
1               5                   10                  15
Gly

<210> SEQ ID NO 82
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 82

Ser Ile Tyr Pro Ser Gly Gly Val Thr Arg Tyr Ala Asp Ser Val Lys
1               5                   10                  15
Gly

<210> SEQ ID NO 83
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 83

Arg Ile Trp Pro Ser Gly Gly Lys Thr Thr Tyr Ala Asp Ser Val Lys
1               5                   10                  15
Gly

-continued

```
<210> SEQ ID NO 84
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 84

Arg Ile Tyr Pro Ser Gly Gly Met Thr Gln Tyr Ala Asp Ser Val Lys
1               5                   10                  15
Gly

<210> SEQ ID NO 85
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 85

Ser Ile Tyr Pro Ser Gly Gly Asn Thr Lys Tyr Ala Asp Ser Val Lys
1               5                   10                  15
Gly

<210> SEQ ID NO 86
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 86

Ser Ile Tyr Pro Ser Gly Gly Leu Thr Lys Tyr Ala Asp Ser Val Lys
1               5                   10                  15
Gly

<210> SEQ ID NO 87
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 87

Ser Ile Tyr Pro Ser Gly Gly Phe Thr Arg Tyr Ala Asp Ser Val Lys
1               5                   10                  15
Gly

<210> SEQ ID NO 88
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 88

Arg Ile Val Pro Ser Gly Gly Met Thr Arg Tyr Ala Asp Ser Val Lys
1               5                   10                  15
Gly

<210> SEQ ID NO 89
<211> LENGTH: 17
<212> TYPE: PRT
<213> ORGANISM: Artificial Sequence
```

<220> FEATURE:
<223> OTHER INFORMATION: Synthetic Polypeptide

<400> SEQUENCE: 89

Arg Ile Tyr Pro Ser Gly Gly Val Thr Lys Tyr Ala Asp Ser Val Lys
1               5                   10                  15
Gly

<210> SEQ ID NO 90
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 90

Ser Ile Trp Pro Ser Gly Gly Lys Thr Thr Tyr Ala Asp Ser Val Lys
1               5                   10                  15
Gly

<210> SEQ ID NO 91
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 91

Ser Ile Trp Pro Ser Gly Gly Phe Thr Lys Tyr Ala Asp Ser Val Lys
1               5                   10                  15
Gly

<210> SEQ ID NO 92
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 92

Ser Ile Tyr Pro Ser Gly Gly Val Thr Arg Tyr Ala Asp Ser Val Lys
1               5                   10                  15
Gly

<210> SEQ ID NO 93
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 93

Ser Ile Tyr Pro Ser Gly Gly Lys Thr Ser Tyr Ala Asp Ser Val Lys
1               5                   10                  15
Gly

<210> SEQ ID NO 94
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 94

```
Val Ile Tyr Pro Ser Gly Ser Lys Thr Asn Tyr Ala Asp Ser Val Lys
1               5                   10                  15

Gly

<210> SEQ ID NO 95
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 95

Ser Ile Trp Pro Ser Gly Gly Met Thr Arg Tyr Ala Asp Ser Val Lys
1               5                   10                  15

Gly

<210> SEQ ID NO 96
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 96

Ser Ile Tyr Pro Ser Gly Gly Leu Thr Arg Tyr Ala Asp Ser Val Lys
1               5                   10                  15

Gly

<210> SEQ ID NO 97
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 97

Tyr Ile Tyr Pro Ser Gly Gly Asn Thr Arg Tyr Ala Asp Ser Val Lys
1               5                   10                  15

Gly

<210> SEQ ID NO 98
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 98

Ser Ile Trp Pro Ser Gly Gly Met Thr Lys Tyr Ala Asp Ser Val Lys
1               5                   10                  15

Gly

<210> SEQ ID NO 99
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 99

Arg Ile Tyr Pro Ser Gly Gly Ala Thr Gln Tyr Ala Asp Ser Val Lys
1               5                   10                  15
```

Gly

```
<210> SEQ ID NO 100
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 100

Arg Ile Tyr Pro Ser Gly Gly Leu Thr Gln Tyr Ala Asp Ser Val Lys
1               5                   10                  15

Gly

<210> SEQ ID NO 101
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 101

Arg Ile Tyr Pro Ser Gly Gly Ile Thr Ser Tyr Ala Asp Ser Val Lys
1               5                   10                  15

Gly

<210> SEQ ID NO 102
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 102

Ser Ile Tyr Pro Ser Gly Gly Met Thr Lys Tyr Ala Asp Ser Val Lys
1               5                   10                  15

Gly

<210> SEQ ID NO 103
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 103

Ser Ile Tyr Pro Ser Gly Gly Leu Thr Lys Tyr Ala Asp Ser Val Lys
1               5                   10                  15

Gly

<210> SEQ ID NO 104
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 104

Arg Ile Tyr Pro Ser Gly Gly Leu Thr Asn Tyr Ala Asp Ser Val Lys
1               5                   10                  15

Gly

<210> SEQ ID NO 105
```

```
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 105

Arg Ile Tyr Pro Ser Gly Gly Ser Thr His Tyr Ala Asp Ser Val Lys
1               5                   10                  15
Gly

<210> SEQ ID NO 106
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 106

Arg Ile Tyr Pro Ser Gly Gly Val Thr Gln Tyr Ala Asp Ser Val Lys
1               5                   10                  15
Gly

<210> SEQ ID NO 107
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 107

Arg Ile Tyr Pro Ser Gly Gly Ile Thr His Tyr Ala Asp Ser Val Lys
1               5                   10                  15
Gly

<210> SEQ ID NO 108
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 108

Ser Ile Trp Pro Ser Gly Gly Val Thr Lys Tyr Ala Asp Ser Val Lys
1               5                   10                  15
Gly

<210> SEQ ID NO 109
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 109

Tyr Ile Tyr Pro Ser Gly Gly His Thr Lys Tyr Ala Asp Ser Val Lys
1               5                   10                  15
Gly

<210> SEQ ID NO 110
<211> LENGTH: 17
<212> TYPE: PRT
<213> ORGANISM: Artificial Sequence
<220> FEATURE:
```

```
<223> OTHER INFORMATION: Synthetic Polypeptide

<400> SEQUENCE: 110

Gly Ile Tyr Pro Ser Gly Gly Lys Thr Lys Tyr Ala Asp Ser Val Lys
1               5                   10                  15

Gly

<210> SEQ ID NO 111
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 111

Gln Arg Tyr Arg Gly Pro Lys Tyr Tyr Tyr Tyr Met Asp Val
1               5                   10

<210> SEQ ID NO 112
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 112

Gln Arg Tyr Arg Gly Pro Lys Tyr Tyr Tyr Tyr Met Asp Ala
1               5                   10

<210> SEQ ID NO 113
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 113

Gln Arg Tyr Arg Gly Pro Arg Tyr Tyr Tyr Ile Asp Ala
1               5                   10

<210> SEQ ID NO 114
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 114

Arg Ser Ser Gln Ser Leu Leu His Ser Asn Gly Tyr Asn Tyr Leu Asp
1               5                   10                  15

<210> SEQ ID NO 115
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 115

Leu Gly Ser Asn Arg Ala Ser
1               5

<210> SEQ ID NO 116
<211> LENGTH: 9
<212> TYPE: PRT
<213> ORGANISM: Artificial Sequence
```

```
<220> FEATURE:
<223> OTHER INFORMATION: Synthetic Polypeptide

<400> SEQUENCE: 116

Met Gln Ala Leu Gln Thr Pro Trp Thr
1               5

<210> SEQ ID NO 117
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Arg, Gln, Trp, His, Phe, Pro, Met, or
      Asn
<220> FEATURE:
<221> NAME/KEY: misc_feature
<222> LOCATION: (3)..(3)
<223> OTHER INFORMATION: Xaa is Ile, Val, Thr, His, Ser, or Asn
<220> FEATURE:
<221> NAME/KEY: misc_feature
<222> LOCATION: (5)..(5)
<223> OTHER INFORMATION: Xaa is His, Gly, Val, Ala, Arg, Gln, Tyr, Leu,
      Asn, or Ser

<400> SEQUENCE: 117

Xaa Tyr Xaa Met Xaa
1               5

<210> SEQ ID NO 118
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Ser, Arg, Val, Tyr, or Gly
<220> FEATURE:
<221> NAME/KEY: misc_feature
<222> LOCATION: (3)..(3)
<223> OTHER INFORMATION: Xaa is Tyr, Trp, Val, or Ser
<220> FEATURE:
<221> NAME/KEY: misc_feature
<222> LOCATION: (7)..(7)
<223> OTHER INFORMATION: Xaa is Gly or Ser
<220> FEATURE:
<221> NAME/KEY: misc_feature
<222> LOCATION: (8)..(8)
<223> OTHER INFORMATION: Xaa is Val, Lys, Met, Asn, Leu, Phe, Ala, Ile,
      Ser, His, or Arg
<220> FEATURE:
<221> NAME/KEY: misc_feature
<222> LOCATION: (10)..(10)
<223> OTHER INFORMATION: Xaa is Lys, Arg, Thr, Gln, Ser, Asn, His, or
      Leu
<220> FEATURE:
<221> NAME/KEY: misc_feature
<222> LOCATION: (12)..(12)
<223> OTHER INFORMATION: Xaa is Ala or Thr

<400> SEQUENCE: 118

Xaa Ile Xaa Pro Ser Gly Xaa Xaa Thr Xaa Tyr Xaa Asp Ser Val Lys
1               5                   10                  15

Gly

<210> SEQ ID NO 119
<211> LENGTH: 329
```

<212> TYPE: PRT
<213> ORGANISM: Homo sapiens

<400> SEQUENCE: 119

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 120
<211> LENGTH: 329
<212> TYPE: PRT
<213> ORGANISM: Artificial Sequence
<220> FEATURE:
<223> OTHER INFORMATION: Synthetic Polypeptide

<400> SEQUENCE: 120

Ala Ser Thr Lys Gly Pro Ser Val Phe Pro Leu Ala Pro Ser Ser Lys

```
            1               5                   10                  15
        Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
                    35                  40                  45

Gly Val His Thr Phe Pro Ala Val Leu Gln Ser Ser Gly Leu Tyr Ser
                    50                  55                  60

Leu Ser Ser Val Val Thr Val Pro Ser Ser Leu Gly Thr Gln Thr
        65                  70                  75                  80

Tyr Ile Cys Asn Val Asn His Lys Pro Ser Asn Thr Lys Val Asp Lys
                            85                  90                  95

Arg Val Glu Pro Lys Ser Cys Asp Lys Thr His Thr Cys Pro Pro Cys
                    100                 105                 110

Pro Ala Pro Glu Leu Leu Gly Gly Pro Ser Val Phe Leu Phe Pro Pro
                    115                 120                 125

Lys Pro Lys Asp Thr Leu Tyr Ile Thr Arg Glu Pro Glu Val Thr Cys
                    130                 135                 140

Val Val Val Asp Val Ser His Glu Asp Pro Glu Val Lys Phe Asn Trp
        145                 150                 155                 160

Tyr Val Asp Gly Val Glu Val His Asn Ala Lys Thr Lys Pro Arg Glu
                            165                 170                 175

Glu Gln Tyr Asn Ser Thr Tyr Arg Val Val Ser Val Leu Thr Val Leu
                    180                 185                 190

His Gln Asp Trp Leu Asn Gly Lys Glu Tyr Lys Cys Lys Val Ser Asn
                    195                 200                 205

Lys Ala Leu Pro Ala Pro Ile Glu Lys Thr Ile Ser Lys Ala Lys Gly
                    210                 215                 220

Gln Pro Arg Glu Pro Gln Val Tyr Thr Leu Pro Pro Ser Arg Glu Glu
        225                 230                 235                 240

Met Thr Lys Asn Gln Val Ser Leu Thr Cys Leu Val Lys Gly Phe Tyr
                            245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
                    290                 295                 300

Val Phe Ser Cys Ser Val Met His Glu Ala Leu His Asn His Tyr Thr
        305                 310                 315                 320

Gln Lys Ser Leu Ser Leu Ser Pro Gly
                            325

<210> SEQ ID NO 121
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 121

Gln Tyr Ser Met His
1               5

<210> SEQ ID NO 122
<211> LENGTH: 17
<212> TYPE: PRT
```

<213> ORGANISM: Artificial Sequence
<220> FEATURE:
<223> OTHER INFORMATION: Synthetic Polypeptide

<400> SEQUENCE: 122

Ser Ile Tyr Pro Ser Gly Gly Lys Thr Arg Tyr Ala Asp Ser Val Lys
1               5                   10                  15

Gly

<210> SEQ ID NO 123
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 123

Val Ile Trp Pro Ser Gly Gly Lys Thr Arg Tyr Ala Asp Ser Val Lys
1               5                   10                  15

Gly

<210> SEQ ID NO 124
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 124

Val Ile Tyr Pro Ser Gly Gly His Thr Arg Tyr Ala Asp Ser Val Lys
1               5                   10                  15

Gly

<210> SEQ ID NO 125
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Val Met His Trp Val Arg Gln Ala Pro Gly Lys Gly Leu Glu Trp Val
        35                  40                  45

Ser Ser Ile Trp Pro Ser Gly Gly His Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gln Arg Tyr Arg Gly Pro Lys Tyr Tyr Tyr Met Asp Val
                100                 105                 110

Trp Gly Lys Gly Thr Thr Val Thr Val Ser Ser
            115                 120

<210> SEQ ID NO 126
<211> LENGTH: 112
<212> TYPE: PRT

```
<213> ORGANISM: Artificial Sequence
<220> FEATURE:
<223> OTHER INFORMATION: Synthetic Polypeptide

<400> SEQUENCE: 126

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 127
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 127

Ser Ile Trp Pro Ser Gly Gly His Thr Arg Tyr Ala Asp Ser Val His
1               5                   10                  15

Gly

<210> SEQ ID NO 128
<211> LENGTH: 615
<212> TYPE: PRT
<213> ORGANISM: Homo sapiens

<400> SEQUENCE: 128

Met Arg Ala Leu Leu Leu Gly Phe Leu Leu Val Ser Leu Glu Ser
1               5                   10                  15

Thr Leu Ser Ile Pro Pro Trp Glu Ala Pro Lys Glu His Lys Tyr Lys
            20                  25                  30

Ala Glu Glu His Thr Val Val Leu Thr Val Thr Gly Glu Pro Cys His
        35                  40                  45

Phe Pro Phe Gln Tyr His Arg Gln Leu Tyr His Lys Cys Thr His Lys
    50                  55                  60

Gly Arg Pro Gly Pro Gln Pro Trp Cys Ala Thr Thr Pro Asn Phe Asp
65                  70                  75                  80

Gln Asp Gln Arg Trp Gly Tyr Cys Leu Glu Pro Lys Lys Val Lys Asp
                85                  90                  95

His Cys Ser Lys His Ser Pro Cys Gln Lys Gly Gly Thr Cys Val Asn
            100                 105                 110

Met Pro Ser Gly Pro His Cys Leu Cys Pro Gln His Leu Thr Gly Asn
        115                 120                 125

His Cys Gln Lys Glu Lys Cys Phe Glu Pro Gln Leu Leu Arg Phe Phe
    130                 135                 140

His Lys Asn Glu Ile Trp Tyr Arg Thr Glu Gln Ala Ala Val Ala Arg
145                 150                 155                 160
```

```
Cys Gln Cys Lys Gly Pro Asp Ala His Cys Gln Arg Leu Ala Ser Gln
                165                 170                 175

Ala Cys Arg Thr Asn Pro Cys Leu His Gly Gly Arg Cys Leu Glu Val
            180                 185                 190

Glu Gly His Arg Leu Cys His Cys Pro Val Gly Tyr Thr Gly Ala Phe
        195                 200                 205

Cys Asp Val Asp Thr Lys Ala Ser Cys Tyr Asp Gly Arg Gly Leu Ser
    210                 215                 220

Tyr Arg Gly Leu Ala Arg Thr Thr Leu Ser Gly Ala Pro Cys Gln Pro
225                 230                 235                 240

Trp Ala Ser Glu Ala Thr Tyr Arg Asn Val Thr Ala Glu Gln Ala Arg
                245                 250                 255

Asn Trp Gly Leu Gly Gly His Ala Phe Cys Arg Asn Pro Asp Asn Asp
            260                 265                 270

Ile Arg Pro Trp Cys Phe Val Leu Asn Arg Asp Arg Leu Ser Trp Glu
        275                 280                 285

Tyr Cys Asp Leu Ala Gln Cys Gln Thr Pro Thr Gln Ala Ala Pro Pro
    290                 295                 300

Thr Pro Val Ser Pro Arg Leu His Val Pro Leu Met Pro Ala Gln Pro
305                 310                 315                 320

Ala Pro Pro Lys Pro Gln Pro Thr Thr Arg Thr Pro Pro Gln Ser Gln
                325                 330                 335

Thr Pro Gly Ala Leu Pro Ala Lys Arg Glu Gln Pro Pro Ser Leu Thr
            340                 345                 350

Arg Asn Gly Pro Leu Ser Cys Gly Gln Arg Leu Arg Lys Ser Leu Ser
        355                 360                 365

Ser Met Thr Arg Val Val Gly Gly Leu Val Ala Leu Arg Gly Ala His
    370                 375                 380

Pro Tyr Ile Ala Ala Leu Tyr Trp Gly His Ser Phe Cys Ala Gly Ser
385                 390                 395                 400

Leu Ile Ala Pro Cys Trp Val Leu Thr Ala Ala His Cys Leu Gln Asp
                405                 410                 415

Arg Pro Ala Pro Glu Asp Leu Thr Val Val Leu Gly Gln Glu Arg Arg
            420                 425                 430

Asn His Ser Cys Glu Pro Cys Gln Thr Leu Ala Val Arg Ser Tyr Arg
        435                 440                 445

Leu His Glu Ala Phe Ser Pro Val Ser Tyr Gln His Asp Leu Ala Leu
    450                 455                 460

Leu Arg Leu Gln Glu Asp Ala Asp Gly Ser Cys Ala Leu Leu Ser Pro
465                 470                 475                 480

Tyr Val Gln Pro Val Cys Leu Pro Ser Gly Ala Ala Arg Pro Ser Glu
                485                 490                 495

Thr Thr Leu Cys Gln Val Ala Gly Trp Gly His Gln Phe Glu Gly Ala
            500                 505                 510

Glu Glu Tyr Ala Ser Phe Leu Gln Glu Ala Gln Val Pro Phe Leu Ser
        515                 520                 525

Leu Glu Arg Cys Ser Ala Pro Asp Val His Gly Ser Ser Ile Leu Pro
    530                 535                 540

Gly Met Leu Cys Ala Gly Phe Leu Glu Gly Gly Thr Asp Ala Cys Gln
545                 550                 555                 560

Gly Asp Ser Gly Gly Pro Leu Val Cys Glu Asp Gln Ala Ala Glu Arg
                565                 570                 575
```

```
Arg Leu Thr Leu Gln Gly Ile Ile Ser Trp Gly Ser Gly Cys Gly Asp
            580                 585                 590

Arg Asn Lys Pro Gly Val Tyr Thr Asp Val Ala Tyr Tyr Leu Ala Trp
        595                 600                 605

Ile Arg Glu His Thr Val Ser
    610                 615
```

MONOCLONAL ANTIBODY INHIBITOR OF FACTOR XIIA

CROSS REFERENCE TO RELATED APPLICATIONS

This application is a national stage filing under 35 U.S.C. § 371 of international application number PCT/US2016/043265, filed Jul. 21, 2016, which claims the benefit under 35 U.S.C § 119(e) of the filing date of U.S. Provisional Application No. 62/194,957 filed Jul. 21, 2015, U.S. Provisional Application No. 62/273,657, filed Dec. 31, 2015, and U.S. Provisional Application No. 62/316,310, filed Mar. 31, 2016. The entire contents of each of these referenced applications are incorporated by reference herein.

BACKGROUND OF INVENTION

Factor XII (FXII) is a component of the plasma contact activation system responsible for both the initiation of intrinsic coagulation and the conversion of pre-kallikrein into plasma kallikrein (pKal). Active pKal cleaves high molecular weight kininogen (HMWK) to release bradykinin which is a potent activator of edema and pain. Activation of the intrinsic pathway for blood coagulation leads to the generation of fibrin and formation of blood clots (thrombus).

SUMMARY OF INVENTION

The present disclosure is based on the identification of a number of antibodies that specifically bind Factor XIIa (FXIIa) but not Factor XII (FXII). These antibodies have high binding affinity to FXIIa (e.g., $Ki^{app}$<50 pM); successfully reduced the activation of plasma kallikrein; and delayed activated partial thromboplastin time (APTT) but had no effect on prothrombin time (PT).

Accordingly, one aspect of the present disclosure features a monoclonal antibody that binds to Factor XIIa (FXIIa) and does not bind to Factor XII (FXII). In some embodiments, the antibody is a full length antibody or an antigen-binding fragment thereof, such as an Fab. In some embodiments, the antibody is a human antibody or a humanized antibody.

In some embodiments, the antibody interacts with one or more amino acid residues in chain C of FXIIa. In some examples, the amino acid residues are selected from L390, Y391, W392, G393, H394, S395, F396, C397, H412, C413, L414, Q415, D416, R432, N433, V456, Y458, H507, F509, E510, G511, A512, E513, Y515, D557, A558, C559, Q560, G561, D562, S563, I584, S585, W586, G587, S588, G589, C590, G591, D592, and G597 in SEQ ID NO: 128. In some embodiments, the antibody binds to a fragment of FXIIa comprising residues 390-397, 412-416, 432-433, 456-458, 507-515, 557-563 or 584-592 of SEQ ID NO: 128.

In some examples, the anti-FXIIa antibodies described herein comprises (a) a heavy chain comprising a heavy chain variable region that comprises a heavy chain complementarity determining region 1 (CDR1), a heavy chain complementarity determining region 2 (CDR2), and a heavy chain complementarity determining region 3 (CDR3), and optionally (b) a light chain comprising a light chain variable region that comprises a light chain CDR1, a light chain CDR2, and a light chain CDR3.

In some embodiments, the heavy chain variable region comprises a heavy chain CDR3 that comprises an amino acid sequence of QRYRGPKYYYYMDV (SEQ ID NO: 111), QRYRGPKYYYYMDA (SEQ ID NO: 112), or QRYRGPRYYYYIDA (SEQ ID NO: 113). Such a heavy chain variable region may further comprise a heavy chain CDR1 that comprises the formula $X_1YX_3MX_5$ (SEQ ID NO: 117), in which: $X_1$ is R, Q, W, H, F, P, M, or N; $X_3$ is I, V, T, H, S, or N; and $X_5$ is H, G, V, A, R, Q, Y, L, N, or S. In some examples, $X_1$ of CDR1 is W or Q; $X_3$ of CDR1 is S or V; and/or $X_5$ is H. In some examples, the heavy chain CDR1 may comprise an amino acid sequence of any of SEQ ID NOs:41-73 and 121.

Alternatively or in addition, the heavy chain variable region of the anti-FXIIa antibodies described herein may further comprise a heavy chain CDR2 that comprises the formula $X_1IX_3PSGX_7X_8TX_{10}YX_{12}DSVKG$, (SEQ ID NO: 118), in which $X_1$ is S, R, V, Y, or G, $X_3$ is Y, W, V, or S; $X_7$ is G or S; $X_8$ is V, K, M, N, L, F, A, I, S, H, or R; $X_{10}$ is K, R, T, Q, S, N, H, or L, and $X_{12}$ is A or T. In some examples, $X_1$ of CDR2 is V or S, $X_3$ of CDR2 is Y or W, $X_7$ of CDR2 is G, $X_8$ of CDR2 is K or H, $X_{10}$ of CDR2 is R, and/or $X_{12}$ of CDR2 is A. In some examples, the heavy chain CDR2 comprises an amino acid sequence of any of SEQ ID NOs:74-110, 122-124, and 127.

In certain embodiments, the heavy chain variable region of the anti-FXIIa antibodies described herein comprises a combination of a heavy chain CDR1, a heavy chain CDR2, and a heavy chain CDR3 as presented in Table 1.

In some examples, the heavy chain of the anti-FXIIa antibodies described herein comprises a heavy chain variable region that comprises an amino acid sequence of any of SEQ ID NOs: 1-39, and SEQ ID NO: 125.

Any of the heavy chains of the anti-FXIIa antibodies described herein may further comprise a heavy chain constant region. In some embodiments, the heavy chain constant region comprises at least one mutation (e.g., amino acid substitution) that enhances half-life of the antibody as compared to the wild-type counterpart. Such a mutated heavy chain constant region may comprise at least one mutation at a position corresponding to position 145, 147, or 149 of SEQ ID NO:119, which represents the amino acid sequence of an exemplary wild-type human heavy chain constant region. The at least one mutation may be an amino acid substitution of M145Y, S147T, and/or T149E. In some examples, the mutated heavy chain constant region comprises amino acid substitutions at positions 145, 147, and 149 of SEQ ID NO:119 (e.g., M145Y, S147T, and T149E). Such a mutated heavy chain may comprise the amino acid sequence of SEQ ID NO:120.

The light chain variable region of the anti-FXIIa antibodies described herein may comprise a light chain CDR3 that comprises the amino acid sequence of MQALQTPWT (SEQ ID NO: 116). In some examples, the light chain variable region may further comprise a light chain CDR1 that comprises the amino acid sequence of RSSQSLLHSNGYNYLD (SEQ ID NO: 114). Alternatively or in addition, the light chain variable region may further comprise a light chain CDR2 that comprises the amino acid sequence of LGSNRAS (SEQ ID NO:115). In some examples, the light chain of the anti-FXIIa antibodies described herein may comprise a light chain variable region that comprises the amino acid sequence of SEQ ID NO: 40 or SEQ ID NO:126.

Any of the anti-FXIIa antibodies described herein can be full length antibodies or antigen-binding fragments thereof. In some examples, the antibodies can be human antibodies or humanized antibodies.

Also within the scope of the present disclosure are an isolated nucleic acid or a set of nucleic acids, which collectively encode any of the anti-FXIIa antibodies (e.g., encoding at least the heavy and light chain variable regions of an antibody) described herein, a vector or vector set (e.g., expression vectors) that comprise the nucleic acid or the set of nucleic acids, and a host cell or host cell set that comprises the vector or vector set. Exemplary host cells include, but are not limited to, bacterial cells, yeast cells, insect cells, plant cells, and mammalian cells such as CHO cells.

Further, the present disclosure provides a method of producing any of the anti-FXIIa antibodies described herein. The method comprises culturing a host cell or host cell set that comprises a vector or vector set, which collectively encodes the antibody, and collecting the cultured cells or the culture medium for isolation of the antibody. Such a method can further comprise isolating the antibody from the cultured cells or the culture medium.

In another aspect, the present disclosure provides a method for treating a disease associated with Factor XII, e.g., diseases associated contact system activation, diseases associated with the pKal signaling pathway such as hereditary angioedema or HAE, or ocular diseases (e.g., macular edema, diabetic retinopathy, hypertensive retinopathy, age-related macular degeneration, or retinal vein occlusion) in a subject. Such methods may comprise administering to a subject in need thereof an effective amount of a composition comprising an antibody that binds to FXIIa and may not bind to FXII (e.g., any of the anti-FXIIa antibodies described herein), one or more nucleic acids that, collectively encode the antibody, or expression vectors comprising such nucleic acid(s). In some embodiments, the antibody specifically binds the catalytic domain of FXIIa. In other embodiments, the antibody inhibits the activation of FXI to FXIa. In yet other embodiments, the $Ki^{app}$ of the antibody is lower than about 110 pM (e.g., lower than about 50 pM or 10 pM).

The subject to be treated by the method described herein may be a human subject having, suspected of having, or at risk for the pKal-associated disease (e.g., HAE). In some examples, the subject has, is suspected of having, or is at risk for Type I, Type II, or Type III HAE.

In some embodiments, the subject to be treated by the methods described herein may be a human subject having, suspected of having, or at risk for a disease associated with Factor XII such as those disclosed herein (e.g., a disease associated with contact system activation). For example, the subject may have, suspected of have, or at risk for a disease associated with contact system activation, such as thrombosis, including thrombosis associated with atrial fibrillation, deep vein thrombosis (DVT), pulmonary embolism, stroke, or an arterial or venous thrombotic event. In another example, the subject may have, suspected of having, or at risk for a disease associated with the pKal signaling pathway, e.g., HAE such as Type I, Type II, or Type III HAE. In yet another example, the subject may have, suspected of having, or at risk for an ocular disease, which can be macular edema, diabetic retinopathy, hypertensive retinopathy, age-related macular degeneration, or retinal vein occlusions.

Also within the scope of the present disclosure are pharmaceutical compositions comprising any of the anti-FXIIa antibodies described herein and a pharmaceutically acceptable carrier. Such pharmaceutical composition can be for use in treating a disease associated with the pKal signaling pathway (e.g., HAE such as Type I, Type II, or Type III HAE), or for use in manufacturing medicaments for use in treating such a disease.

The details of one or more embodiments of the invention are set forth in the description below. Other features or advantages of the present invention will be apparent from the following drawing and detailed description of several embodiments, and also from the appended claims.

BRIEF DESCRIPTION OF DRAWINGS

The following drawing forms part of the present specification and is included to further demonstrate certain aspects of the present disclosure, which can be better understood by reference to the drawing in combination with the detailed description of specific embodiments presented herein.

FIG. 6 shows the concentration of the exemplary anti-FXIIa antibodies M191-E09 and M192-H11 in the plasma of rats at various time points following injection of the anti-FXIIa antibodies.

FIG. 10 is a schematic of the external loop of a chronic arteriovenous (AV) shunt during thrombosis studies in non-human primates. The external loop is extended over the top of a gamma camera for real time measurement of platelet deposition.

FIG. 11 is a chart showing the time course of platelet deposition on a collagen-coated graft. A: Thrombus head. B: Thrombus tail.

FIG. 12 is a chart showing the time course of platelet deposition on a collagen-coated graft.

FIG. 13 is a chart showing the time course of platelet deposition (total thrombus) on a collagen-coated graft.

FIG. 22 is a chart showing hemostasis measurements associated with DX-4012. A: Bleeding time. B: Bleeding volume.

DETAILED DESCRIPTION OF INVENTION

Figure 1:
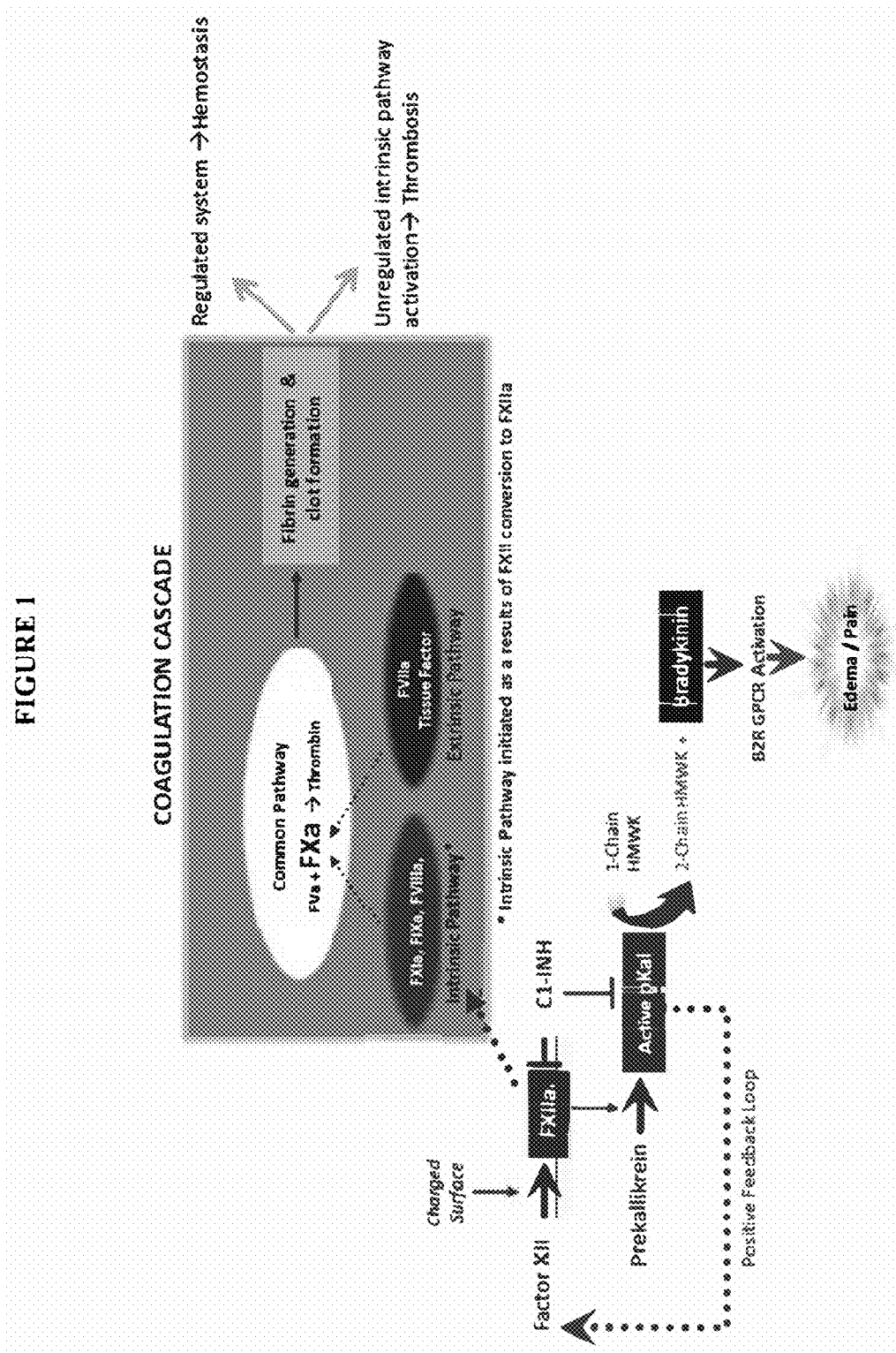
FIG. 1 is a schematic illustration showing the coagulation cascade, in which Factor XII is involved.

Components of the contact system initiate the intrinsic pathway of coagulation and promote inflammation through the release of the proinflammatory peptide bradykinin. Factor XII (FXII), also known as Hageman Factor, is a serine protease that plays a role in activation of the intrinsic pathway of coagulation as well as the kallikrein-kinin system. FXII is activated by negatively charged surfaces (e.g., polyanionic surfaces, glass, polyphosphate, ellagic acid) to produce the active form FXIIa. Activated FXIIa has the ability to cleave pre-kallikrein, generating active pKal. Subsequently, activated pKal is able to cleave FXII into FXIIa, resulting in a positive feedback loop in which FXIIa generates even more pKal, which further activates additional FXII into FXIIa. Activated pKal is also able to cleave high molecular weight kininogen (HMWK) to release bradykinin. The coagulation cascade, in which FXII is involved, is illustrated in FIG. 1.

In diseases associated with contact system activation, such as HAE, increased levels of bradykinin can induce vasodilation and inflammation that result in edematous HAE attacks. Accordingly, it is desired to develop novel therapeutics for treating a range of diseases that are potentially mediated by the activation of the contact system.

Described herein are antibodies that bind to and inhibit FXIIa, and uses thereof in inhibiting FXIIa and treating diseases associated with contact system activation. As shown in the Examples below, a number of exemplary anti-FXIIa antibodies were generated and shown to specifically bind to and inhibit the activity of FXIIa. Such antibodies as exemplified herein are expected to exhibit enhanced therapeutic effects in treating disease associated with contact system activation, particularly reducing the production of bradykinin, vasodilation, and pathological thrombi formation associated with disease symptoms.

Antibodies Binding to FXIIa

The present disclosure provides antibodies that bind FXIIa, for example, the catalytic domain of FXIIa. Such antibodies may not bind to FXII.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, nanobodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

In some embodiments, the anti-FXIIa antibody as described herein can bind and inhibit the activity of FXIIa by at least 50% (e.g., 60%, 70%, 80%, 90%, 95% or greater). The apparent inhibition constant ($K_i^{app}$ or $K_{i,app}$), which provides a measure of inhibitor potency, is related to the concentration of inhibitor required to reduce enzyme activity and is not dependent on enzyme concentrations. The inhibitory activity of an anti-FXIIa antibody described herein can be determined by routine methods known in the art.

The $K_{i}^{app}$ value of an antibody may be determined by measuring the inhibitory effect of different concentrations of the antibody on the extent of the reaction (e.g., enzyme activity); fitting the change in pseudo-first order rate constant (v) as a function of inhibitor concentration to the modified Morrison equation (Equation 1) yields an estimate of the apparent Ki value. For a competitive inhibitor, the $K_i^{app}$ can be obtained from the y-intercept extracted from a linear regression analysis of a plot of $K_{i,}^{app}$ versus substrate concentration.

$$v = A \cdot \frac{([E] - [I] - K_i^{app}) + \sqrt{([E] - [I] - K_i^{app})^2 + 4[E] \cdot K_i^{app}}}{2}$$ (Equation 1)

Where A is equivalent to $v_o/E$, the initial velocity ($v_o$) of the enzymatic reaction in the absence of inhibitor (I) divided by the total enzyme concentration (E).

In some embodiments, the anti-FXIIa antibody described herein may have a $Ki^{app}$ value of 1000, 900, 800, 700, 600, 500, 400, 300, 200, 100, 50, 40, 30, 20, 19, 18, 17, 16, 15, 14, 13, 12, 11, 10, 9, 8, 7, 6, 5 pM or less for the target antigen or antigen epitope. In some embodiments, the anti-FXIIa antibody may have a lower $Ki^{app}$ for a first target (e.g., FXIIa) relative to a second target (e.g., FXII). Differences in $Ki^{app}$ (e.g., for specificity or other comparisons) can be at least 1.5, 2, 3, 4, 5, 10, 15, 20, 37.5, 50, 70, 80, 91, 100, 500, 1000, 10,000 or $10^5$ fold. In some examples, the anti-FXIIa antibody inhibits a first antigen (e.g., a first protein in a first conformation or mimic thereof) better relative to a second antigen (e.g., the same first protein in a second conformation or mimic thereof; or a second protein). In some embodiments, any of the anti-FXIIa antibodies may be further affinity matured to reduce the $Ki^{app}$ of the antibody to the target antigen or antigenic epitope thereof.

The antibodies described herein can be murine, rat, human, or any other origin (including chimeric or humanized antibodies). Such antibodies are non-naturally occurring, i.e., would not be produced in an animal without human act (e.g., immunizing such an animal with a desired antigen or fragment thereof).

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In one example, the antibody used in the methods described herein is a humanized antibody. Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the anti-FXIIa antibodies described herein specifically bind to the corresponding target antigen or an epitope thereof. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (FXIIa) or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen. In some embodiments, the antibodies described herein specifically bind to FXIIa. In some embodiments, the antibodies described herein specifically bind to FXIIa and do not bind to FXII.

As used herein, the term "Factor XIIa" or "FXIIa" refers to the active form of Factor XII and the term "Factor XII" or "FXII" refers to the proenzyme or zymogen of Factor XII (inactive form). FXII is a single chain glycoprotein with a molecule weight of about 80 kD. Once activated, FXII is concerted into the active form, FXIIa, which contains two chains, the heavy chain (353 residues of the human FXIIa heavy chain) and the light chain (243 residues of the human FXIIa light chain), held by a disulfide bond. Human FXII is encoded by gene F12. The amino acid sequence of human FXII is well known in the art, e.g., GenBank Accession Number NP_000496.2.

In some embodiments, an anti-FXIIa antibody as described herein has a suitable binding affinity for the target antigen (e.g., FXIIa) or antigenic epitopes thereof. As used herein, "binding affinity" refers to the apparent association constant or $K_A$. The $K_A$ is the reciprocal of the dissociation constant ($K_D$). The anti-FXIIa antibody described herein may have a binding affinity ($K_D$) of at least $10^{-5}$, $10^{-6}$, $10^{-7}$, $10^{-8}$, $10^{-9}$, $10^{-10}$ M, or lower for the target antigen or antigenic epitope. An increased binding affinity corresponds to a decreased $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). In some embodiments, the anti-FXIIa antibodies described herein have a higher binding affinity (a higher $K_A$ or smaller $K_D$) to FXIIa as compared to the binding affinity to the zymogen FXII or another protein in the pKal signaling system. Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold. In some embodiments, any of the anti-FXIIa antibodies may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

[Bound]=[Free]/($K_d$+[Free])

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the anti-FXIIa antibody comprises a heavy chain comprising a heavy chain variable region that comprises a heavy chain CDR1, a heavy chain CDR2, and a heavy chain CDR3. In some instances, the heavy chain CDR3 region comprises the amino acid sequence of SEQ ID NO: 111, 112 or 113 (see Table 1). The heavy chain variable region of any of the anti-FXIIa antibodies described herein may further comprise a CDR1 region comprising the formula $X_1YX_3MX_5$ (SEQ ID NO: 117) as described herein, and/or a CDR2 region comprising the formula $X_1IX_3PSGX_7X_8TX_{10}YX_{12}DSVKG$, (SEQ ID NO: 118), which is also described herein. In some examples, the anti-FXIIa antibody comprises a heavy chain CDR1 region selected from SEQ ID NO: 41-73 and 121 (see Table 1) and/or a CDR2 region selected from SEQ ID NO: 74-110 and 122-124. In some specific examples, the heavy chain variable region of an anti-FXIIa antibody as described herein comprises the amino acid sequence of any of SEQ ID NOs:1-39.

Table 1 provides the amino acid sequences of the heavy chain CDRs for exemplary anti-FXIIa antibodies. Antibodies having the same heavy chain CDR1, CDR2, and CDR3 regions as those exemplary anti-FXIIa antibodies are also within the scope of the present disclosure.

TABLE 1

Heavy chain CDR sequences of anti-FXIIa antibodies

| Exemplary Antibody | CDR1 | CDR2 | CDR3 |
| --- | --- | --- | --- |
| M0191-E09 | WYSMH (SEQ ID NO: 41) | VIYPSGGKTRYADSVKG (SEQ ID NO: 74) | QRYRGPKYYYYMDV (SEQ ID NO: 111) |
| M0192-H11 | QYVMH (SEQ ID NO: 42) | SIWPSGGHTRYADSVKG (SEQ ID NO: 75) | QRYRGPKYYYYMDV (SEQ ID NO: 111) |
| M0184-F12 | WYVMH (SEQ ID NO: 43) | GIWPSGGRTKYADSVKG (SEQ ID NO: 76) | QRYRGPKYYYYMDV (SEQ ID NO: 111) |
| M0292-D07 | NYVMH (SEQ ID NO: 44) | SIWPSGGKTKYADSVKG (SEQ ID NO: 77) | QRYRGPKYYYYMDA (SEQ ID NO: 112) |
| M0182-D04 | MYTMN (SEQ ID NO: 45) | RIYPSGGKTLYADSVKG (SEQ ID NO: 78) | QRYRGPKYYYYMDV (SEQ ID NO: 111) |
| M0192-F07 | QYVMS (SEQ ID NO: 46) | RIYPSGGVTKYADSVKG (SEQ ID NO: 79) | QRYRGPKYYYYMDV (SEQ ID NO: 111) |
| M0183-C03 | WYNMH (SEQ ID NO: 47) | YISPSGGKTKYTDSVKG (SEQ ID NO: 80) | QRYRGPKYYYYMDV (SEQ ID NO: 111) |
| M0183-H08 | RYIMH (SEQ ID NO: 48) | SIYPSGGVTKYADSVKG (SEQ ID NO: 81) | QRYRGPKYYYYMDV (SEQ ID NO: 111) |
| M0183-D08 | RYIMG (SEQ ID NO: 49) | SIYPSGGVTRYADSVKG (SEQ ID NO: 82) | QRYRGPKYYYYMDV (SEQ ID NO: 111) |
| M0192-G03 | QYNMV (SEQ ID NO: 50) | RIWPSGGKTTYADSVKG (SEQ ID NO: 83) | QRYRGPKYYYYMDV (SEQ ID NO: 111) |
| M0310-C06 | RYVMV (SEQ ID NO: 51) | RIYPSGGMTQYADSVKG (SEQ ID NO: 84) | QRYRGPKYYYYMDV (SEQ ID NO: 111) |
| M0192-F01 | WYNMA (SEQ ID NO: 52) | RIYPSGGMTQYADSVKG (SEQ ID NO: 84) | QRYRGPKYYYYMDV (SEQ ID NO: 111) |
| M0191-A03 | QYIMH (SEQ ID NO: 53) | SIYPSGGNTKYADSVKG (SEQ ID NO: 85) | QRYRGPKYYYYMDV (SEQ ID NO: 111) |
| M0192-A01 | HYVMH (SEQ ID NO: 54) | SIYPSGGLTKYADSVKG (SEQ ID NO: 86) | QRYRGPKYYYYMDV (SEQ ID NO: 111) |

TABLE 1-continued

Heavy chain CDR sequences of anti-FXIIa antibodies

| Exemplary Antibody | CDR1 | CDR2 | CDR3 |
|---|---|---|---|
| M0191-H10 | WYTMH (SEQ ID NO: 55) | SIYPSGGFTRYADSVKG (SEQ ID NO: 87) | QRYRGPKYYYYMDV (SEQ ID NO: 111) |
| M0177-C12 | FYHMH (SEQ ID NO: 56) | RIVPSGGMTRYADSVKG (SEQ ID NO: 88) | QRYRGPKYYYYMDV (SEQ ID NO: 111) |
| M0184-B04 | FYSMH (SEQ ID NO: 57) | RIYPSGGVTKYADSVKG (SEQ ID NO: 89) | QRYRGPKYYYYMDV (SEQ ID NO: 111) |
| M0308-H03 | QYVMH (SEQ ID NO: 58) | SIWPSGGKTTYADSVKG (SEQ ID NO: 90) | QRYRGPKYYYYMDV (SEQ ID NO: 111) |
| M0192-D02 | QYVMH (SEQ ID NO: 58) | SIWPSGGFTKYADSVKG (SEQ ID NO: 91) | QRYRGPKYYYYMDV (SEQ ID NO: 111) |
| M0310-G07 | FYNMH (SEQ ID NO: 59) | SIYPSGGVTRYADSVKG (SEQ ID NO: 92) | QRYRGPKYYYYMDV (SEQ ID NO: 111) |
| M0192-F06 | WYVMH (SEQ ID NO: 43) | SIYPSGGKTSYADSVKG (SEQ ID NO: 93) | QRYRGPKYYYYMDV (SEQ ID NO: 111) |
| M0310-A04 | PYIMH (SEQ ID NO: 60) | VIYPSGSKTNYADSVKG (SEQ ID NO: 94) | QRYRGPKYYYYMDV (SEQ ID NO: 111) |
| M0310-F02 | RYTMR (SEQ ID NO: 61) | SIWPSGGMTRYADSVKG (SEQ ID NO: 95) | QRYRGPKYYYYMDV (SEQ ID NO: 111) |
| M0310-B09 | QYVMH (SEQ ID NO: 58) | SIYPSGGLTRYADSVKG (SEQ ID NO: 96) | QRYRGPKYYYYMDV (SEQ ID NO: 111) |
| M0310-G06 | WYIMG (SEQ ID NO: 62) | YIYPSGGNTRYADSVKG (SEQ ID NO: 97) | QRYRGPKYYYYMDV (SEQ ID NO: 111) |
| M0182-H01 | RYVMH (SEQ ID NO: 63) | SIWPSGGMTKYADSVKG (SEQ ID NO: 98) | QRYRGPKYYYYMDV (SEQ ID NO: 111) |
| M0178-A08 | FYIMG (SEQ ID NO: 64) | RIYPSGGATQYADSVKG (SEQ ID NO: 99) | QRYRGPKYYYYMDV (SEQ ID NO: 111) |
| M0184-D01 | FYVMG (SEQ ID NO: 65) | RIYPSGGLTQYADSVKG (SEQ ID NO: 100) | QRYRGPKYYYYMDV (SEQ ID NO: 111) |
| M0177-A06 | FYSMH (SEQ ID NO: 66) | RIYPSGGITSYADSVKG (SEQ ID NO: 101) | QRYRGPKYYYYMDV (SEQ ID NO: 111) |
| M0191-E04 | MYIMH (SEQ ID NO: 67) | SIYPSGGMTKYADSVKG (SEQ ID NO: 102) | QRYRGPKYYYYMDV (SEQ ID NO: 111) |
| M0191-H09 | MYVMH (SEQ ID NO: 68) | SIYPSGGLTKYADSVKG (SEQ ID NO: 103) | QRYRGPKYYYYMDV (SEQ ID NO: 111) |
| M0192-H04 | QYVMH (SEQ ID NO: 58) | RIYPSGGLTNYADSVKG (SEQ ID NO: 104) | QRYRGPKYYYYMDV (SEQ ID NO: 111) |
| M0192-A03 | WYVMQ (SEQ ID NO: 69) | SIYPSGGMTKYADSVKG (SEQ ID NO: 102) | QRYRGPKYYYYMDV (SEQ ID NO: 111) |
| M0310-G08 | WYIMG (SEQ ID NO: 62) | RIYPSGGSTHYADSVKG (SEQ ID NO: 105) | QRYRGPRYYYYIDA (SEQ ID NO: 113) |
| M0192-G05 | QYTMV (SEQ ID NO: 70) | RIYPSGGVTQYADSVKG (SEQ ID NO: 106) | QRYRGPKYYYYMDV (SEQ ID NO: 111) |
| M0183-B12 | WYVMY (SEQ ID NO: 71) | RIYPSGGITHYADSVKG (SEQ ID NO: 107) | QRYRGPKYYYYMDV (SEQ ID NO: 111) |
| M0308-F04 | FYVML (SEQ ID NO: 72) | SIWPSGGVTKYADSVKG (SEQ ID NO: 108) | QRYRGPKYYYYMDV (SEQ ID NO: 111) |
| M0182-B04 | WYVMQ (SEQ ID NO: 69) | YIYPSGGHTKYADSVKG (SEQ ID NO: 109) | QRYRGPKYYYYMDV (SEQ ID NO: 111) |
| M0310-F04 | RYSMN (SEQ ID NO: 73) | GIYPSGGKTKYADSVKG (SEQ ID NO: 110) | QRYRGPKYYYYMDV (SEQ ID NO: 111) |

TABLE 1-continued

Heavy chain CDR sequences of anti-FXIIa antibodies

| Exemplary Antibody | CDR1 | CDR2 | CDR3 |
|---|---|---|---|
| X211-A01 (DX-4012) | QYVMH (SEQ ID NO: 58) | SIWPSGGHTRYADSVKG (SEQ ID NO: 75) | QRYRGPKYYYYMDV (SEQ ID NO: 111) |

The heavy chain variable regions of the exemplary anti-FXIIa antibodies listed in Table 1 are provided below (CDR regions are boldfaced). In other embodiments, the HC CDR1 of the anti-FXIIa antibody can be QYSMH (SEQ ID NO:121), which may be in combination with HC CDR2 of SEQ ID NO:74 and/or HC CDR3 of SEQ ID NO:111. In yet other embodiments, the HC CDR2 of the anti-FXIIa antibody can be SIYPSGGKTRYADSVKG (SEQ ID NO:122), VIWPSGGKTRYADSVKG (SEQ ID NO:123), or VIYPSGGHTRYADSVKG (SEQ ID NO:124), which may be in combination with HC CDR1 of SEQ ID NO:41 and/or HC CDR3 of SEQ ID NO:111. In still another embodiment, the HC CDR2 of the anti-FXIIa antibody can be SIWPSGGHTRYADSVHG (SEQ ID NO:127), which may be in combination with HC CDR1 of SEQ ID NO:58 and/or HC CDR3 of SEQ ID NO:111.

```
Heavy chain variable region sequence of M0191-E09 (SEQ ID NO: 1):
EVQLLESGGGLVQPGGSLRLSCAASGFTFSWYSMHWVRQAPGKGLEWVSVIYPSGGKTRYADSVKGRFTISRD
NSKNTLYLQMNSLRAEDTAVYYCTRQRYRGPKYYYYMDVWGKGTTVTVSS Heavy chain variable region sequence of M0192-H11 (SEQ ID NO: 2):
EVQLLESGGGLVQPGGSLRLSCAASGFTFSQYVMHWVRQAPGKGLEWVSSIWPSGGHTRYADSVKGRFTISRD
NSKNTLYLQMNSLRAEDTAVYYCTRQRYRGPKYYYYMDVWGKGTTVTVSS Heavy chain variable region sequence of M0184-F12 (SEQ ID NO: 3):
EVQLLESGGGLVQPGGSLRLSCAASGFTFSWYVMHWVRQAPGKGLEWVSGIWPSGGRTKYADSVKGRFTISRD
NSKNTLYLQMNSLRAEDTAVYYCTRQRYRGPKYYYYMDVWGKGTTVTVSS Heavy chain variable region sequence of M0292-D07 (SEQ ID NO: 4):
EVQLLESGGGLVQPGGSLRLSCAASGFTFSNYVMHWVRQAPGKGLEWVSSIWPSGGKTKYADSVKGRFTISRD
NSKNTLYLQMNSLRAEDTAVYYCTRQRYRGPKYYYYMDAWGQGTTVTVSS Heavy chain variable region sequence of M0182-D04 (SEQ ID NO: 5):
EVQLLESGGGLVQPGGSLRLSCAASGFTFSMYTMNWVRQAPGKGLEWVSRIYPSGGKTLYADSVKGRFTISRD
NSKNTLYLQMNSLRAEDTAVYYCTRQRYRGPKYYYYMDVWGKGTTVTVSS Heavy chain variable region sequence of M192-F07 (SEQ ID NO: 6):
EVQLLESGGGLVQPGGSLRLSCAASGFTFSQYVMSWVRQAPGKGLEWVSRIYPSGGVTKYADSVKGRFTISRD
NSKNTLYLQMNSLRAEDTAVYYCTRQRYRGPKYYYYMDVWGKGTTVTVSS Heavy chain variable region sequence of M0183-C03 (SEQ ID NO: 7):
EVQLLESGGGLVQPGGSLRLSCAASGFTFSWYNMHWVRQAPGKGLEWVSYISPSGGKTKYTDSVKGRFTISRD
NSKNTLYLQMNSLRAEDTAVYYCTRQRYRGPKYYYYMDVWGKGTTVTVSS Heavy chain variable region sequence of M0183-H08 (SEQ ID NO: 8):
EVQLLESGGGLVQPGGSLRLSCAASGFTFSRYIMHWVRQAPGKGLEWVSSIYPSGGVTKYADSVKGRFTISRD
NSKNTLYLQMNSLRAEDTAVYYCTRQRYRGPKYYYYMDVWGKGTTVTVSS Heavy chain variable region sequence of M0183-D08 (SEQ ID NO: 9):
EVQLLESGGGLVQPGGSLRLSCAASGFTFSRYIMGWVRQAPGKGLEWVSSIYPSGGVTRYADSVKGRFTISRD
NSKNTLYLQMNSLRAEDTAVYYCTRQRYRGPKYYYYMDVWGKGTTVTVSS Heavy chain variable region sequence of M0192-G03 (SEQ ID NO: 10):
EVQLLESGGGLVQPGGSLRLSCAASGFTFSQYNMVWVRQAPGKGLEWVSRIWPSGGKTTYADSVKGRFTISRD
NSKNTLYLQMNSLRAEDTAVYYCTRQRYRGPKYYYYMDVWGKGTTVTVSS Heavy chain variable region sequence of M0310-C06 (SEQ ID NO: 11):
EVQLLESGGGLVQPGGSLRLSCAASGFTFSRYVMWWVRQAPGKGLEWVSRIYPSGGMTQYADSVKGRFTISRD
NSKNTLYLQMNSLRAEDTAVYYCTRQRYRGPKYYYYMDVWGKGTTVTVSS Heavy chain variable region sequence of M0192-F01 (SEQ ID NO: 12):
EVQLLESGGGLVQPGGSLRLSCAASGFTFSWYNMAWVRQAPGKGLEWVSRIYPSGGMTQYADSVKGRFTISRD
NSKNTLYLQMNSLRAEDTAVYYCTRQRYRGPKYYYYMDVWGKGTTVTVSS Heavy chain variable region sequence of M0191-A03 (SEQ ID NO: 13):
EVQLLESGGGLVQPGGSLRLSCAASGFTFSQYIMHWVRQAPGKGLEWVSSIYPSGGNTKYADSVKGRFTISRD
NSKNTLYLQMNSLRAEDTAVYYCTRQRYRGPKYYYYMDVWGKGTTVTVSS Heavy chain variable region sequence of M0192-A01 (SEQ ID NO: 14):
EVQLLESGGGLVQPGGSLRLSCAASGFTFSHYVMHWVRQAPGKGLEWVSSIYPSGGLTKYADSVKGRFTISRD
NSKNTLYLQMNSLRAEDTAVYYCTRQRYRGPKYYYYMDVWGKGTTVTVSS
```

-continued

Heavy chain variable region sequence of M0191-H10 (SEQ ID NO: 15):
EVQLLESGGGLVQPGGSLRLSCAASGFTFSWYTMHWVRQAPGKGLEWVSSIYPSGGFTRYADSVKGRFTISRD
NSKNTLYLQMNSLRAEDTAVYYCTRQRYRGPKYYYYMDVWGKGTTVTVSS Heavy chain variable region sequence of M0177-C12 (SEQ ID NO: 16):
EVQLLESGGGLVQPGGSLRLSCAASGFTFSFYHMHWVRQAPGKGLEWVSRIVPSGGMTRYADSVKGRFTISRD
NSKNTLYLQMNSLRAEDTAVYYCTRQRYRGPKYYYYMDVWGKGTTVTVSS Heavy chain variable region sequence of M0184-B04 (SEQ ID NO: 17):
EVQLLESGGGLVQPGGSLRLSCAASGFTFSFYSMHWVRQAPGKGLEWVSRIYPSGGVTKYADSVKGRFTISRD
NSKNTLYLQMNSLRAEDTAVYYCTRQRYRGPKYYYYMDVWGKGTTVTVSS Heavy chain variable region sequence of M0308-H03 (SEQ ID NO: 18):
EVQLLESGGGLVQPGGSLRLSCAASGFTFSQYVMHWVRQAPGKGLEWVSSIWPSGGKTTYADSVKGRFTISRD
NSKNTLYLQMNSLRAEDTAVYYCTRQRYRGPKYYYYMDVWGKGTTVTVSS Heavy chain variable region sequence of M0192-D02 (SEQ ID NO: 19):
EVQLLESGGGLVQPGGSLRLSCAASGFTFSQYVMHWVRQAPGKGLEWVSSIWPSGGFTKYADSVKGRFTISRD
NSKNTLYLQMNSLRAEDTAVYYCTRQRYRGPKYYYYMDVWGKGTTVTVSS Heavy chain variable region sequence of M0310-G07 (SEQ ID NO: 20):
EVQLLESGGGLVQPGGSLRLSCAASGFTFSFYNMHWVRQAPGKGLEWVSSIYPSGGVTRYADSVKGRFTISRD
NSKNTLYLQMNSLRAEDTAVYYCTRQRYRGPKYYYYMDVWGKGTTVTVSS Heavy chain variable region sequence of M0192-F06 (SEQ ID NO: 21):
EVQLLESGGGLVQPGGSLRLSCAASGFTFSWYVMHWVRQAPGKGLEWVSSIYPSGGKTSYADSVKGRFTISRD
NSKNTLYLQMNSLRAEDTAVYYCTRQRYRGPKYYYYMDVWGKGTTVTVSS Heavy chain variable region sequence of M0310-A04 (SEQ ID NO: 22):
EVQLLESGGGLVQPGGSLRLSCAASGFTFSPYIMHWVRQAPGKGLEWVSVIYPSGSKTNYADSVKGRFTISRD
NSKNTLYLQMNSLRAEDTAVYYCTRQRYRGPKYYYYMDVWGKGTTVTVSS Heavy chain variable region sequence of M0310-F02 (SEQ ID NO: 23):
EVQLLESGGGLVQPGGSLRLSCAASGFTFSRYTMRWVRQAPGKGLEWVSSIWPSGGMTRYADSVKGRFTISRD
NSKNTLYLQMNSLRAEDTAVYYCTRQRYRGPKYYYYMDVWGQGTTVTVSS Heavy chain variable region sequence of M0310-B09 (SEQ ID NO: 24):
EVQLLESGGGLVQPGGSLRLSCAASGFTFSQYVMHWVRQAPGKGLEWVSSIYPSGGLTRYADSVKGRFTISRD
NSKNTLYLQMNSLRAEDTAVYYCTRQRYRGPKYYYYMDVWGQGTTVTVSS Heavy chain variable region sequence of M0310-G06 (SEQ ID NO: 25):
EVQLLESGGGLVQPGGSLRLSCAASGFTFSWYIMGWVRQAPGKGLEWVSYIYPSGGNTRYADSVKGRFTISRD
NSKNTLYLQMNSLRAEDTAVYYCTRQRYRGPKYYYYMDVWGKGTTVTVSS Heavy chain variable region sequence of M0182-H01 (SEQ ID NO: 26):
EVQLLESGGGLVQPGGSLRLSCAASGFTFSRYVMHWVRQAPGKGLEWVSSIWPSGGMTKYADSVKGRFTISRD
NSKNTLYLQMNSLRAEDTAVYYCTRQRYRGPKYYYYMDVWGKGTTVTVSS Heavy chain variable region sequence of M0178-A08 (SEQ ID NO: 27):
EVQLLESGGGLVQPGGSLRLSCAASGFTFSFYIMGWVRQAPGKGLEWVSRIYPSGGATQYADSVKGRFTISRD
NSKNTLYLQMNSLRAEDTAVYYCTRQRYRGPKYYYYMDVWGKGTTVTVSS Heavy chain variable region sequence of M0184-D01 (SEQ ID NO: 28):
EVQLLESGGGLVQPGGSLRLSCAASGFTFSFYVMGWVRQAPGKGLEWVSRIYPSGGLTQYADSVKGRFTISRD
NSKNTLYLQMNSLRAEDTAVYYCTRQRYRGPKYYYYMDVWGKGTTVTVSS Heavy chain variable region sequence of M0177-A06 (SEQ ID NO: 29):
EVQLLESGGGLVQPGGSLRLSCAASGFTFSFYSMHWVRQAPGKGLEWVSRIYPSGGITSYADSVKGRFTISRD
NSKNTLYLQMNSLRAEDTAVYYCTRQRYRGPKYYYYMDVWGKGTTVTVSS Heavy chain variable region sequence of M0191-E04 (SEQ ID NO: 30):
EVQLLESGGGLVQPGGSLRLSCAASGFTFSMYIMHWVRQAPGKGLEWVSSIYPSGGMTKYADSVKGRFTISRD
NSKNTLYLQMNSLRAEDTAVYYCTRQRYRGPKYYYYMDVWGKGTTVTVSS Heavy chain variable region sequence of M0191-H09 (SEQ ID NO: 31):
EVQLLESGGGLVQPGGSLRLSCAASGFTFSMYVMHWVRQAPGKGLEWVSSIYPSGGLTKYADSVKGRFTISRD
NSKNTLYLQMNSLRAEDTAVYYCTRQRYRGPKYYYYMDVWGKGTTVTVSS Heavy chain variable region sequence of M0192-H04 (SEQ ID NO: 32):
EVQLLESGGGLVQPGGSLRLSCAASGFTFSQYVMHWVRQAPGKGLEWVSRIYPSGGLTNYADSVKGRFTISRD
NSKNTLYLQMNSLRAEDTAVYYCTRQRYRGPKYYYYMDVWGKGTTVTVSS Heavy chain variable region sequence of M0192-A03 (SEQ ID NO: 33):
EVQLLESGGGLVQPGGSLRLSCAASGFTFSWYVMQWVRQAPGKGLEWVSSIYPSGGMTKYADSVKGRFTISRD
NSKNTLYLQMNSLRAEDTAVYYCTRQRYRGPKYYYYMDVWGKGTTVTVSS Heavy chain variable region sequence of M0310-G08 (SEQ ID NO: 34):
EVQLLESGGGLVQPGGSLRLSCAASGFTFSWYIMGWVRQAPGKGLEWVSRIYPSGGSTHYADSVKGRFTISRD
NSKNTLYLQMNSLRAEDTAVYYCTRQRYRGPRYYYYIDAWGQGTTVTVSS -continued
Heavy chain variable region sequence of M0192-G05 (SEQ ID NO: 35):
EVQLLESGGGLVQPGGSLRLSCAASGFTFSQYTMVWVRQAPGKGLEWVSRIYPSGGVTQYADSVKGRFTISRD
NSKNTLYLQMNSLRAEDTAVYYCTRQRYRGPKYYYYMDVWGKGTTVTVSS Heavy chain variable region sequence of M0183-B12 (SEQ ID NO: 36):
EVQLLESGGGLVQPGGSLRLSCAASGFTFSWYVMYWVRQAPGKGLEWVSRIYPSGGITHYADSVKGRFTISRD
NSKNTLYLQMNSLRAEDTAVYYCTRQRYRGPKYYYYMDVWGKGTTVTVSS Heavy chain variable region sequence of M0308-F04 (SEQ ID NO: 37):
EVQLLESGGGLVQPGGSLRLSCAASGFTFSFYVMLWVRQAPGKGLEWVSSIWPSGGVTKYADSVKGRFTISRD
NSKNTLYLQMNSLRAEDTAVYYCTRQRYRGPKYYYYMDVWGKGTTVTVSS Heavy chain variable region sequence of M0182-B04 (SEQ ID NO: 38):
EVQLLESGGGLVQPGGSLRLSCAASGFTFSWYVMQWVRQAPGKGLEWVSYIYPSGGHTKYADSVKGRFTISRD
NSKNTLYLQMNSLRAEDTAVYYCTRQRYRGPKYYYYMDVWGKGTTVTVSS Heavy chain variable region sequence of M0310-F04 (SEQ ID NO: 39):
EVQLLESGGGLVQPGGSLRLSCAASGFTFSRYSMNWVRQAPGKGLEWVSGIYPSGGKTKYADSVKGRFTISRD
NSKNTLYLQMNSLRAEDTAVYYCTRQRYRGPKYYYYMDVWGKGTTVTVSS Heavy chain variable region sequence of X211-A01 (SEQ ID NO: 125)
EVQLLESGGGLVQPGGSLRLSCAASGFTFSQYVMHWVRQAPGKGLEWVSSIWPSGGHTRYADSVKGRFTISRD
NSKNTLYLQMNSLRAEDTAVYYCTRQRYRGPKYYYYMDVWGKGTTVTVSS The present disclosure also provides germlined variants of any of the exemplary anti-FXIIa antibodies disclosed herein. A germlined variant contains one or more mutations in the framework regions as relative to its parent antibody towards the corresponding germline sequence. To make a germline variant, the heavy or light chain variable region sequence of the parent antibody or a portion thereof (e.g., a framework sequence) can be used as a query against an antibody germline sequence database (e.g., www.bioinfo.org.uk/abs/, www.vbase2.org, or www.imgt.org) to identify the corresponding germline sequence used by the parent antibody and amino acid residue variations in one or more of the framework regions between the germline sequence and the parent antibody. One or more amino acid substitutions can then be introduced into the parent antibody based on the germline sequence to produce a germlined variant. As examples, clone X211-A01 (DX-4012) is a germline variant of clone M192-H11 As described herein, the anti-FXIIa antibody can be in any antibody form, including, but not limited to, intact (i.e., full-length) antibodies, antigen-binding fragments thereof (such as Fab, Fab', F(ab')2, Fv), and single chain antibodies.

In some embodiments, the heavy chain of any of the anti-FXIIa antibodies as described herein may further comprise a heavy chain constant region (CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain). One exemplary human heavy chain constant region is provided below (SEQ ID NO:119):

```
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRVEP KSCDKTHTCP PCPAPELLGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSREE
```

-continued
```
MTKNQVSLTC LVKGFYPSDI AVEWESNGQP ENNYKTTPPV

LDSDGSFFLY SKLTVDKSRW QQGNVFSCSV MHEALHNHYT

QKSLSLSPG
```

The boldfaced/underlined residues represent those where mutations can be introduced to enhance FcRn binding and then serum half-life.

In some embodiments, the anti-FXIIa antibody comprises the heavy chain constant region of SEQ ID NO:119. Alternatively, the heavy chain constant region of the antibodies described herein may comprise a single domain (e.g., CH1, CH2, or CH3) or a combination of any of the single domains, of a constant region (e.g., SEQ ID NO:119).

When needed, the anti-FXIIa antibody as described herein may comprise a modified constant region. For example, it may comprise a modified constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

In some embodiments, the heavy chain constant region used in the anti-FXIIa antibodies described herein may comprise mutations (e.g., amino acid residue substitutions) to enhance a desired characteristic of the antibody, for example, increasing the binding activity to the neonatal Fc receptor (FcRn) and thus the serum half-life of the antibodies. It was known that binding to FcRn is critical for maintaining antibody homeostasis and regulating the serum half-life of antibodies. One or more (e.g., 1, 2, 3, 4, 5, or more) mutations (e.g., amino acid residue substitutions) may be introduced into the constant region at suitable positions (e.g., in CH2 region) to enhance FcRn binding and enhance the half-life of the antibody. Such mutations may be at a position(s) corresponding to 145, 147, and/or 149 of SEQ ID NO:119 (corresponding to positions 252, 254, and 256 based on the numbering system reported in Kabat et al., 1991, Sequences of Proteins of Immunological Interest, U.S. Public Health Service, National Institutes of Health, Washington, D.C.). See also Dall'Acqua et al., J.B.C., 2006, 281: 23514-23524; Robbie et al., Antimicrob. Agents Chemother, 2013, 57(12):6147; and Dall'Acqua et al., J. Immunol. 2002 169:5171-5180. If a constant region other than SEQ ID NO:119 is used, the positions where mutations may be introduced can be determined either by aligning the amino acid sequence of that constant region with SEQ ID NO:119 to identify the positions corresponding to a position of interest (e.g., positions 145, 147, or 149 in SEQ ID NO:119). Alternatively, such positions can be determined by a well-recognized numbering system such as the Kabat numbering system noted above.

In some examples, a substitution mutation is introduced at the amino acid residue (e.g., a methionine residue) at position 252 (position 145 of SEQ ID NO:119) of a heavy chain constant region, e.g., M→Y substitution. In some examples, a substitution mutation is introduced at position 254 (position 147 of SEQ ID NO:119) of a heavy chain constant region, e.g., S→T substitution. In some examples, a substitution mutation is introduced at position 256 (position 149 of SEQ ID NO:119) of a heavy chain constant region, e.g., T→E. In some examples, the threonine at position 256 is mutated to a glutamic acid residue. When desired, multiple mutations (e.g., amino acid substitutions) may be introduced into a heavy chain constant region, e.g., any combination of the above-noted substitutions. In a specific example, a modified heavy chain constant region used in any of the anti-FXIIa antibodies can contain amino acid substitutions at positions 252, 254, and 256 (e.g., M252Y, S254T, and T256E; also known as a YTE variant). See, e.g., Dall'Acqua et al., J.B.C., 2006, 281:23514-23524; Robbie et al., Antimicrob. Agents Chemother, 2013, 57(12):6147; and Dall'Acqua et al., J. Immunol. 2002 169:5171-5180. The amino acid sequence below (SEQ ID NO:120) represents an exemplary modified heavy chain constant region having enhanced FcRn binding activity and thus serum half-life:

```
Exemplary heavy chain constant region sequence
of a YTE variant (SEQ ID NO: 120):
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRVEP KSCDKTHTCP PCPAPELLGG

PSVFLFPPKP KDTLYITREP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSREE

MTKNQVSLTC LVKGFYPSDI AVEWESNGQP ENNYKTTPPV

LDSDGSFFLY SKLTVDKSRW QQGNVFSCSV MHEALHNHYT

QKSLSLSPG
```

Amino acid residues that are mutated in SEQ ID NO: 120 relative to SEQ ID NO: 119 are shown in boldface.

Any of the anti-FXIIa antibodies described herein may further comprise a light chain that includes a light chain variable region and optionally, a light chain constant region, which can be any CL known in the art. In some examples, the CL is a kappa light chain. In other examples, the CL is a lambda light chain. Antibody heavy and light chain constant regions are well known in the art, e.g., those provided in the IMGT database (www.imgt.org) or at www.vbase2.org/vbstat.php., both of which are incorporated by reference herein.

The anti-FXIIa antibody described herein may comprise a light chain variable region that comprises a light chain CDR3 set forth as SEQ ID NO: 116 (see Table 2). In some embodiments, the light chain variable region of the anti-FXIIa antibody may further comprise a light chain CDR1 region set forth as SEQ ID NO: 114 (see Table 2) and/or a light chain CDR2 region set forth as SEQ ID NO: 115 (see Table 2). For example, the anti-FXIIa antibody light chain variable region may comprise the light chain CDR1 of SEQ ID NO:114, the light chain CDR2 of SEQ ID NO:115, and the light chain CDR3 of SEQ ID NO: 116. In one example, the light chain variable region comprises the amino acid sequence of SEQ ID NO: 40. Alternatively, the light chain variable region is a germline variant of SEQ ID NO:40, which may contain one or more mutations in one or more frameworks toward the corresponding germline sequence. The corresponding germline sequence can be identified by methods known in the art and those described herein.

An exemplary light chain variable region for anti-FXIIa antibodies is provided below (CDR regions are boldfaced).

```
Exemplary Light chain variable region for
anti-FXIIa antibodies (SEQ ID NO: 40):
DIQMTQSPLSLPVTPGEPASISCRSSQSLLHSNGYNYLDWYLQK

PGQSPQLLIYLGSNRASGVPDRFSGSGSGTDFTLKISRVEAEDV

GVYYCMQALQTPWTFGQGTKVEIK

Example Light chain variable region for
anti-FXIIa antibodies
                                 (SEQ ID NO: 126)
DIVMTQSPLSLPVTPGEPASISCRSSQSLLHSNGYNYLDWYLQK

PGQSPQLLIYLGSNRASGVPDRFSGSGSGTDFTLKISRVEAEDV

GVYYCMQALQTPWTFGQGTKVEIK
```

TABLE 2

Light chain CDR sequences of anti-FXIIa antibodies

|  | CDR1 | CDR2 | CD3 |
| --- | --- | --- | --- |
| Exemplary antibody | RSSQSLLH SNGYNYLD (SEQ ID NO: 114) | LGSNRAS (SEQ ID NO: 115) | MQALQTPWT (SEQ ID NO: 116) |

In some embodiments, the anti-FXIIa antibody described herein comprises a heavy chain variable region comprising the amino acid sequence of any of SEQ ID NO: 1-39; and a light chain variable region comprising the amino acid sequence of SEQ ID NO: 40. In other embodiments, the anti-FXIIa antibody described herein (e.g., X211-A01; aka DX-4012) comprises a heavy chain variable region comprising the amino acid sequence of SEQ ID NO:125 and a light chain variable region comprising the amino acid sequence of SEQ ID NO:126.

Also within the scope of the present disclosure are functional variants of any of the exemplary anti-FXIIa antibodies as disclosed herein (e.g., the 44 antibodies clones described above). In some examples, the anti-FXIIa antibody is a functional variant of an antibody comprising a heavy chain variable region provided by any one of SEQ ID NO: 1-39,and a light chain variable region provided by SEQ ID NO: 40. A functional variant can comprise up to 5 (e.g., 4, 3, 2, or 1) amino acid residue variations in one or more of the CDR regions of the antibody and binds the same epitope of FXIIa with substantially similar affinity (e.g., having a $K_D$ value in the same order). In one example, the amino acid residue variations are conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the anti-FXIIa antibody comprises heavy chain CDRs that are at least 80% (e.g., 85%, 90%, 95%, or 98%) identical to any one of the heavy chain CDR sequence provided by SEQ ID NO: 41-113,SEQ ID NO: 121-124, and SEQ ID NO: 127 and/or light chain CDR sequences that are at least 80% (e.g., 85%, 90%, 95%, or 98%) identical to at least one of the corresponding light chain CDRs provided by SEQ ID NO: 114-116. In some embodiments, the anti-FXIIa antibody comprises a heavy chain variable region that is at least 80% (e.g., 85%, 90%, 95%, or 98%) identical to the heavy chain variable region of any of SEQ ID NO: 1-39 and/or light chain variable region that is at least 80% (e.g., 85%, 90%, 95%, or 98%) identical to the light chain variable region provided by SEQ ID NO:40.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NB LAST) can be used.

In addition, the anti-FXIIa antibody can include one or more other residues that are identified based on the crystal structures discussed in Example 5 herein as being involved in interacting with the C chain of FXIIa. These residues can be located in the VH or the VL chain. Examples include T28, S30, Q31, W52, P53, S54, G55, G56, H57, R59, N74, R100, Y101, R102, G103, P104, K105, Y106, Y107, and Y108 in the heavy chain variable region, and H31, N33, Y35, Y54, L55, N58, and T99 in the light chain variable region.

Also provided herein are antibodies that target specific residues in FXIIa. The antibody can preferentially bind to FXIIa but not bind to FXII. In some embodiments, the antibody that specifically binds to FXIIa interacts with one or more of the residues (e.g., at least 3, 5, 8, 10, 15, 20, 25, 30, 35, 40 or 45) of the C chain of FXIIa, including L390, Y391, W392, G393, H394, S395, F396, C397, H412, C413, L414, Q415, D416, R432, N433, V456, Y458, H507, F509, E510, G511, A512, E513, Y515, D557, A558, C559, Q560, G561, D562, S563, I584, S585, W586, G587, S588, G589, C590, G591, D592, and G597. These residues are identified as interacting with one or more residues in of the heavy chain variable region and the light chain variable region of the anti-FXIIa antibody, according to the crystal structures described in Example 5 below.

The amino acid sequence (SEQ ID NO:128) of an exemplary human FXIIa is provided below and the above noted residues are highlighted in boldface:

```
  1  mrallllgfl lvslestlsi ppweapkehk ykaeehtvvl tvtgepchfp fqyhrglyhk 61  cthkgrpgpq pwcattpnfd qdqrwgycle pkkvkdhcsk hspcqkggtc vnmpsgphcl 121  cpqhltgnhc gkekcfepql lrffhkneiw yrteqaavar cqckgpdahc qrlasqacrt 181  npclhggrcl eveghrlchc pvgytgafcd vdtkascydg rglsyrglar ttlsgapcqp 241  waseatyrnv taegarnwgl gghafcrnpd ndirpwcfvl nrdrlsweyc dlaqcqtptq 301  aapptpvspr lhvplmpaqp appkpqpttr tppqsqtpga lpakreqpps ltrngplscg 361  qrlrkslssm trvvgglval rgahpyiaal ywghsfcags liapcwvlta ahclqdrpap 421  edltvvlgge rrnhscepcq tlavrsyrlh eafspvsyqh dlallrlqed adgscallsp 481  yvqpvclpsg aarpsettlc qvagwghqfe gaeeyasflq eaqvpflsle rcsapdvhgs 541  silpgmlcag fleggtdacq gdsggplvce dqaaerrltl qgiiswgsgc gdrnkpgvyt 601  dvayylawir ehtvs
```

Other exemplary FXIIa sequences can include human, mouse, or rat FXIIa sequences, a sequence that is 80%, 85%, 90%, 95%, 96%, 97%, 98%, or 99% identical to one of these sequences, or a fragment thereof.

Interacting means that the distance between two residues in a complex formed by two binding partners is lower than a predetermined value, e.g., <6 Å, <4 Å, or <2 Å. For example, an interacting residue in one binding partner can have has at least 1 atom within a given threshold (e.g., <6 Å, <4 Å, or <2 Å) of at least 1 atom from a residue of the other binding partner on the complexed structure. Interacting does not require actual binding. Interacting residues are suggested as involved in antibody recognition.

In some embodiments, the antibodies described herein bind human active FXIIa at an epitope comprising one or more of the residues listed above. An "epitope" refers to the site on a target compound that is bound by an antibody such as a Fab or full length antibody. An epitope can be linear, which is typically 6-15 aa in length. Alternatively, the epitope can be conformational.

In some examples, the antibody that specifically binds to FXIIa described herein binds an epitope that comprises the following segments of SEQ ID NO: 128: residues 390-397, residues 412-416, residues 432-433, residues 456-458, residues 507-515, residues 557-563, and/or residues 584-592.

Preparation of Anti-FXIIa Antibodies

Antibodies capable of binding FXIIa as described herein can be made by any method known in the art. See, for example, Harlow and Lane, (1998) Antibodies: A Laboratory Manual, Cold Spring Harbor Laboratory, New York.

In some embodiments, antibodies specific to a target antigen (e.g., FXIIa or the catalytic domain thereof) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-FXIIa monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the FXIIa activity. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of FXIIa. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455, and. Alternatively, the phage display technology (McCafferty et al., (1990) Nature 348: 552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., Proc. Natl. Acad. Sci. USA, 86:10029-10033 (1989). In one example, variable regions of VH and VL of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human VH and VL chains having amino acid sequences that are homologous to those of the parent non-human antibody are identified from any antibody gene database using the parent VH and VL sequences as search queries. Human VH and VL acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704, 692) can be adapted to produce a phage or yeast scFv library and scFv clones specific to a FXIIa can be identified from the library following routine procedures. Positive clones can be subjected to further screening to identify those that inhibit FXIIa activity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the FXIIa polypeptide have been replaced (swapped) with sequences from a closely related, but antigenically distinct protein (such as another member of the neurotrophin protein family). By assessing binding of the antibody to the mutant FXIIa, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

In some examples, an anti-FXIIa antibody is prepared by recombinant technology as exemplified below.

Nucleic acids encoding the heavy and light chain of an anti-FXIIa antibody as described herein can be cloned into one expression vector, each nucleotide sequence being in operable linkage to a suitable promoter. In one example, each of the nucleotide sequences encoding the heavy chain and light chain is in operable linkage to a distinct prompter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy). One particular advantage of this tetracycline inducible switch is that it does not require the use of a tetracycline repressor-mammalian cells transactivator or repressor fusion protein, which in some instances can be toxic to cells (Gossen et al., Natl. Acad. Sci. USA, 89:5547-5551 (1992); Shockett et al., Proc. Natl. Acad. Sci. USA, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes); versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-FXIIa antibody, as also described herein. The recombinant expression vector can be introduced into a suitable host cell (e.g., a dhfr− CHO cell) by a conventional method, e.g., calcium phosphate-mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-FXIIa antibody and the other encoding the light chain of the anti-FXIIa antibody. Both of the two recombinant expression vectors can be introduced into a suitable host cell (e.g., dhfr− CHO cell) by a conventional method, e.g., calcium phosphate-mediated transfection. Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-FXIIa antibody as described herein, vectors (e.g., expression vectors) containing such; and host cells comprising the vectors are within the scope of the present disclosure.

Pharmaceutical Compositions

The antibodies, as well as the encoding nucleic acids or nucleic acid sets, vectors comprising such, or host cells comprising the vectors, as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some examples, the pharmaceutical composition described herein comprises liposomes containing the antibodies (or the encoding nucleic acids) which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies, or the encoding nucleic acid(s), may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0.

The emulsion compositions can be those prepared by mixing an antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Methods of Treatment

Any of the antibodies, as well as the encoding nucleic acids or nucleic acid sets, vectors comprising such, or host cells comprising the vectors, described herein are useful for treating a disease or disorder associated with aberrant contact system activation, including diseases associated with contact system activation, diseases associated with aberrant contact system activation (e.g., HAE) or ocular diseases.

To practice the method disclosed herein, an effective amount of the pharmaceutical composition described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a target disease/disorder, such as hereditary angioedema (HAE), thrombosis, or ocular diseases. A subject having a target disease or disorder can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors for that disease/disorder.

The methods and compositions described herein may be used to treat any disease or disorder associated with contact system activation and/or pKal signaling pathways. In some embodiments, the target disease is thrombosis, including thrombosis associated with atrial fibrillation, DVT, pulmonary embolism, stroke, or other arterial or venous thrombotic events. Thrombosis (e.g., venous thrombosis or arterial thrombosis) refers to the formation of blood clots inside a blood vessel, which may obstruct the flow of blood through the circulation system. Subjects having or at risk for thrombosis can be identified by routine medical procedures.

In other embodiments, the disease that can be treated by the anti-FXIIa antibodies described herein can be a disease associated with the kallikrein system (e.g., the pKal system), including, but not limited to, macular edema, diabetic retinopathy, hypertensive retinopathy, age-related macular degeneration, and retinal vein occlusions. Examples of diseases or disorders associated with the contact activation system include, without limitation, rheumatoid arthritis, osteoarthritis, psoriatic arthritis, psoriasis, systemic lupus erythematosus, systemic lupus erythematosus nephritis, systemic mastocytosis, gout, intestinal bowel disease, oral mucositis, neuropathic pain, inflammatory pain, spinal stenosis-degenerative spine disease, arterial or venous thrombosis, post-operative ileus, aortic aneurysm, vasculitis, edema, acquired angioedema, idiopathic angioedema, anaphylasxis, idiopathic anaphylaxis, cerebral edema, pulmonary embolism, stroke, clotting on ventricular assistance devices or stents, clotting associated with the use of indwelling catheters or peripherally inserted central catheters, clotting associated with the use of an extracorporeal membrane oxygenation device, clotting associated with the use of a graft or fistula for dialysis, head trauma or peri-tumor brain edema, sepsis, acute middle cerebral artery (MCA), ischemic event (stroke), restenosis (e.g., after angioplasty), or burn injury.

In some embodiments, the disease that can be treated with the anti-FXIIa antibodies described herein is an ocular disease associated with contact activation system, including, but not limited to, macular edema, diabetic retinopathy, hypertensive retinopathy, age-related macular degeneration, and retinal vein occlusions.

In one example, the disease or condition that involves the contact system activation is hereditary angioedema (HAE). Hereditary angioedema (HAE) is also known as "Quincke edema," C1 esterase inhibitor deficiency, C1 inhibitor deficiency, and hereditary angioneurotic edema (HANE). HAE is characterized by recurrent episodes of severe swelling (angioedema), which can affect, e.g., the limbs, face, genitals, gastrointestinal tract, and airway. Symptoms of HAE include, e.g., swelling in the arms, legs, lips, eyes, tongue, and/or throat; airway blockage that can involve throat swelling and sudden hoarseness; repeat episodes of abdominal cramping without obvious cause; and/or swelling of the intestines, which can be severe and can lead to abdominal cramping, vomiting, dehydration, diarrhea, pain, and/or shock. About one-third of individuals with this HAE develop a non-itchy rash called erythema marginatum during an attack.

Swelling of the airway can be life threatening and causes death in some patients. Mortality rates are estimated at 15-33%. HAE leads to about 15,000-30,000 emergency department visits per year.

Trauma or stress, e.g., dental procedures, sickness (e.g., viral illnesses such as colds and the flu), menstruation, and surgery can trigger an attack of angioedema. To prevent acute attacks of HAE, patients can attempt to avoid specific stimuli that have previously caused attacks. However, in many cases, an attack occurs without a known trigger. Typically, HAE symptoms first appear in childhood and worsen during puberty. On average, untreated individuals have an attack every 1 to 2 weeks, and most episodes last for about 3 to 4 days (ghr.nlm.nih.gov/condition/hereditary-angioedema). The frequency and duration of attacks vary greatly among people with hereditary angioedema, even among people in the same family.

There are three types of HAE, known as types I, II, and III. It is estimated that HAE affects 1 in 50,000 people, that type I accounts for about 85 percent of cases, type II accounts for about 15 percent of cases, and type III is very rare. Type III is the most newly described form and was originally thought to occur only in women, but families with affected males have been identified.

HAE is inherited in an autosomal dominant pattern, such that an affected person can inherit the mutation from one affected parent. New mutations in the gene can also occur, and thus HAE can also occur in people with no history of the disorder in their family. It is estimated that 20-25% of cases result from a new spontaneous mutation.

Mutations in the SERPING1 gene cause hereditary angioedema type I and type II. The SERPING1 gene provides instructions for making the C1 inhibitor protein, which is important for controlling inflammation. C1 inhibitor blocks the activity of certain proteins that promote inflammation. Mutations that cause hereditary angioedema type I lead to reduced levels of C1 inhibitor in the blood. In contrast, mutations that cause type II result in the production of a C1 inhibitor that functions abnormally. Without the proper levels of functional C1 inhibitor, excessive amounts of bradykinin are generated. Bradykinin promotes inflammation by increasing the leakage of fluid through the walls of blood vessels into body tissues. Excessive accumulation of fluids in body tissues causes the episodes of swelling seen in individuals with hereditary angioedema type I and type II.

Mutations in the F12 gene are associated with some cases of hereditary angioedema type III, also known as HAE with normal C1 inhibitor. The F12 gene provides instructions for making coagulation FXII. In addition to playing a critical role in blood clotting (coagulation), factor XII is also an important stimulator of inflammation and is involved in the production of bradykinin. Certain mutations in the F12 gene result in the production of factor XII with increased activity. As a result, more bradykinin is generated and blood vessel walls become more leaky, which leads to episodes of swelling. The cause of other cases of hereditary angioedema type III remains unknown. Mutations in one or more as-yet unidentified genes may be responsible for the disorder in these cases.

HAE can present similarly to other forms of angioedema resulting from allergies or other medical conditions, but it differs significantly in cause and treatment. When hereditary angioedema is misdiagnosed as an allergy, it is most commonly treated with antihistamines, steroids, and/or epinephrine, which are typically ineffective in HAE, although epinephrine can be used for life-threatening reactions. Misdiagnoses have also resulted in unnecessary exploratory surgery for patients with abdominal swelling, and in some HAE patients abdominal pain has been incorrectly diagnosed as psychosomatic.

Symptoms of HAE can be assessed, for example, using questionnaires, e.g., questionnaires that are completed by patients, clinicians, or family members. Such questionnaires are known in the art and include, for example, visual analog scales. See, e.g., McMillan, C. V. et al. Patient. 2012; 5(2):113-26.

As used herein, "an effective amount" refers to the amount of each active agent required to confer therapeutic effect on the subject, either alone or in combination with one or more other active agents. In some embodiments, the therapeutic effect is reduced FXIIa activity, reduced amounts of pKal or bradykinin or reduced vasodilation. Antibody inhibitors that specifically bind FXIIa but do not bind FXII may require a lower efficacious dose than antibody inhibitors that also bind FXII. Determination of whether an amount of the antibody achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In one example, dosages for an antibody as described herein may be determined empirically in individuals who have been given one or more administration(s) of the antibody. Individuals are given incremental dosages of the antagonist. To assess efficacy of the antagonist, an indicator of the disease/disorder can be followed.

Generally, for administration of any of the antibodies described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. In some examples, the dosage of the anti-FXII antibody described herein (e.g., DX-4012) can be 10 mg/kg. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an antibody as described herein will depend on the specific antibody, antibodies, and/or non-antibody peptide (or compositions thereof) employed, the type and severity of the disease/disorder, whether the antibody is administered for preventive or therapeutic purposes, previous therapy, the patient's clinical history and response to the antagonist, and the discretion of the attending physician. Typically the clinician will administer an antibody, until a dosage is reached that achieves the desired result. In some embodiments, the desired result is a decrease in thrombosis. Methods of determining whether a dosage resulted in the desired result would be evident to one of skill in the art. Administration of one or more antibodies can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the antibodies described herein are administered to a subject in need of the treatment at an amount sufficient to inhibit the activity of one or both of the target antigen by at least 20% (e.g., 30%, 40%, 50%, 60%, 70%, 80%, 90% or greater) in vivo. In other embodiments, the antibodies are administered in an amount effective in reducing the activity level of a target antigens by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., those encoding the antibodies described herein) are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, i.e., dose, timing and repetition, used in the method described herein will depend on the particular subject and that subject's medical history.

In some embodiments, more than one antibody, or a combination of an antibody and another suitable therapeutic agent, may be administered to a subject in need of the treatment. The antibody can also be used in conjunction with other agents that serve to enhance and/or complement the effectiveness of the agents.

Treatment efficacy for a target disease/disorder can be assessed by methods well-known in the art.

Kits for Use in Alleviating Diseases Associated with Contact System Activation

The present disclosure also provides kits for use in alleviating diseases/disorders associated with contact system activation, such as HAE. Such kits can include one or more containers comprising an anti-FXIIa antibody, e.g., any of those described herein.

In some embodiments, the kit can comprise instructions for use in accordance with any of the methods described herein. The included instructions can comprise a description of administration of the anti-FXIIa antibody to treat, delay the onset, or alleviate a target disease as those described herein. The kit may further comprise a description of selecting an individual suitable for treatment based on identifying whether that individual has the target disease. In still other embodiments, the instructions comprise a description of administering an antibody to an individual at risk of the target disease.

The instructions relating to the use of an anti-FXIIa antibody generally include information as to dosage, dosing schedule, and route of administration for the intended treatment. The containers may be unit doses, bulk packages (e.g., multi-dose packages) or subunit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or disorder associated with the pKal signaling pathway, such as HAE. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-FXIIa antibody as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Generation of Anti-FXIIa Antibodies

A phage display selection using Dyax's FAB310 phagemid library was performed using the biotinylated beta fragment of FXIIa immobilized on streptavidin coated beads. Fab molecules that bound to the immobilized FXIIa were isolated. The selection produced a selective Fab inhibitor that specifically bound to the catalytic domain of FXIIa with a $Ki^{app}$ of 800 pM. The isolated Fab showed no cross-reactivity towards the following proteases tested at a concentration of 1 µM: urokinase plasminogen activator, hepatocyte growth factor activator, activated protein C, cathepsin G, C1s, elastase, factor VIIa, factor Xa, factor XIa, plasmin, thrombin alpha, trypsin, urokinase, plasma kallikrein, hepatocyte growth factor activator, and urokinase-type plasminogen activator.

Figure 2:
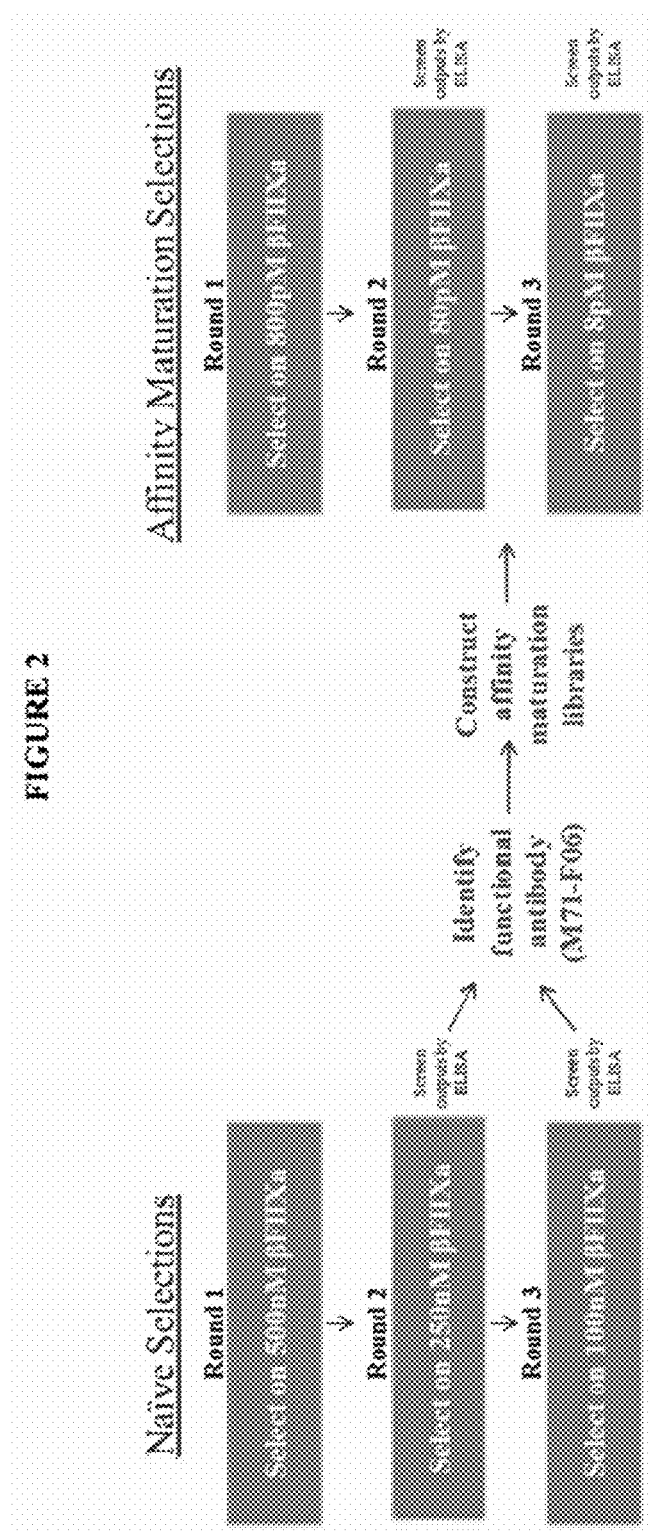
FIG. 2 is a schematic illustration showing the antibody selection strategy.

The isolated Fab, M71-F06, was affinity matured via multiple strategies, including heavy chain CDR1/2 shuffling, light chain shuffling, heavy chain CDR3 wobble, and a combination of heavy chain CDR3 wobble and heavy chain CDR1/2 shuffle. The heavy chain CDR1/2 shuffle library was constructed by removing the CDR1/2 region of M71-F06 and replacing it with the full library diversity to make an affinity maturation library with a diversity of ~$10^8$. The heavy chain CDR3 was varied at each amino acid position from the parental CDR3 sequence of M71-F06 to create a new library, which was also subsequently combined with the HC CDR1/2 shuffle diversity. A second selection was performed using these libraries. As opposed to the selection performed with immobilized FXIIa, as used for the naïve library selection, the affinity maturation libraries were incubated with the biotinylated target in solution at concentrations lower than the parental $Ki^{app}$. The biotinylated FXIIa and any bound Fabs from the libraries were subsequently pulled down on streptavidin coated beads. FIG. 2 presents a schematic of the selection strategy for the identification and generation of anti-FXIIa antibodies.

Figure 4:
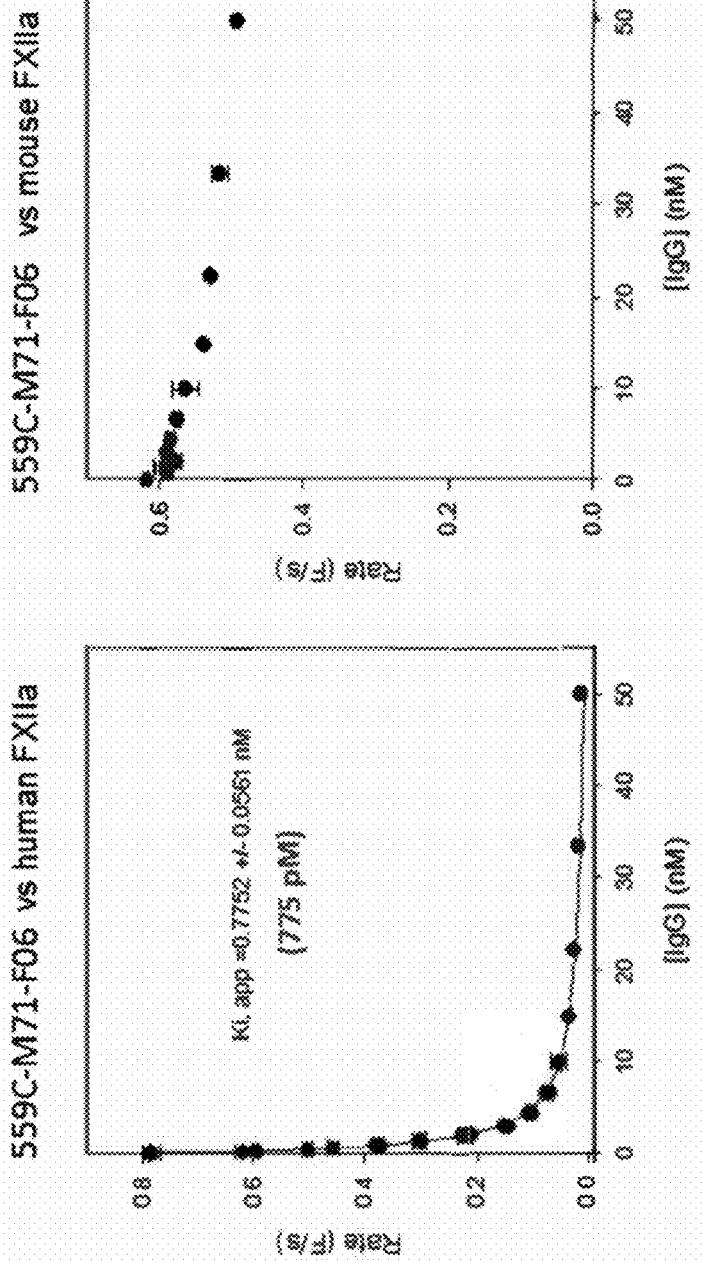
FIG. 4 is a diagram showing the inhibitory activity of parent antibody 559C-M71-F06 (a human IgG1 antibody) against human (left panel) and mouse FXIIa (right panel).
Figure 5:
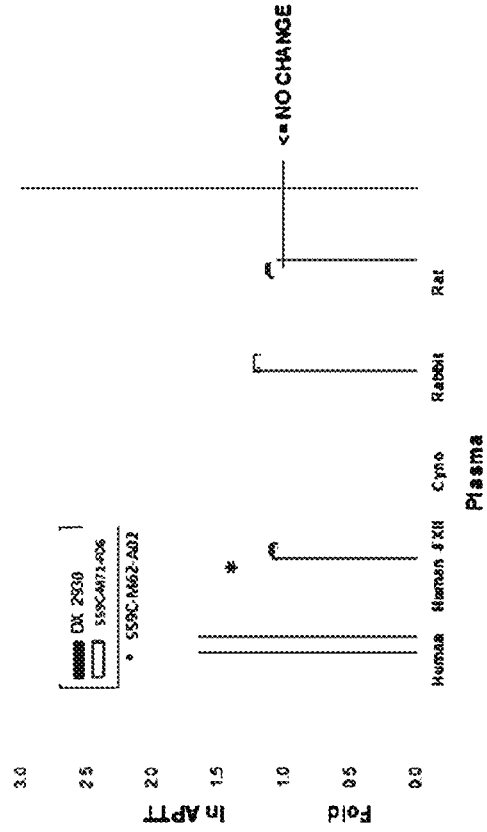
FIG. 5 is a diagram showing species cross-reactivity of M71-F06 as determined by APTT.

The inhibitory activities of clone M71-F06 against human and mouse FXIIa, as determined by the "in vitro" activity assay described in Example 2 below, are shown in FIG. 4. The APTT value of clone M71-F06 (see Example 2 below) as compared to DX-2930 is shown in FIG. 5. Results also indicate that clone M71-F06 has no inhibitory activity against activated protein C, CCC 1s, Cathepsin G, Elastase, Factor VIIa, Factor Xa, Factor XIa, activated plasma kallikrein, plasmin, thrombin alpha, trypsin, urokinase, HGFA, and uPA, indicating that its inhibitory activity is specific to FXIIa.

Any isolated Fabs from the selection were screened by ELISA, resulting in 39 unique isolates. The amino acid sequences of the heavy chain variable regions and light chain variable regions are provided above. These clones are expected to have the same antigen-binding activity and specificity as the parent clone with higher binding affinity.

Example 2: Characterization of Anti-FXIIa Antibodies

Figure 3:
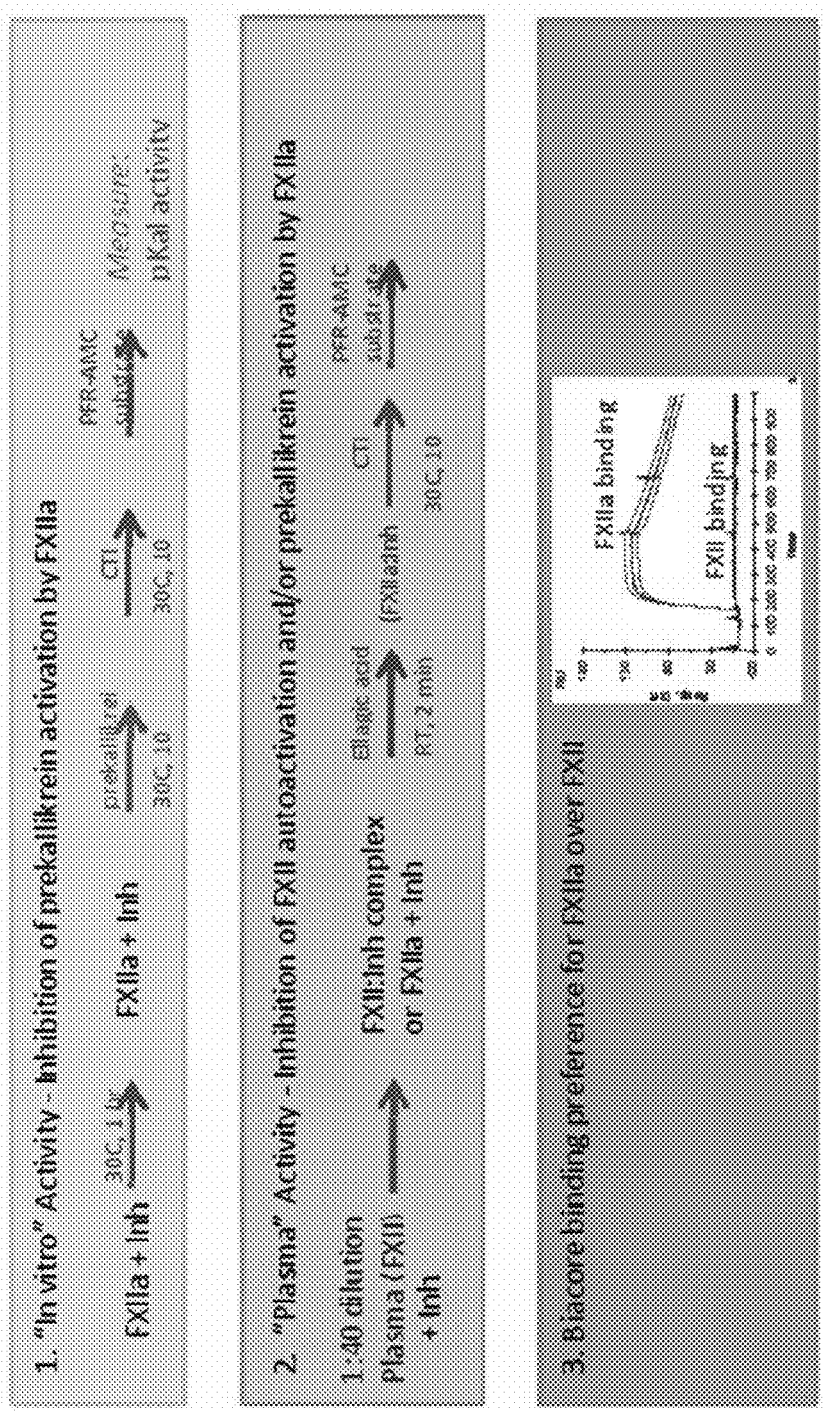
FIG. 3 is a schematic illustration showing the bioassays used for characterizing activity of FXIIa inhibitors, including in vitro activity assay, plasma activity assay, and binding preference assay.

Methods:
Activated Partial Thromboplastin Time (APTT) Assay
Inhibitors (or control dilution buffer=25 mM HEPES, pH 7.5, 125 mM NaCl) were added to neat plasma in a 1:1 mixture, and pre-equilibrated at 37° C. for 5 minutes. 2×50 µl of this mix was dispensed to 2 separate KC4 Delta assay cuvettes (with metal ball). After 60 seconds, 50 µl of aPTT reagent (activator, Pacific Hemostasis APTT-XL) was added to the rotating cuvettes, and 180 seconds after aPTT addition (at t=0 secs), 50 µl of $CaCl_2$ was added. The KC4 Delta instrument recorded the time of coagulation in seconds.
Prothrombin Time (PT) Assay
Inhibitors (or control dilution buffer=25 mM HEPES, pH 7.5, 125 mM NaCl) were added to neat plasma in a 1:1 mixture, and pre-equilibrated at 37° C. for 5 minutes. 2×50 µl of this mix was dispensed to 2 separate KC4 Delta assay cuvettes (with metal ball). After 4 minutes, the PT activator (Pacific Hemostasis Thromboplastin D) was added (at t=0 secs). Coagulation time was automatically recorded by the KC4 Delta instrument.
Purified Component Inhibition Assay
The purified component inhibition assay is depicted in FIG. 3, panel 1. 20 pM FXIIa was incubated with inhibitors at varying concentration for 1 hour at 30° C. in a 96-well microplate. 10 nM Prekallikrein was added for 20 minutes at 30° C., followed by a 5 min incubation with 100 nM corn trypsin inhibitor (CTI). Proteolysis was then assessed over time by addition of 10 uM final fluorogenic peptide substrate (PFR-AMC), with initial rate of substrate proteolysis (y-axis) plotted against inhibitor concentration (x-axis) and the resulting data fit to the modified Morrison equation (Equation 1) for tight binding inhibitors. All reagents were diluted into Assay Buffer=20 mM Tris-HCl pH 7.5, 150 mM NaCl, 1 mM EDTA, 0.1% PEG-8000 and 0.1% Triton X-100.
Plasma Inhibition Assay
The plasma inhibition assay is depicted in FIG. 3, panel 2. Pooled normal human plasma was diluted 1:40 in Assay Buffer (above), and inhibitors were added at varying concentrations in a 96-well microplate at room temperature.

Contact activation was then initiated by the addition of 25% (2.5% final) ellagic acid, the microplate was mixed by gentle shaking, and allowed to proceed for 2 minutes at room temperature, whereby 100 nM of CTI was added. 10 µl of this mixture was then removed to a replicate microplate containing 80 µl of assay buffer at pre-equilibrated at 30 C. This dilution plate was then incubated a further 5 minutes at 30 C, and proteolysis of PFR-AMC assessed as above, but with back-calculated concentrations of inhibitor used in the X-axis for curve-fitting to a standard $IC_{50}$ equation (plasma was diluted 1:400 in final assay read).

One or more of the anti-FXIIa antibodies disclosed herein are also tested in a non-human primate model at two different dosages. The study runs for 30 days after which blood samples are taken to evaluate the pharmacokinetics, effect on APTT, and effect on plasma kallikrein activation via western blot analysis.

Binding Preference Assay

To determine the binding preference of the anti-FXIIa antibodies, each antibody was incubated with the FXII zymogen other related proteases of the contact/coagulation system. The binding affinity was then assessed by surface plasmon resonance (SPR) analysis using a Biacore biosensor. See FIG. 3, panel 3.

Flow Model/Capillary Occlusion Assay

The antibodies are tested in an ex vivo flow model in which human blood supplemented with the antibody is passed at different flow rates through collagen coated capillary tubes. Platelet and fibrin deposition are assessed by fluorescence. Platelet and fibrin deposition is inhibited in this system by antibodies that bind zymogen factor XI or factor XII. In a typical experiment, the antibodies are allowed to bind to their targets before blood flow is initiated.

Mouse Thrombosis Model

The antibodies is tested in a mouse model of ferric chloride-induced carotid artery thrombosis. The model incorporates different $FeCl_3$ concentrations, starting at the lowest concentration that consistently induces thrombus formation in C57Bl/6 mice (3.5%). If the antibody demonstrates an antithrombotic effect at low $FeCl_3$ concentration, progressively higher concentrations are tested until the antithrombotic effect of the antibody is overwhelmed.

Results:

The 39 isolate anti-FXIIa antibodies were tested in various in vitro activity assays to determine the following properties: Ki apparent, $IC_{50}$, binding preference, such as binding to the FXII zymogen, cross-reactivity with other related proteases in the contact/coagulation system, cross-reactivity with closely related sequence homologs, effect on plasma kallikrein (pKal) generation, activity in human plasma, partial thromboplastin time (PT), activated partial thromboplastin time (APTT), and lag time to thrombin generation.

Results of the assays are presented in Table 3. All 39 isolates were found to delay APTT, while having no effect on PT. Each of the 39 affinity matured isolates all demonstrated $Ki^{app}$ increases 10-100 fold over the parental isolate. The antibodies reduced pKal generation as measured by two independent inhibition assays: purified component inhibition assay and plasma inhibition assay.

According to SPR analysis (Biacore), the antibodies did not bind the FXII zymogen, and showed specificity toward the catalytic domain when tested against full length FXIIa. The antibodies also prevented the activation of FXI to FXIa.

TABLE 3

| Isolate | Plasma $Ki^{app}$ (nM) | APTT (fold delay) | $Ki^{app}$ (pM) |
| --- | --- | --- | --- |
| M0191-E09 | 31 | 3.70 | 5 |
| M0183-C03 | 33 | 3.17 | 6 |
| M0184-F12 | 38 | 3.74 | 4 |
| M0183-H08 | 76 | 3.36 | 5 |
| M0182-D04 | 96 | 3.13 | 11 |
| M0192-H11 | 101 | 3.33 | 6 |
| M0292-D07 | 115 | 3.11 | 14 |
| M0183-D08 | 118 | 2.08 | 11 |
| M0192-F07 | 125 | 3.00 | 7 |
| M0192-G03 | 125 | 3.14 | 18 |
| M0310-C06 | 135 | 2.46 | 57 |
| M0192-F01 | 174 | 3.18 | 8 |
| M0191-A03 | 176 | 2.88 | 13 |
| M0192-A01 | 198 | 3.11 | 17 |
| M0191-H10 | 216 | 3.81 | 13 |
| M0177-C12 | 217 | 3.86 | 18 |
| M0184-B04 | 269 | 3.76 | 8 |
| M0308-H03 | 275 | 3.38 | 18 |
| M0192-D02 | 279 | 3.30 | 5 |
| M0310-G07 | 295 | 4.48 | 22 |
| M0192-F06 | 304 | 3.49 | 9 |
| M0310-A04 | 316 | 3.48 | 15 |
| M0310-F02 | 319 | 1.86 | 106 |
| M0310-B09 | 331 | 3.73 | 12 |
| M0310-G06 | 353 | 3.18 | 7 |
| M0182-H01 | 359 | N/A | N/A |
| M0178-A08 | 381 | 3.26 | 7 |
| M0184-D01 | 435 | 3.32 | 4 |
| M0177-A06 | 458 | 4.08 | 17 |
| M0191-E04 | 460 | 3.59 | 7 |
| M0191-H09 | 463 | 3.61 | 16 |
| M0192-H04 | 485 | 3.51 | 9 |
| M0192-A03 | 514 | 3.34 | 13 |
| M0310-G08 | 796 | 2.76 | 24 |
| M0192-G05 | 852 | 3.38 | 15 |
| M0183-B12 | 1004 | 3.06 | 11 |
| M0308-F04 | 1570 | 3.29 | 17 |
| M0182-B04 | N/A | N/A | N/A |
| M0310-F04 | N/A | N/A | N/A |

Figure 21:
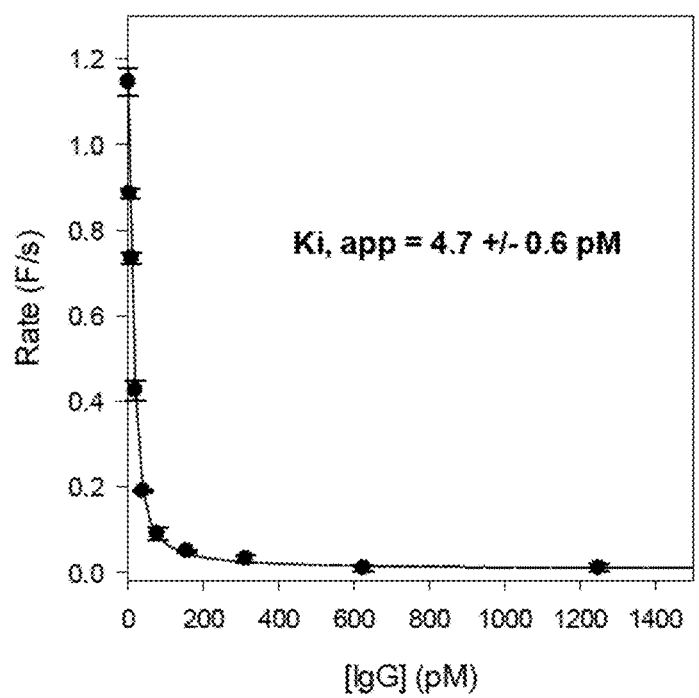
FIG. 21 is a diagram showing the inhibitory activity of the anti-FXIIa antibody M192-H11 against human FXIIa.

The inhibitory activities of clone M0192-H11 against human FXIIa, is shown in FIG. 21, and was found to be approximately 4.7+/−0.6 pM.

Anti-FXIIa antibodies M192-H11 and M192-E09 were also tested in in vivo pharmacokinetic experiments in rats. Groups of rats were injected with 20 mg/kg of either anti-FXIIa antibody M191-E09 or M192-H11. At various days following injection, samples were collected from the rats and assess for concentration of the anti-FXIIa antibody and pharmacokinetic parameters (FIG. 6 and Table 4).

TABLE 4

Pharmacokinetic Characteristics of Antibodies M192-H11 and M191-E09:

| Exemplary Antibody | Cmax (µg/mL) | AUClast (hr*µg/mL) | Cl (ml/hr/kg) | Vss (mL/kg) | $t_{1/2}$ (hr) |
| --- | --- | --- | --- | --- | --- |
| M192-H11 | 360 | 18375 | 0.92 | 242 | 220 |
| M191-E09 | 269 | 7612 | 2.28 | 489 | 218 |

Example 3: Development and Characterization of Anti-FXIIa Antibody 559C-X211-A01

559C-X211-A01 is an affinity matured, partially germlined, version of the previously described parent antibody 559C-M71-F06. The amino acid sequences of the heavy chain variable region and light chain variable region of this antibody are shown below:

559C-X211-A01_HV (CDRs underlined and in boldface)
(SEQ ID NO: 125)
EVQLLESGGGLVQPGGSLRLSCAASGFTFS QYVMH

WVRQAPGKGLEWVS SIWPSGGHTRYADSVKG

RFTISRDNSKNTLYLQMNSLRAEDTAVYYCTR

QRYRGPKYYYYMDV WGKGTTVTVSS

559C-X211-A01_LV (CDRs underlined and in boldface)
(SEQ ID NO: 126)
DIVMTQSPLSLPVTPGEPASISC RSSQSLLHSNGYNYLD

WYLQKPGQSPQLLIY LGSNRAS

GVPDRFSGSGSGTDFTLKISRVEAEDVGVYYC MQALQTPWT

FGQGTKVEIK

559C-X211-A01 was tested in various in vitro activity assays to determine the following properties; $K_i$ apparent, $IC_{50}$, binding to the FXII zymogen, cross-reactivity with other related proteases in the contact/coagulation system, cross-reactivity with closely related sequence homologs, effect on plasma kallikrein (pKal) generation, and activity in human plasma. Partial thromboplastin time (PT), and activated partial thromboplastin time (APTT) in mouse plasma has also been tested in vitro.

Cross-Reactivity Assay

559C-X211-A01 showed no cross-reactivity towards the following proteases tested at 1 µM: urokinase plasminogen activator, human growth factor activator, activated protein C, cathepsin G, C1s, elastase, factor VIIa, factor Xa, factor XIa, plasmin, thrombin alpha, trypsin, urokinase, and plasma kallikrein.

Activated Partial Thromboplastin Time (APTT) and Prothrombin Time Assays

Inhibitors (or control dilution buffer=25 mM HEPES, pH 7.5, 125 mM NaCl) were added to both mouse, and human, neat plasma in a 1:1 mixture, and pre-equilibrated at 37 C for 5 minutes. 2×50 µl of this mix was dispensed to 2 separate KC4 Delta assay cuvettes (with metal ball). After 60 seconds, 50 µl of aPTT reagent (activator, Pacific Hemostasis APTT-XL) was added to the rotating cuvettes, and 180 seconds after this (at t=0 secs) 50 µl of CaCl2 was added. The KC4 Delta instrument recorded the time of coagulation in seconds.

As above, except 4 minutes after the 2×50 µl of inhibitor/plasma mix was dispensed to 2 separate KC4 Delta assay cuvettes, the PT activator (Pacific Hemostasis Thromboplastin D) was added at t=0 secs. Coagulation time was automatically recorded by the KC4 Delta instrument.

Figure 7:
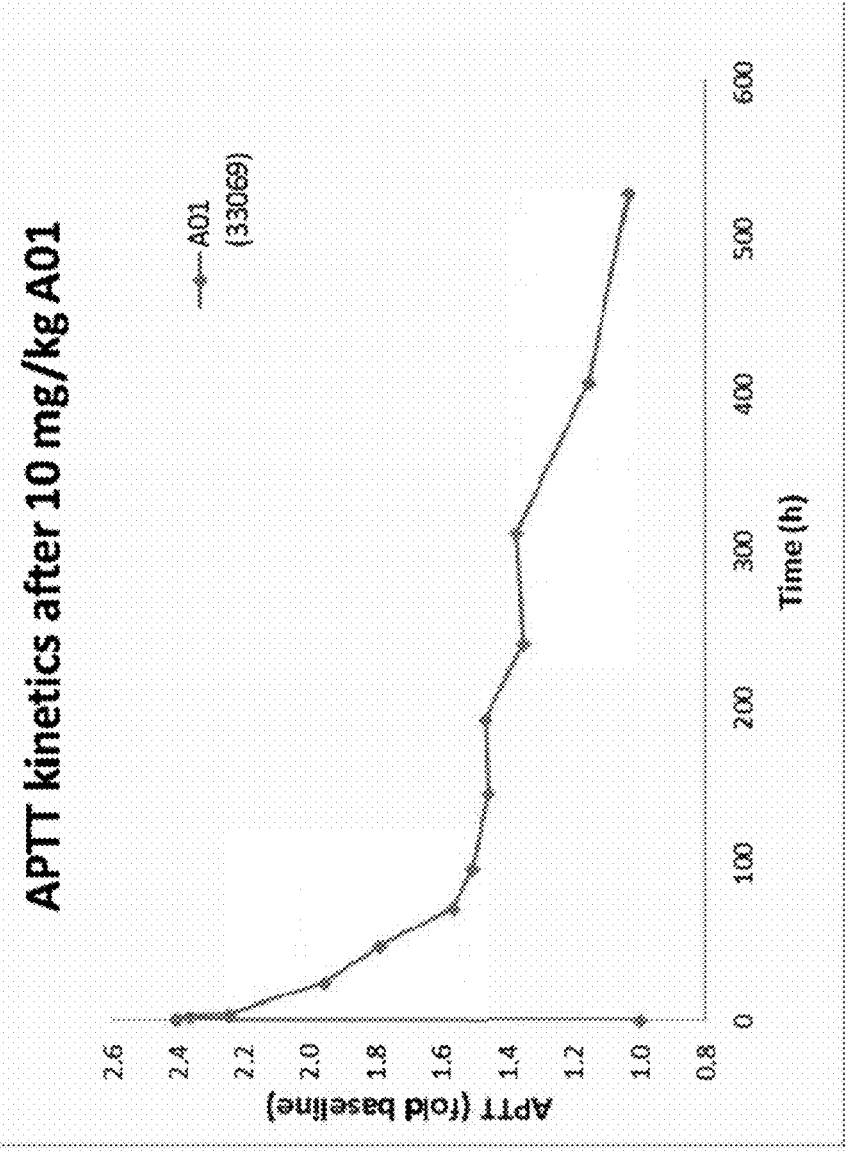
FIG. 7 is a chart showing the time course of APTT and PT increase (sec) in the presence of anti-FXIIa antibody 559C-X211-A01 (A01). A: APTT kinetics after 10 mg/kg A01. B: time course of APTT in the presence of 10 mg/kg A01 over baesline. C: time course of PT (sec) in the presence of 10 mg/kg A01.
Figure 8:
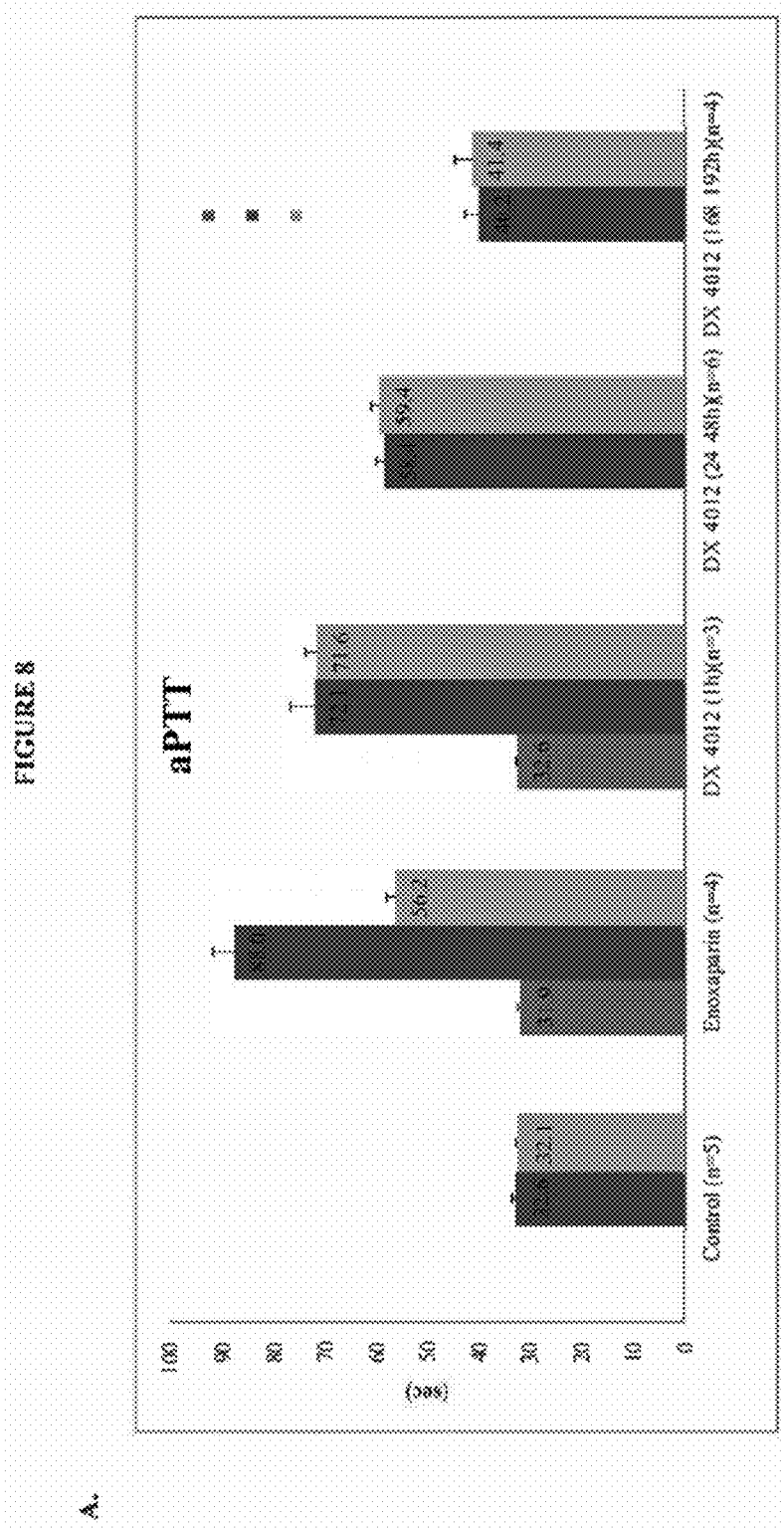
FIG. 8 is a diagram showing APTT activity of antibody DX-4012 at the indicated time points prior to administration of the indicated treatment (Pre Drug, gray bars), 5 minutes prior to initiation of the study (Pre Study, black bars), and 5 minutes prior the end of the study (Post Study, white bars). The values indicate the average APTT +/− standard error in seconds. A: APTT time. B: fold increase in APTT over the baseline value (the average of the pre and post study measurement on the same animal on the control study day(s))
Figure 8:
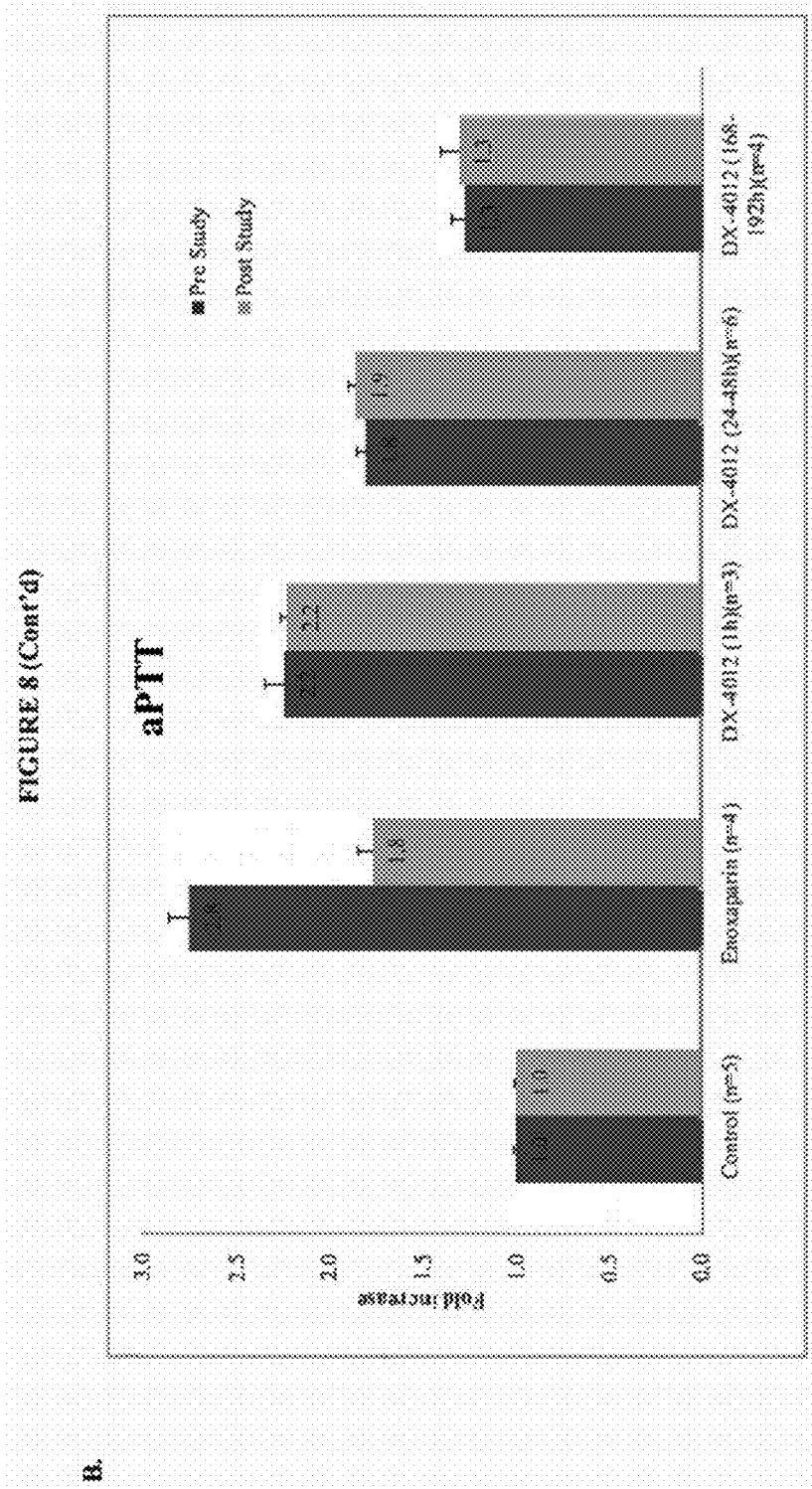
Figure 9:
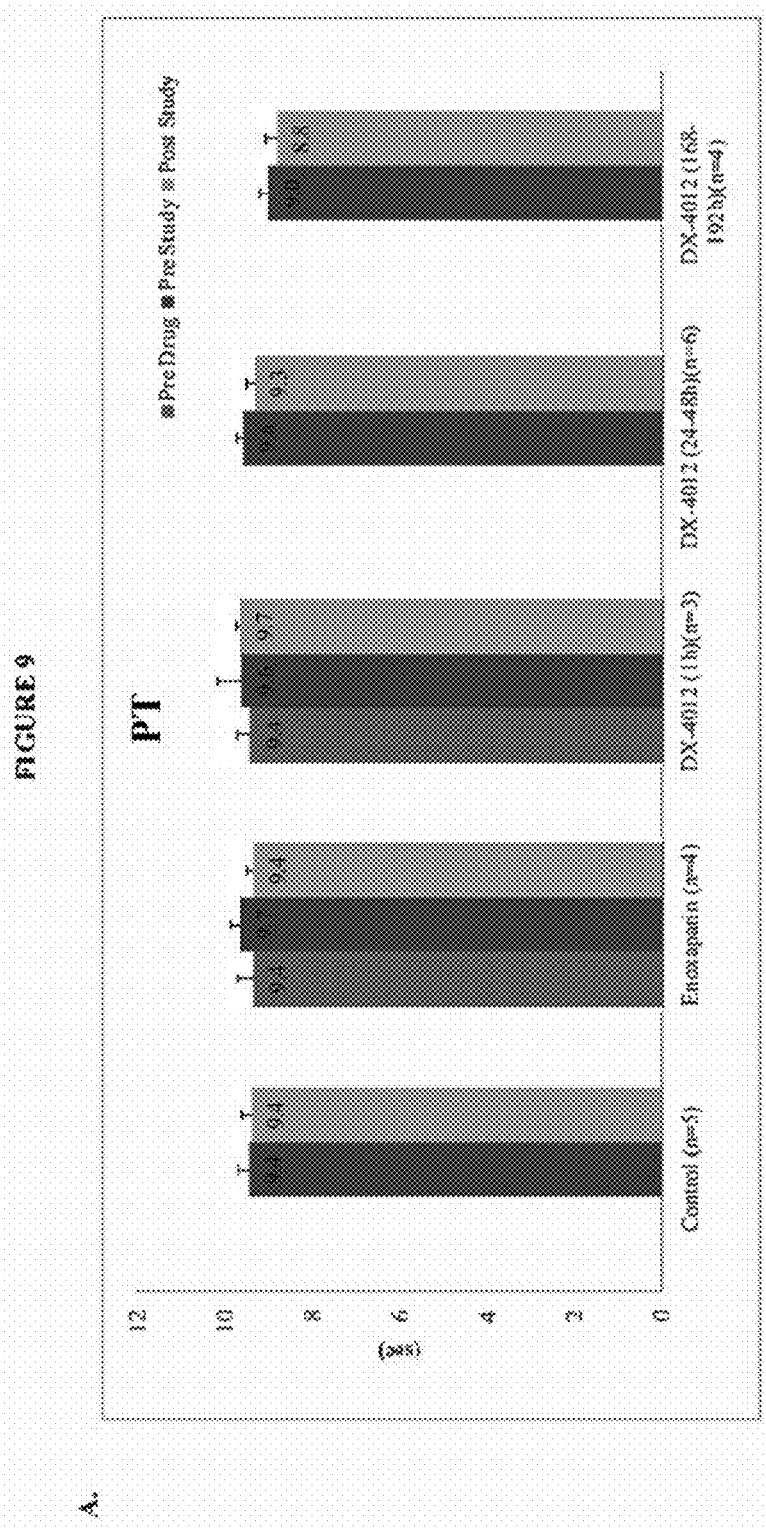
FIG. 9 is a diagram showing PT activity of antibody DX-4012 at the indicated time points prior to administration of the indicated treatment (Pre Drug, gray bars), 5 minutes prior to initiation of the study (Pre Study, black bars), and 5 minutes prior the end of the study (Post Study, white bars). The values indicate the average PT +/− standard error in seconds. A: PT time. B: fold increase in PT over the baseline value (the average of the pre and post study measurement on the same animal on the control study day(s)).
Figure 9:
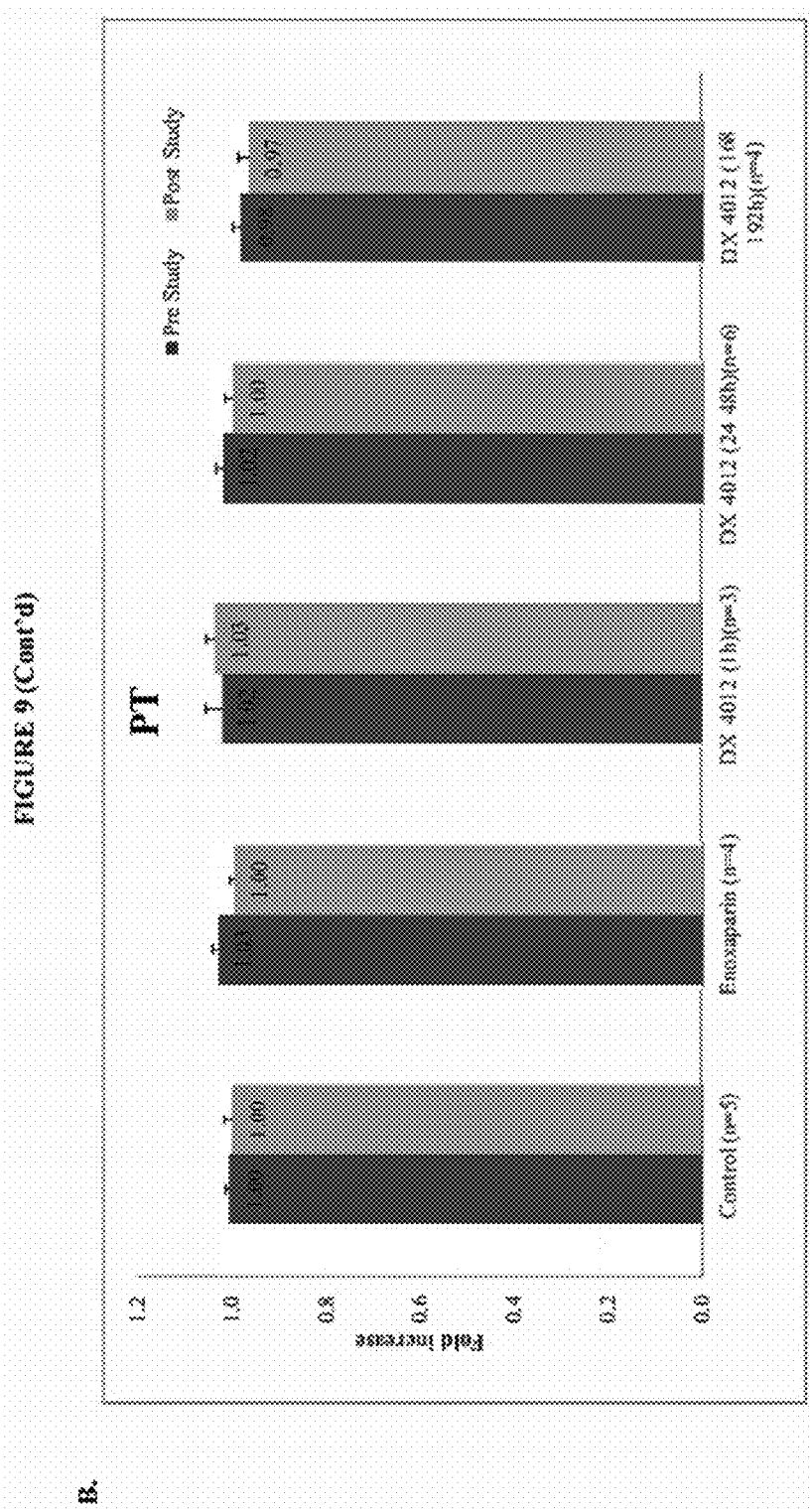

559C-X211-A01 delays APTT in mouse plasma, while having no effect on PT. FIG. 7. This data supports species cross-reactivity with mouse factor XII.

Purified Component Inhibition Assay:

20 pM FXIIa is incubated with inhibitors at varying concentration for 1 hour at 30° C. in a 96-well microplate. 10 nM Prekallikrein is then added for 20 minutes at 30° C., followed by a 5 min incubation with 100 nM corn trypsin inhibitor (CTI). Proteolysis is then assessed over time by addition of 10 uM final fluorogenic peptide substrate (PFR-AMC), with initial rate of substrate proteolysis (y-axis) plotted against inhibitor concentration (x-axis) and the resulting data fit to the modified Morrison equation for tight binding inhibitors. All reagents were diluted into Assay Buffer=20 mM Tris-HCl pH 7.5, 150 mM NaCl, 1 mM EDTA, 0.1% PEG-8000 and 0.1% Triton X-100

Plasma Inhibition Assay:

Pooled normal human plasma is diluted 1:40 in Assay Buffer (above), and inhibitors are added at varying concentration in a 96-well microplate at room temperature. Contact activation is then initiated by the addition of 25% (2.5% final) APTT-XL reagent (dilute ellagic acid; Pacific Haemostasis), the microplate mixed by gentle shaking, and allowed to proceed for 2 minutes at room temperature, whereby 100 nM of CTI is added. 10 ul of this mixture is then removed to a replicate microplate containing 80u1 of assay buffer at pre-equilibrated at 30 C. This dilution plate is then incubated a further 5 minutes at 30 C, and proteolysis of PFR-AMC assessed as above, but with back-calculated concentrations of inhibitor used in the X-axis for curve-fitting to a standard IC50 equation and/or modified Morrison equation (plasma is diluted 1:400 in final assay read).

The activities of 559C-X211-A01 observed in the above-noted assays are summarized in Table 5 below:

TABLE 5

| | Activities of 559C-X211-A01 | | | |
|---|---|---|---|---|
| Isolate | Plasma IC50 (nM) | APTT (fold delay) using 1 uM X211-A01 in human plasma | APTT (fold delay) using 1 uM X211-A01 in mouse plasma | $K_i^{app}$ (pM) |
| 559C-X211-A01 | 289 | 3.4 | 2.8 | 5 |

According to SPR analysis, this antibody binds to FXIIa and does not bind the FXII zymogen. Enzyme inhibition experiments with FXIIa-beta show specific targeting to the catalytic domain.

559C-X211-A01 is expected to reduce fibrin generation and deposition, to prolong the time it takes for blood to occlude a collagen-coated capillary tube in a flow model/capillary occlusion assay, and/or to reduce platelet aggregation and the incidence of arterial inclusion. 559C-211-A01 is expected to reduce the incidence of thrombus formation in both a mouse model of thrombosis and a non-human primate model of thrombosis.

Example 4: In Vivo Thrombosis Studies Using DX-4012

Pharmacokinetic Studies

The anticoagulant effect of a single dose of DX-4012 was assessed in healthy baboons as a pharmacodynamic marker of the presence of the antibody in the circulation. The animals were mildly sedated, and blood was drawn from the antecubital vein for baseline coagulation values. The antibody was then administered, at a saturating dose. A single dose of the antibody was delivered intravenously, and blood samples were drawn at various time points as long as anticoagulation can be verified in the APTT assay relative to baseline. Plasma samples were also frozen for additional testing.

Following completion of the pharmacokinetic studies and determination of the effective half-life of the antibody in baboons, pharmacodynamic thrombosis and hemostasis studies were pursued.

Pharmacodynamic and Thrombosis Studies

Acute thrombosis and hemostasis experiments were performed before and during anticoagulation to determine the efficacy and safety of the antibody at a single saturating dose compared to a positive and negative control. The thrombosis experiments were performed in trained baboons by deploying a vascular graft segment into a chronic exteriorized femoral AV shunt. Each day of the study, 1 mL of citrated blood was taken from the loop of the shunt at various time points for serial bleeding time, volume measurements, and anticoagulation assays. Sample times include pre drug (on the day the animal received enoxaparin or DX-4012 prior to administration of enoxaparin or DX-4012), pre study (5 minutes prior to the start of the study), and post study (5 minutes prior to the end of the study, when the shunt loop was removed). Prior to the thrombosis and hemostasis experiments, the baboons received $^{111}$In-radiolabeled autologous platelets and $^{125}$I-radiolabeled fibrinogen. The antithrombotic activity of DX-4012 was compared to that of enoxaparin (low molecular weight heparin).

After baseline blood samples were drawn, the thrombosis experiments were initiated. The chronic AV shunt was temporally (60 min) extended using silicon tubing, and a short collagen ePTFE graft segment or tissue factor-coated ePTFE vascular graft segment (20 mm) was deployed within the external AV loop (FIG. 10). A thrombus formed in the graft (head thrombus) and extended on the distal side (thrombus tail). Accumulation of radiolabeled platelets in the graft was monitored in real time using gamma camera imaging for 60 minutes and calculated as the number of platelets residing in the graft at 5 minute intervals. After 60 min of graft perfusion, the graft was removed, the shunt reconnected, and the amount of deposited fibrin in the graft by 60 min (end-point) was determined after decay of $^{111}$In (30+ days–approximately 10 half-lives later). Fibrin and platelet numbers represent the size of the thrombus.

Results

APTT and PT assays were performed as described in Examples 2 and 3. APTT was measured using citrated plasma, SynthA Sil® (Instrumentation Laboratories) reagent, and a KC-4 coagulometer. PT was measured using citrated plasma, Dade® Innovin® reagent (Siemens), and a KC-4 coagulometer. Both APTT and PT were measured immediately following blood draw and centrifugation of the blood sample to generate platelet-poor plasma. At 1 hour post administration of DX-4012, the measured fold change in APTT was 2.2 fold (>2.2 fold expected). At 24-48 hrs, the measured fold change in APTT was 1.8 fold (1.8-2.0 fold expected); and at 1 week, the measured fold change in APTT was 1.3 fold (1.3-1.5 fold expected). There were no observed changes to PT.

Collagen Graft

For the thrombosis studies, the animals received 10 mg/kg of antibody DX-4012, and the studies were performed at 1 hr, 24 hr, 48 hr, 168 hr, and 192 hrs following antibody administration. For analysis, data from the 24 and 48 hr time points were grouped together, and data from the 168 and 192 hr time points were grouped together. Control animals formed a collagen-initiated baseline thrombus head as expected. The thrombus head was significantly reduced in animals that received enoxaparin. At time points up to 48 hrs post antibody administration, the thrombus head size was reduced relative to the control animals and was comparable to that of animals that received enoxaparin. At one week following antibody administration (168-192 hrs), the thrombus head size was comparable to that of control animals (FIG. 11A). At time points up to 48 hrs post antibody administration, the thrombus tail was nearly abolished and comparable to that of animals that received enoxaparin. At one week following antibody administration (168-192 hrs), the thrombus tail remained reduced, but to a lesser extent than post-enoxaparin treatment (FIG. 11B).

Figure 14:
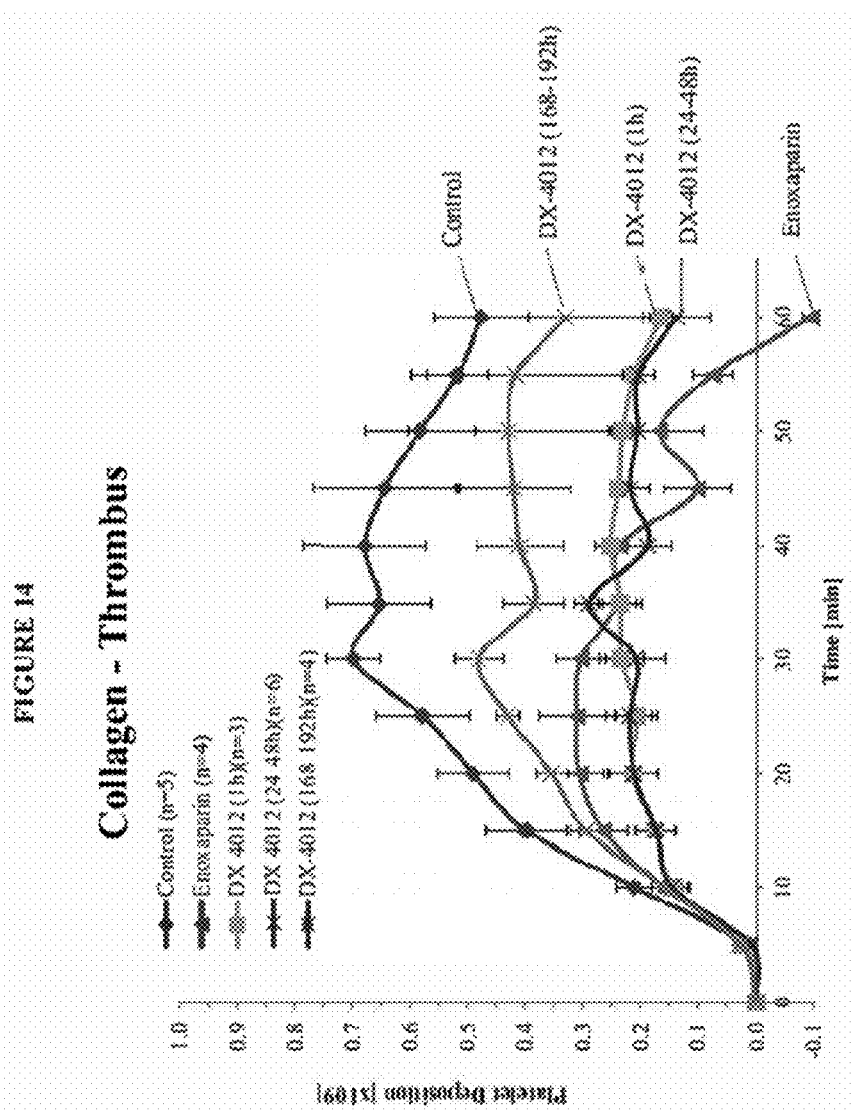
FIG. 14 is a chart showing the thrombus growth rate on a collagen-coated graft measured as platelet deposition per 5 minute interval.

In another experiment, at time points up to 48 hrs post antibody administration, the thrombus head size was reduced relative to the control animals and was comparable to that of animals that received enoxaparin. At one week following antibody administration (168-192 hrs), the thrombus head size was still reduced but to a lesser extent than post-enoxaparin treatment (FIG. 12). FIG. 13 presents thrombus formation (total thrombus), indicating that thrombus formation was comparable at 1 hr, 24 hr and 48 hrs post antibody administration. The thrombus growth rate (platelet deposition at 5 minute intervals) is shown in FIG. 14. Control thrombi had increasing growth rate in the first 30 minutes before reaching a plateau. The growth rate after enoxaparin treatment reached a lower plateau at 20 minutes, began to decline after 40 minutes, and lysed at 60 minutes (negative growth rate). Within the first 48 hrs after DX-4012 administration, the growth rate plateaued at 15-20 minutes and had a reduced rate of growth. One week after antibody administration, thrombi were between the early time points (1 hr and 24-48 hrs) and the control.

Overall, administration of 10 mg/kg DX-4012 reduced the size of the thrombus formed by collagen initiation, the effects of which were seen on both the thrombus head size and the thrombus tail. The reduction in thrombus size was observed up to 48 hrs post antibody administration and was comparable to enoxaparin treatment (1 mg/kg). After one week, the head thrombus returned to baseline in animals that received the antibody, but thrombus tail size remained reduced.

Tissue Factor Graft

Figure 15:
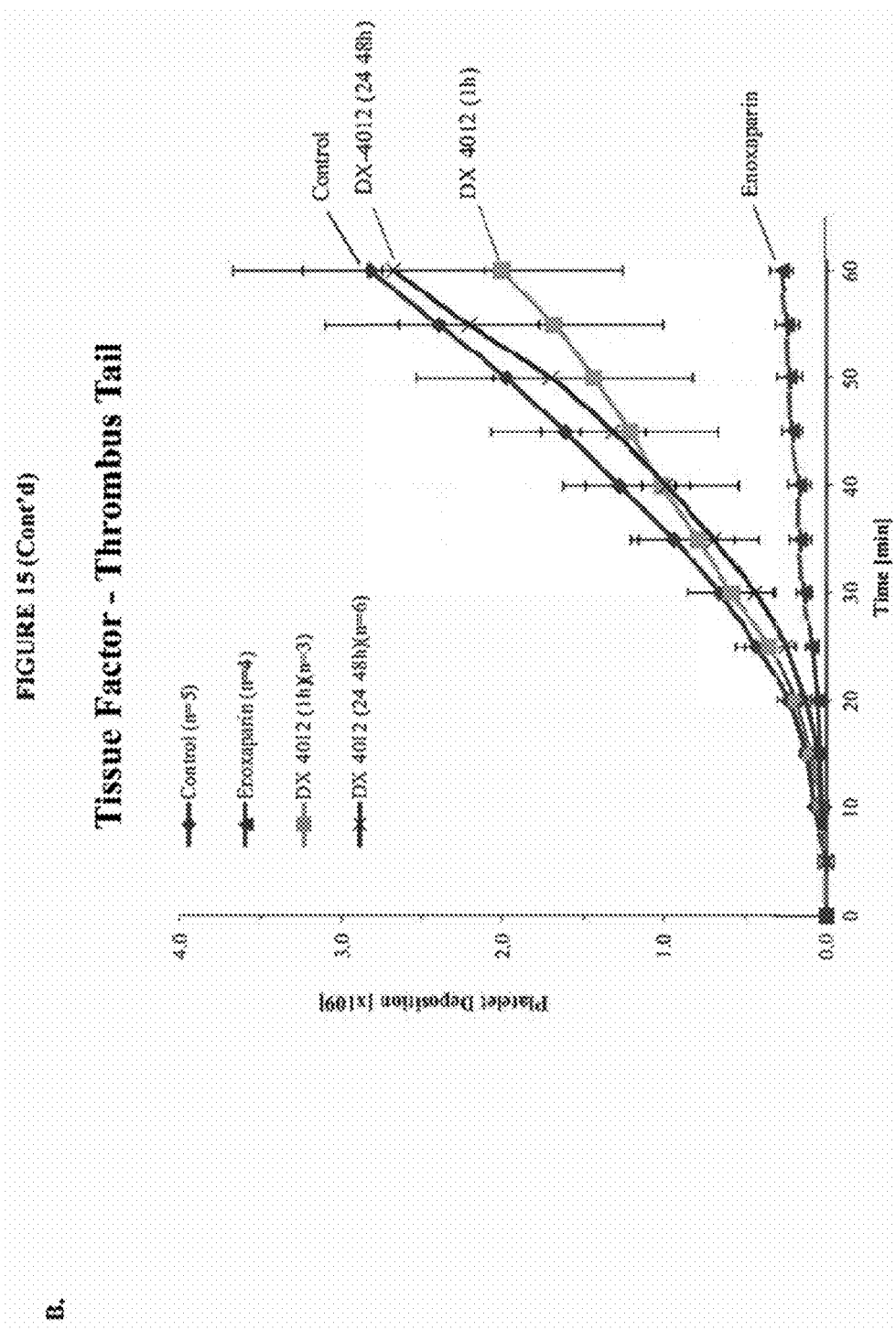
FIG. 15 is a chart showing the time course of platelet deposition on a tissue factor-coated graft. A: Thrombus head. B: Thrombus tail.

In general, thrombi sizes tend to vary more in tissue factor-coated shunts compared to collagen-coated shunts. Wide variation was observed in the described experiments (7.4, 14.0 and 2.3 billion platelets). Control animals formed a tissue factor-initiated baseline thrombus head as expected. The thrombus head was significantly reduced in animals that received enoxaparin. At time points up to 48 hrs post antibody administration, the thrombus head size was comparable to that of the control animals (FIG. 15A). At one week following antibody administration (168-192 hrs), the thrombus head size varied greatly. Enoxaparin treatment nearly abolished tissue factor-initiated thrombus tail formation. There was no significant thrombus tail reduction in animals that received antibody treatment, though the data suggested that there was a slight trend toward a smaller thrombus tail (FIG. 15B).

Figure 16:
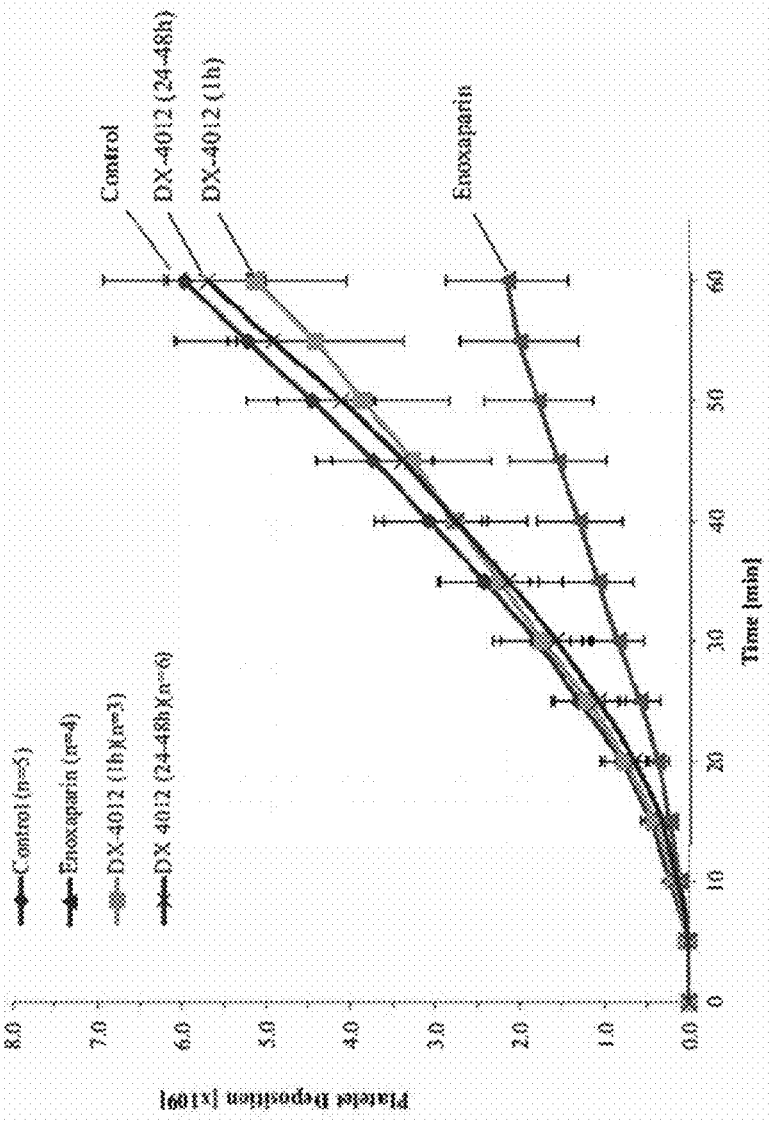
FIG. 16 is a chart showing the time course of platelet deposition on a tissue factor-coated graft.
Figure 17:
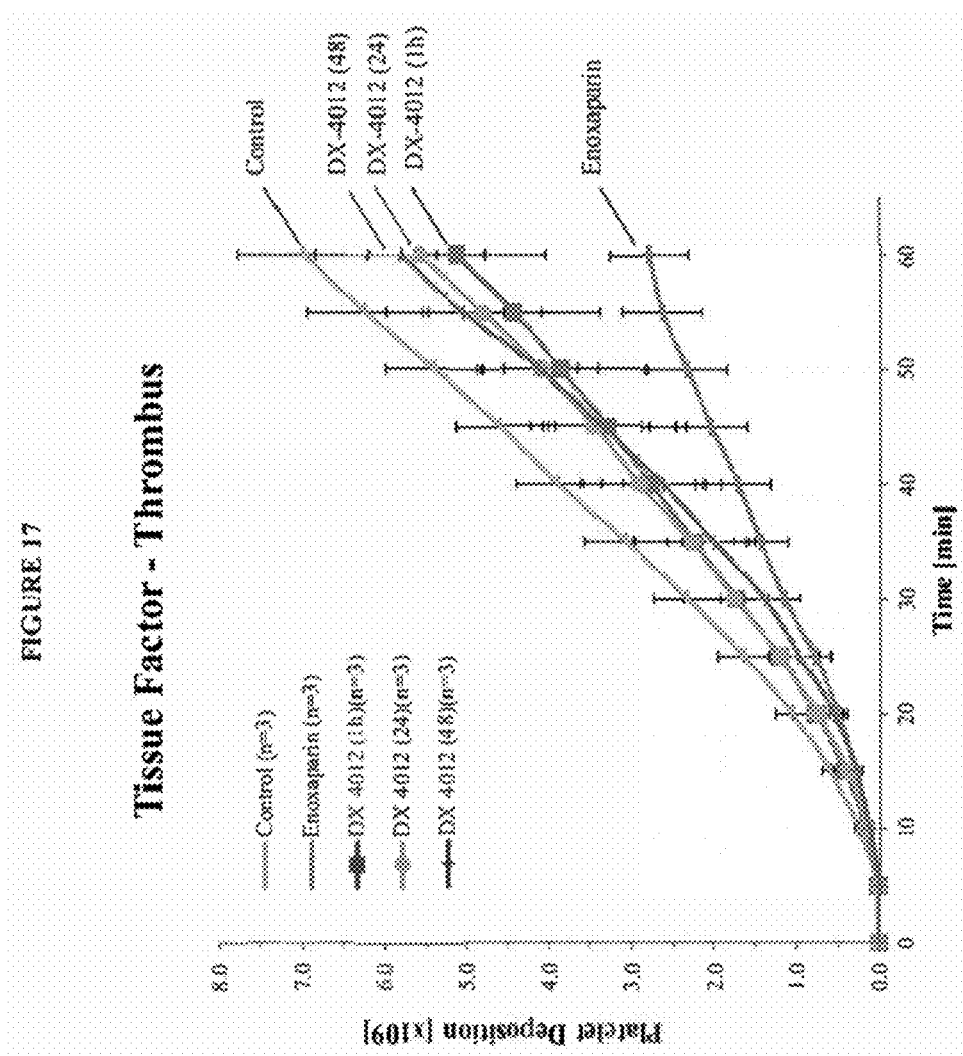
FIG. 17 is a chart showing the time course of platelet deposition on a tissue factor-coated graft.
Figure 18:
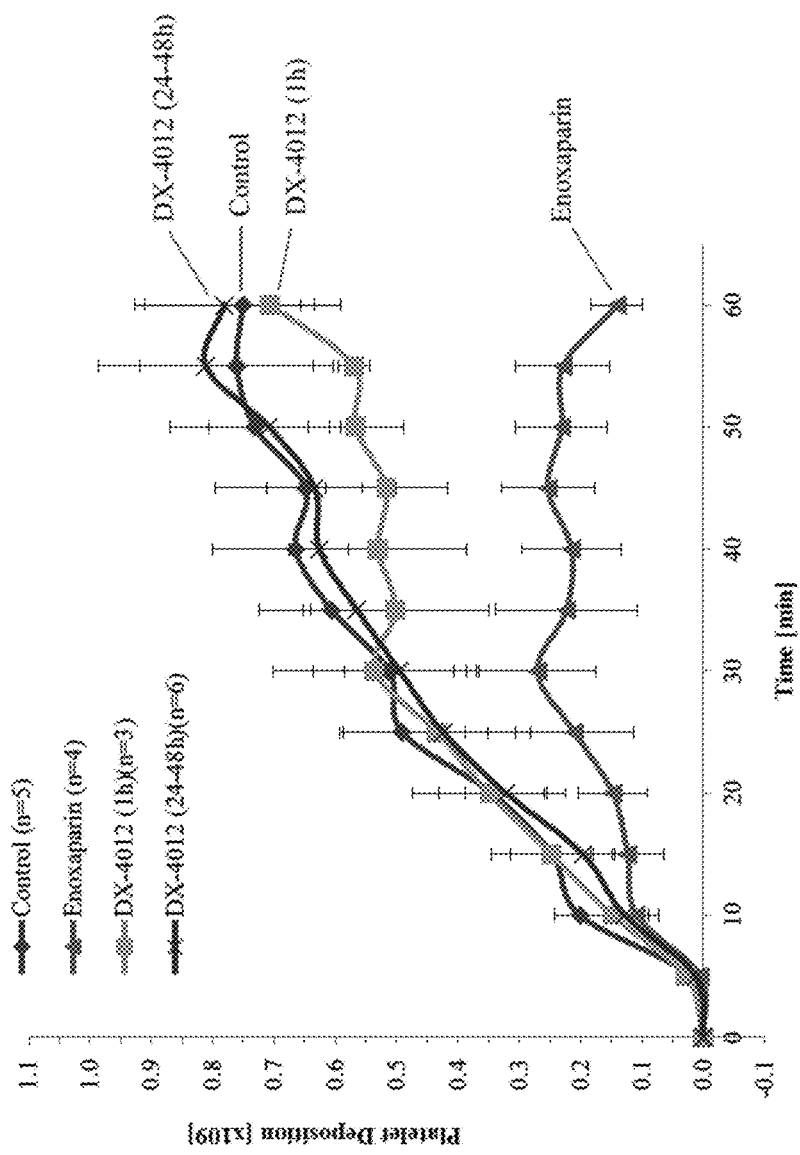
FIG. 18 is a chart showing the thrombus growth rate on a tissue factor-coated graft measured as platelet deposition per 5 minute interval.

In another experiment, enoxaparin treatment resulted in a reduction in the thrombus size by >50%, largely due to nearly abolishing the thrombus tail. There was no significant thrombus tail reduction in animals that received antibody treatment, though the data suggested that there was a slight trend toward a smaller thrombus tail (FIG. 16). FIG. 17 presents thrombus formation (total thrombus). Performing RM ANOVA analysis of the data indicated there was a reduction in the total thrombus size at 1 hr following antibody treatment as compared to the control. The thrombus growth rate (platelet deposition at 5 minute intervals) is shown in FIG. 18. Control thrombi had increasing growth rate in the first 30 minutes before reaching a plateau. The growth rate after enoxaparin treatment reached a plateau at 20 minutes, began to decline after 40 minutes, and lysed at 60 minutes (negative growth rate). Within the first 48 hrs after DX-4012 administration, the thrombus growth rate was similar to the observed rate in the control animal (FIG. 18).

Overall, administration of 10 mg/kg DX-4012 had no effect on the thrombus head size and little effect on the thrombus tail size in tissue factor-initiated thrombus formation.

Terminal Fibrin Content and Platelet Deposition

At the end of the experiment, the shunts were flushed with saline and images were captured to assess the final platelet count. The loop was also preserved for fibrin content analysis of the thrombus head and tail.

Figure 19:
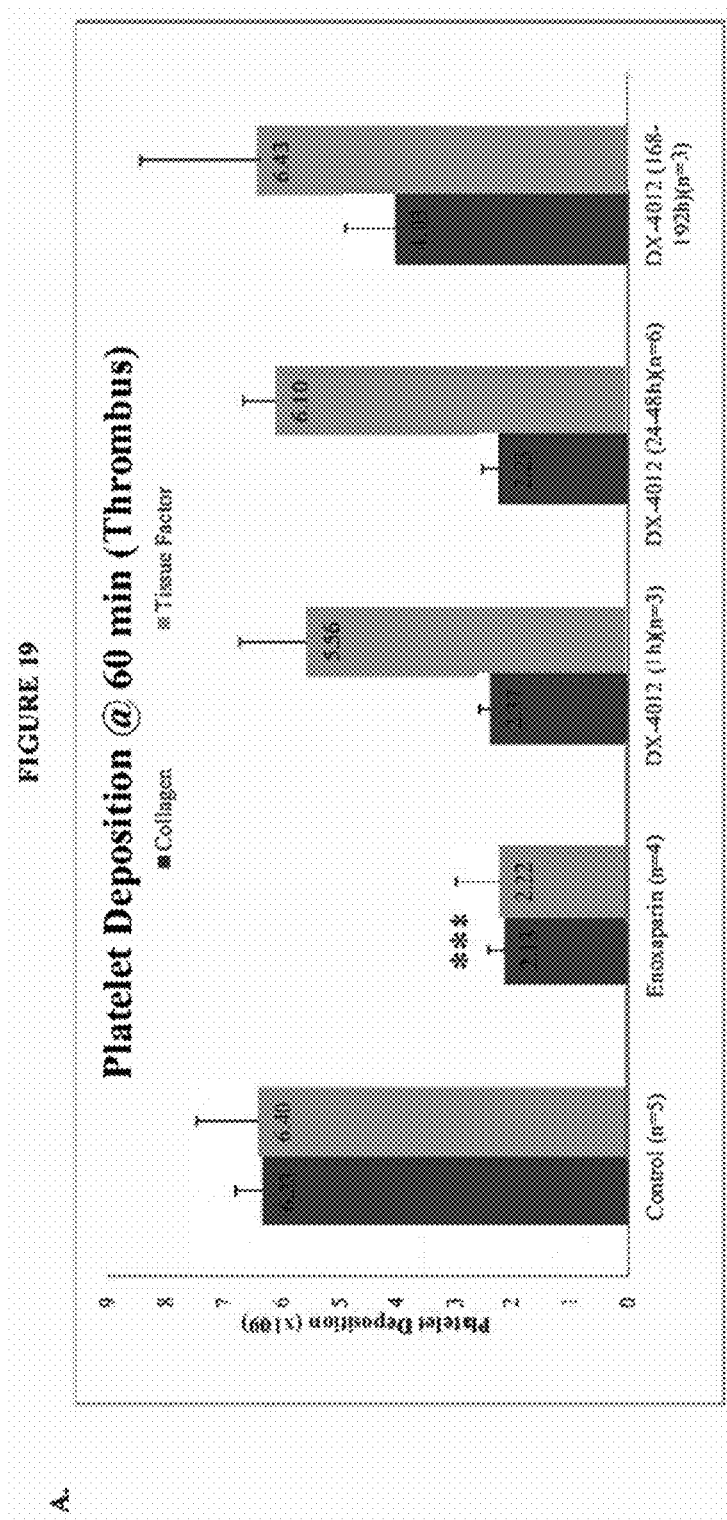
FIG. 19 is a diagram showing terminal fibrin content and platelet deposition in the whole thrombus (head and tail) in collagen-coated grafts (gray bars) and tissue factor-coated grafts (white bars). A: Platelet deposition. B: Fibrin content.
Figure 19:
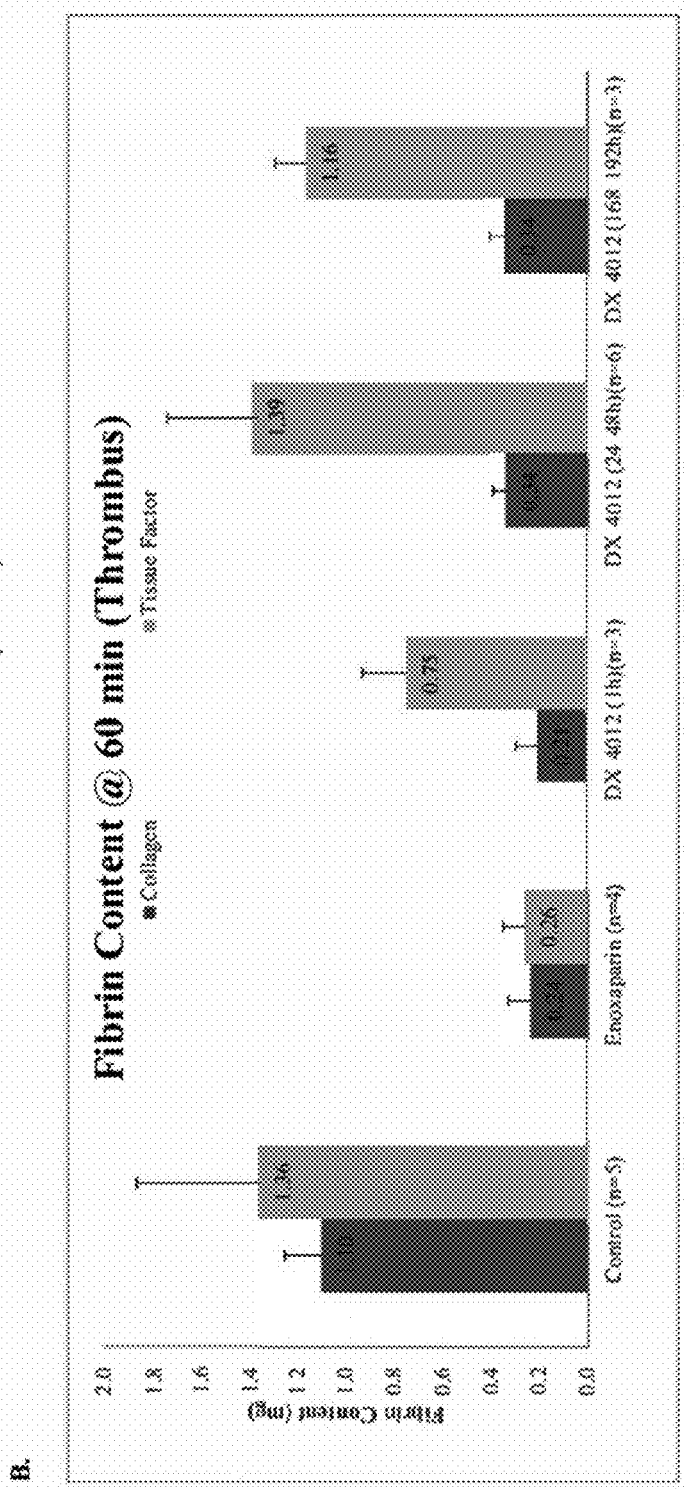

Terminal thrombus size was reduced in animals that received enoxaparin. Thrombus size was also significantly reduced, as measured by both platelet deposition and fibrin content, in collagen-coated shunts in the animals that received DX-4012, but was not reduced in tissue factor-coated shunts (FIGS. 19A and 19B).

Hemostasis Studies

Hemostasis was measured using the FDA-approved Surgicutt™ bleeding time device and protocol. Blood volume was also measured. One bleeding time and bleeding volume measurement was performed per study day. As shown in FIGS. 22A and 22B, DX-4012 was effective in reducing the bleeding time and bleeding volume as compared with Enoxaparin.

Example 5: Identification of Critical Residues in the Catalytic Domain of FXIIa Based on the Crystal Structure of DX-4012-FXIIa Complex A recombinant Fab fragment of DX-4012 was prepared via routine recombinant technology in *E. coli* and purified. The FXIIa was produced and purified via routine methods.

Figure 20:
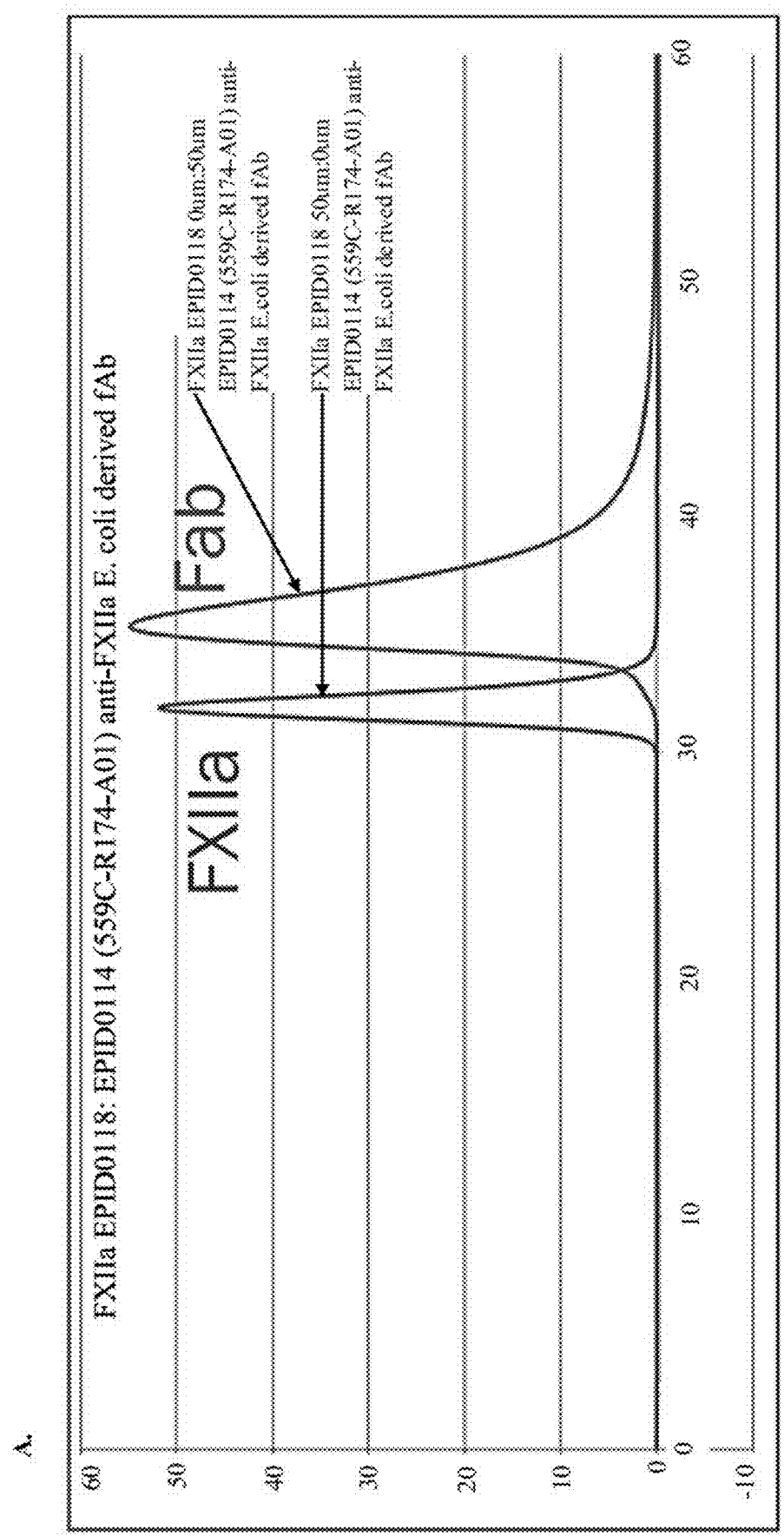
FIG. 20 is a chart showing the complex formation of the Fab fragment of DX-4012 and FXIIa by SEC analysis. A: FXIIa and Fab. B: FXIIa, Fab, and FXIIa-Fab complex of 50 µM FXIIa and 30 µM Fab. C: FXIIa, Fab, and FXIIa-Fab complex of 50 µM FXIIa and 40 µM Fab. D: FXIIa, Fab, and FXIIa-Fab complex of 50 µM FXIIa and 50 µM Fab. E: FXIIa, Fab, and FXIIa-Fab complex of 50 µM FXIIa and 60 µM Fab.
Figure 20:
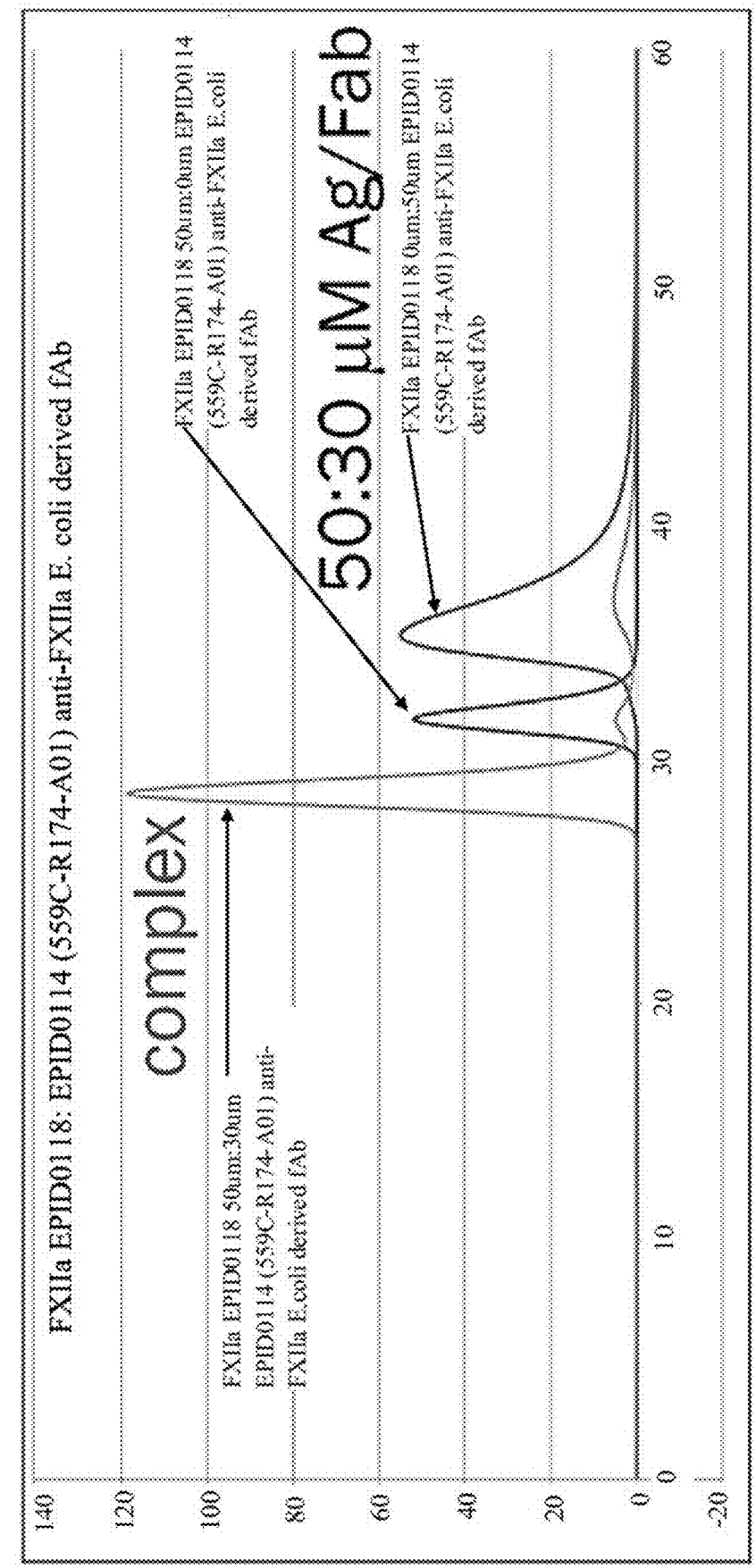
Figure 20:
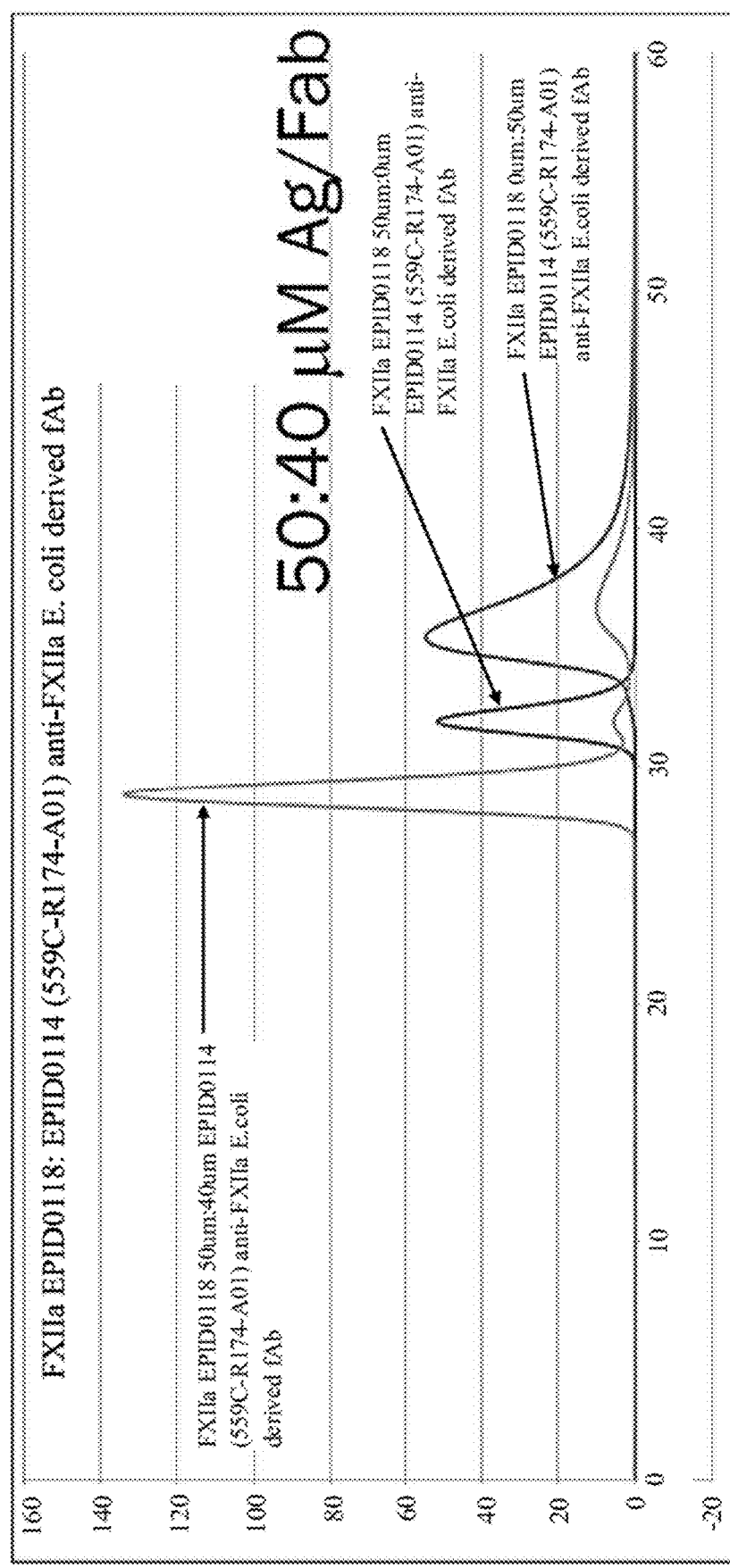
Figure 20:
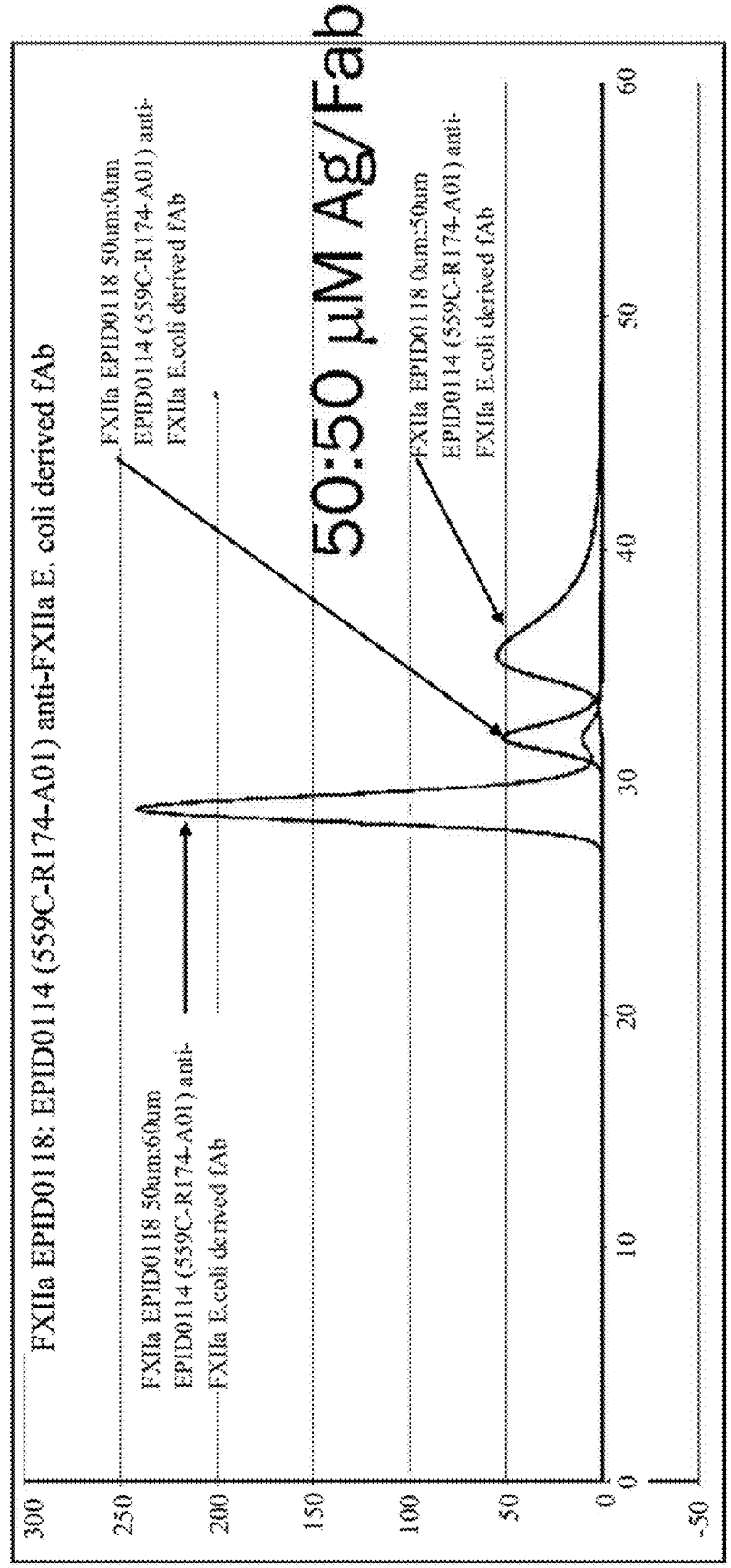
Figure 20:
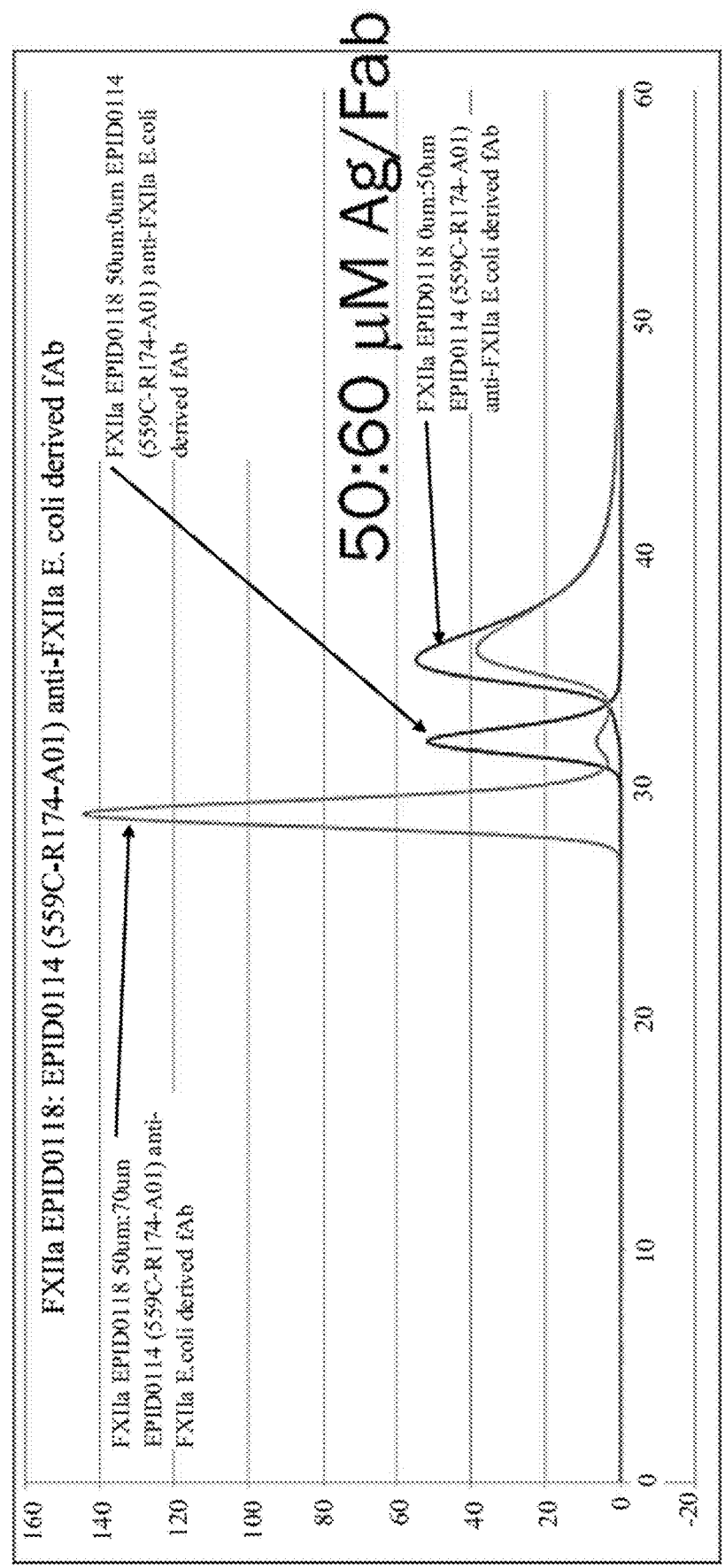

The DX-4012 Fab fragment and the FXIIa were mixed at various concentrations under suitable conditions allowing of Fab-FXIIa complexes. The complexes were purified using SEC and visualized in the traces shown in FIG. 20.

The Fab-FXIIa complex was kept under various conditions allowing for crystallization. Diffraction analysis was performed on the crystallized complex. The crystal structures (2.6 Å and 2.25 Å) were determined based on the diffraction statistics.

According to the crystal structures, residues in the C chain of FXIIa that are involved in the interaction with the Fab fragment of DX-4012 were identified: L390, Y391, W392, G393, H394, 5395, F396, C397, H412, C413, L414, Q415, D416, R432, N433, V456, Y458, H507, F509, E510, G511, A512, E513, Y515, D557, A558, C559, Q560, G561, D562, S563, I584, S585, W586, G587, S588, G589, C590, G591, D592, G597.

In addition, residues in the Fab of DX-4012 that interact with FXIIa were also identified based on the crystal structure, including T28, S30, Q31, W52, P53, S54, G55, G56, H57, R59, N74, R100, Y101, R102, G103, P104, K105, Y106, Y107, and Y108 in the heavy chain variable region, and H31, N33, Y35, Y54, L55, N58, and T99 in the light chain variable region.

These results indicate that the heavy chain of DX-4012 is the main region that interacts with FXIIa and a couple of residues in the LC CDR1 were found to contribute to the interaction.

The crystal structures also revealed that residue R102 of the anti-FXIIa Fab fragment binds the S1 pocket of FXIIa and interacts with residue D557 via water-mediated interactions. This positions the backbone of residues Fab residues R102-G103-P104 near the catalytic triad of FXIIa but in a catalytically incompetent orientation. P104 may contribute to holding this orientation rigidly, thereby inhibiting the activity of FXIIa.

Complexes of other anti-FXIIa antibodies and Fab fragments thereof with FXIIa are also formed and co-purified in order to determine additional crystal structures.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or"

should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A monoclonal antibody that binds to Factor XIIa (FXIIa) wherein the antibody comprises a heavy chain comprising a heavy chain variable region that comprises a heavy chain complementarity determining region 1 (HC CDR1), a heavy chain complementarity determining region 2 (HC CDR2), and a heavy chain complementarity determining region 3 (HC CDR3), and a light chain comprising a light chain variable region that comprises a light chain CDR1 (LC CDR1), a light chain CDR2 (LC CDR2), and a light chain CDR3 (LC CDR3), wherein:

(i) the HC CDR1 comprises QYVMH (SEQ ID NO: 58), the HC CDR2 comprises SIWPSGGHTRYADSVKG (SEQ ID NO: 75), and the HC CDR3 comprises QRYRGPKYYYYMDV (SEQ ID NO: 111);

(ii) the HC CDR1 comprises WYSMH (SEQ ID NO: 41), the HC CDR2 comprises VIYPSGGKTRYADSVKG (SEQ ID NO: 74), and the HC CDR3 comprises QRYRGPKYYYYMDV (SEQ ID NO: 111);

(iii) the HC CDR1 comprises QYVMH (SEQ ID NO: 42), the HC CDR2 comprises SIWPSGGHTRYADSVKG (SEQ ID NO: 75), and the HC CDR3 comprises QRYRGPKYYYYMDV (SEQ ID NO: 111);

(iv) the HC CDR1 comprises WYVMH (SEQ ID NO: 43), the HC CDR2 comprises GIWPSGGRTKYADSVKG (SEQ ID NO: 76), and the HC CDR3 comprises QRYRGPKYYYYMDV (SEQ ID NO: 111);

(v) the HC CDR1 comprises NYVMH (SEQ ID NO: 44), the HC CDR2 comprises SIWPSGGKTKYADSVKG (SEQ ID NO: 77), and the HC CDR3 comprises QRYRGPKYYYYMDA (SEQ ID NO: 112);

(vi) the HC CDR1 comprises MYTMN (SEQ ID NO: 45), the HC CDR2 comprises RIYPSGGKTLYADSVKG (SEQ ID NO: 78), and the HC CDR3 comprises QRYRGPKYYYYMDV (SEQ ID NO: 111);

(vii) the HC CDR1 comprises QYVMS (SEQ ID NO: 46), the HC CDR2 comprises RIYPSGGVTKYADSVKG (SEQ ID NO: 79), and the HC CDR3 comprises QRYRGPKYYYYMDV (SEQ ID NO: 111);

(viii) the HC CDR1 comprises WYNMH (SEQ ID NO: 47), the HC CDR2 comprises YISPSGGKTKYTDSVKG (SEQ ID NO: 80), and the HC CDR3 comprises QRYRGPKYYYYMDV (SEQ ID NO: 111);

(ix) the HC CDR1 comprises RYIMH (SEQ ID NO: 48), the HC CDR2 comprises SIYPSGGVTKYADSVKG (SEQ ID NO: 81), and the HC CDR3 comprises QRYRGPKYYYYMDV (SEQ ID NO: 111);

(x) the HC CDR1 comprises RYIMG (SEQ ID NO: 49), the HC CDR2 comprises SIYPSGGVTRYADSVKG (SEQ ID NO: 82), and the HC CDR3 comprises QRYRGPKYYYYMDV (SEQ ID NO: 111);

(xi) the HC CDR1 comprises QYNMV (SEQ ID NO: 50), the HC CDR2 comprises RIWPSGGKTTYADSVKG (SEQ ID NO: 83), and the HC CDR3 comprises QRYRGPKYYYYMDV (SEQ ID NO: 111);

(xii) the HC CDR1 comprises RYVMV (SEQ ID NO: 51), the HC CDR2 comprises RIYPSGGMTQYADSVKG (SEQ ID NO: 84), and the HC CDR3 comprises QRYRGPKYYYYMDV (SEQ ID NO: 111);

(xiii) the HC CDR1 comprises WYNMA (SEQ ID NO: 52), the HC CDR2 comprises RIYPSGGMTQYADSVKG (SEQ ID NO: 84), and the HC CDR3 comprises QRYRGPKYYYYMDV (SEQ ID NO: 111);

(xiv) the HC CDR1 comprises QYIMH (SEQ ID NO: 53), the HC CDR2 comprises SIYPSGGNTKYADSVKG (SEQ ID NO: 85), and the HC CDR3 comprises QRYRGPKYYYYMDV (SEQ ID NO: 111);

(xv) the HC CDR1 comprises HYVMH (SEQ ID NO: 54), the HC CDR2 comprises SIYPSGGLTKYADSVKG (SEQ ID NO: 86), and the HC CDR3 comprises QRYRGPKYYYYMDV (SEQ ID NO: 111);

(xvi) the HC CDR1 comprises WYTMH (SEQ ID NO: 55), the HC CDR2 comprises SIYPSGGFTRYADSVKG (SEQ ID NO: 87), and the HC CDR3 comprises QRYRGPKYYYYMDV (SEQ ID NO: 111);

(xvii) the HC CDR1 comprises FYHMH (SEQ ID NO: 56), the HC CDR2 comprises RIVPSGGMTRYADSVKG (SEQ ID NO: 88), and the HC CDR3 comprises QRYRGPKYYYYMDV (SEQ ID NO: 111);

(xviii) the HC CDR1 comprises FYSMH (SEQ ID NO: 57), the HC CDR2 comprises RIYPSGGVTKYADSVKG (SEQ ID NO: 89), and the HC CDR3 comprises QRYRGPKYYYYMDV (SEQ ID NO: 111);

(xix) the HC CDR1 comprises QYVMH (SEQ ID NO: 58), the HC CDR2 comprises SIWPSGGKTTYADSVKG (SEQ ID NO: 90), and the HC CDR3 comprises QRYRGPKYYYYMDV (SEQ ID NO: 111);

(xx) the HC CDR1 comprises QYVMH (SEQ ID NO: 58), the HC CDR2 comprises SIWPSGGFTKYADSVKG (SEQ ID NO: 91), and the HC CDR3 comprises QRYRGPKYYYYMDV (SEQ ID NO: 111);

(xxi) the HC CDR1 comprises FYNMH (SEQ ID NO: 59), the HC CDR2 comprises SIYPSGGVTRYADSVKG (SEQ ID NO: 92), and the HC CDR3 comprises QRYRGPKYYYYMDV (SEQ ID NO: 111);

(xxii) the HC CDR1 comprises WYVMH (SEQ ID NO: 43), the HC CDR2 comprises SIYPSGGKTSYADSVKG (SEQ ID NO: 93), and the HC CDR3 comprises QRYRGPKYYYYMDV (SEQ ID NO: 111);

(xxiii) the HC CDR1 comprises PYIMH (SEQ ID NO: 60), the HC CDR2 comprises VIYPSGSKTNYADSVKG (SEQ ID NO: 94), and the HC CDR3 comprises QRYRGPKYYYYMDV (SEQ ID NO: 111);

(xxiv) the HC CDR1 comprises RYTMR (SEQ ID NO: 61), the HC CDR2 comprises SIWPSGGMTRYADSVKG (SEQ ID NO: 95), and the HC CDR3 comprises QRYRGPKYYYYMDV (SEQ ID NO: 111);

(xxv) the HC CDR1 comprises QYVMH (SEQ ID NO: 58), the HC CDR2 comprises SIYPSGGLTRYADSVKG (SEQ ID NO: 96), and the HC CDR3 comprises QRYRGPKYYYYMDV (SEQ ID NO: 111);

(xxvi) the HC CDR1 comprises WYIMG (SEQ ID NO: 62), the HC CDR2 comprises YIYPSGGNTRYADSVKG (SEQ ID NO: 97), and the HC CDR3 comprises QRYRGPKYYYYMDV (SEQ ID NO: 111);

(xxvii) the HC CDR1 comprises RYVMH (SEQ ID NO: 63), the HC CDR2 comprises SIWPSGGMTKYADSVKG (SEQ ID NO: 98), and the HC CDR3 comprises QRYRGPKYYYYMDV (SEQ ID NO: 111);

(xxviii) the HC CDR1 comprises FYIMG (SEQ ID NO: 64), the HC CDR2 comprises RIYPSGGATQYADSVKG (SEQ ID NO: 99), and the HC CDR3 comprises QRYRGPKYYYYMDV (SEQ ID NO: 111);

(xxix) the HC CDR1 comprises FYVMG (SEQ ID NO: 65), the HC CDR2 comprises RIYPSGGLTQYADSVKG (SEQ ID NO: 100), and the HC CDR3 comprises QRYRGPKYYYYMDV (SEQ ID NO: 111);

(xxx) the HC CDR1 comprises FYSMH (SEQ ID NO: 66), the HC CDR2 comprises RIYPSGGITSYADSVKG (SEQ ID NO: 101), and the HC CDR3 comprises QRYRGPKYYYYMDV (SEQ ID NO: 111);

(xxxi) the HC CDR1 comprises MYIMH (SEQ ID NO: 67), the HC CDR2 comprises SIYPSGGMTKYADSVKG (SEQ ID NO: 102), and the HC CDR3 comprises QRYRGPKYYYYMDV (SEQ ID NO: 111);

(xxxii) the HC CDR1 comprises MYVMH (SEQ ID NO: 68), the HC CDR2 comprises SIYPSGGLTKYADSVKG (SEQ ID NO: 103), and the HC CDR3 comprises QRYRGPKYYYYMDV (SEQ ID NO: 111);

(xxxiii) the HC CDR1 comprises QYVMH (SEQ ID NO: 58), the HC CDR2 comprises RIYPSGGLTNYADSVKG (SEQ ID NO: 104), and the HC CDR3 comprises QRYRGPKYYYYMDV (SEQ ID NO: 111);

(xxxiv) the HC CDR1 comprises WYVMQ (SEQ ID NO: 69), the HC CDR2 comprises SIYPSGGMTRYADSVKG (SEQ ID NO: 102), and the HC CDR3 comprises QRYRGPKYYYYMDV (SEQ ID NO: 111);

(xxxv) the HC CDR1 comprises WYIMG (SEQ ID NO: 62), the HC CDR2 comprises RIYPSGGSTHYADSVKG (SEQ ID NO: 105), and the HC CDR3 comprises QRYRGPRYYYYIDA (SEQ ID NO: 113);

(xxxvi) the HC CDR1 comprises QYTMV (SEQ ID NO: 70), the HC CDR2 comprises RIYPSGGVTQYADSVKG (SEQ ID NO: 106), and the HC CDR3 comprises QRYRGPKYYYYMDV (SEQ ID NO: 111);

(xxxvii) the HC CDR1 comprises WYVMY (SEQ ID NO: 71), the HC CDR2 comprises RIYPSGGITHYADSVKG (SEQ ID NO: 107), and the HC CDR3 comprises QRYRGPKYYYYMDV (SEQ ID NO: 111);

(xxxviii) the HC CDR1 comprises FYVML (SEQ ID NO: 72), the HC CDR2 comprises SIWPSGGVTKYADSVKG (SEQ ID NO: 108), and the HC CDR3 comprises QRYRGPKYYYYMDV (SEQ ID NO: 111);

(xxxix) the HC CDR1 comprises WYVMQ (SEQ ID NO: 69), the HC CDR2 comprises YIYPSGGHTKYADSVKG (SEQ ID NO: 109), and the HC CDR3 comprises QRYRGPKYYYYMDV (SEQ ID NO: 111);

(xxxx) the HC CDR1 comprises RYSMN (SEQ ID NO: 73), the HC CDR2 comprises GIYPSGGKTKYADSVKG (SEQ ID NO: 110), and the HC CDR3 comprises QRYRGPKYYYYMDV (SEQ ID NO: 111); and the LC CDR1 comprises RSSQSLLHSNGYNYLD (SEQ ID NO: 114), the LC CDR2 comprises LGSNRAS (SEQ ID NO: 115), and the LC CDR3 comprises MQALQTPWT (SEQ ID NO: 116).

2. The antibody of claim 1, wherein the antibody is a full length antibody or an antigen-binding fragment thereof.

3. The antibody of claim 2, wherein the antibody is a Fab.

4. The antibody of claim 1, wherein the antibody is a human antibody or a humanized antibody.

5. The antibody of claim 1, wherein the heavy chain further comprises a heavy chain constant region.

6. The antibody of claim 5, wherein the heavy chain constant region comprises one or more mutations that enhance half-life of the antibody as compared to the wild-type counterpart.

7. The antibody of claim 6, wherein the one or more mutations are at one or more positions corresponding to position 145, 147, and/or 149 of SEQ ID NO:119.

8. The antibody of claim 7, wherein the one or more mutations are one or more amino acid substitutions of M145Y, S147T, and/or T149E.

9. The antibody of claim 6, wherein the heavy chain constant region comprises the amino acid sequence of SEQ ID NO: 120.

10. The antibody of claim 1, wherein:

(i) the heavy chain variable region comprises the amino acid sequence EVQLLESGGGLVQPGGSLRLSCAASGFTFSQYVMHWVRQAPGKGLEWVSSIWPSGGHT RYADSVKGRFTISRDNSKNTLYLQMNSLRAEDTAVYYCTRQRYRGPKYYYYMDVWG KGTTVTVSS (SEQ ID NO: 125);

(ii) the heavy chain variable region comprises the amino acid sequence EVQLLESGGGLVQPGGSLRLSCAASGFTFSWYSMHWVRQAPGKGLEWVSVIYPSGGKT RYADSVKGRFTISRDNSKNTLYLQMNSLRAEDTAVYYCTRQRYRGPKYYYYMDVWG KGTTVTVSS (SEQ ID NO: 1);

(iii) the heavy chain variable region comprises the amino acid sequence EVQLLESGGGLVQPGGSLRLSCAASGFTFSQYVMHWVRQAPGKGLEWVSSIWPSGGHT RYADSVKGRFTISRDNSKNTLYLQMNSLRAEDTAVYYCTRQRYRGPKYYYYMDVWG KGTTVTVSS (SEQ ID NO: 2);

(iv) the heavy chain variable region comprises the amino acid sequence EVQLLESGGGLVQPGGSLRLS-CAASGFTFSWYVMHWVRQAPGK-GLEWVSGIWPSGGR TKYADSVKGRFTIS-RDNSKNTLYLQMNSLRAEDTAVYYCTRQRYR-GPKYYYYMDVWG KGTTVTVSS (SEQ ID NO: 3);

(v) the heavy chain variable region comprises the amino acid sequence EVQLLESGGGLVQPGGSLRLS-CAASGFTFSNYVMHWVRQAPGK-GLEWVSSIWPSGGKT KYADSVKGRFTIS-RDNSKNTLYLQMNSLRAEDTAVYYCTRQRYR-GPKYYYYMDAWG QGTTVTVSS (SEQ ID NO: 4);

(vi) the heavy chain variable region comprises the amino acid sequence EVQLLESGGGLVQPGGSLRLS-CAASGFTFSMYTMNWVRQAPGK-GLEWVSRIYPSGGKT LYADSVKGRFTIS-RDNSKNTLYLQMNSLRAEDTAVYYCTRQRY-RGPKYYYYMDVWGK GTTVTVSS (SEQ ID NO: 5);

(vii) the heavy chain variable region comprises the amino acid sequence EVQLLESGGGLVQPGGSLRLS-CAASGFTFSQYVMSWVRQAPGK-GLEWVSRIYPSGGVT KYADSVKGRFTIS-RDNSKNTLYLQMNSLRAEDTAVYYCTRQRYR-GPKYYYYMDVWG KGTTVTVSS (SEQ ID NO: 6);

(viii) the heavy chain variable region comprises the amino acid sequence EVQLLESGGGLVQPGGSLRLS-CAASGFTFSWYNMHWVRQAPGKGLEWVSY-ISPSGGKT KYTDSVKGRFTISRDNSKNT-LYLQMNSLRAEDTAVYYCTRQRYRGPKYYYY-MDVWGK GTTVTVSS (SEQ ID NO: 7);

(ix) the heavy chain variable region comprises the amino acid sequence EVQLLESGGGLVQPGGSLRLS-CAASGFTFSRYIMHWVRQAPGK-GLEWVSSIYPSGGVTK YADSVKGRFTIS-RDNSKNTLYLQMNSLRAEDTAVYYCTRQRYR-GPKYYYYMDVWGK GTTVTVSS (SEQ ID NO: 8);

(x) the heavy chain variable region comprises the amino acid sequence EVQLLESGGGLVQPGGSLRLS-CAASGFTFSRYIMGWVRQAPGK-GLEWVSSIYPSGGVTR YADSVKGRFTIS-RDNSKNTLYLQMNSLRAEDTAVYYCTRQRYR-GPKYYYYMDVWGK GTTVTVSS (SEQ ID NO: 9);

(xi) the heavy chain variable region comprises the amino acid sequence EVQLLESGGGLVQPGGSLRLS-CAASGFTFSQYNMVWVRQAPGK-GLEWVSRIWPSGGKT TYADSVKGRFTIS-RDNSKNTLYLQMNSLRAEDTAVYYCTRQRYR-GPKYYYYMDVWGK GTTVTVSS (SEQ ID NO: 10);

(xii) the heavy chain variable region comprises the amino acid sequence EVQLLESGGGLVQPGGSLRLS-CAASGFTFSRYVMVWVRQAPGK-GLEWVSRIYPSGGMT QYADSVKGRFTIS-RDNSKNTLYLQMNSLRAEDTAVYYCTRQRYR-GPKYYYYMDVWG KGTTVTVSS (SEQ ID NO: 11);

(xiii) the heavy chain variable region comprises the amino acid sequence EVQLLESGGGLVQPGGSLRLS-CAASGFTFSWYNMAWVRQAPGK-GLEWVSRIYPSGGM TQYADSVKGRFTIS-RDNSKNTLYLQMNSLRAEDTAVYYCTRQRYR-GPKYYYYMDVWG KGTTVTVSS (SEQ ID NO: 12);

(xiv) the heavy chain variable region comprises the amino acid sequence EVQLLESGGGLVQPGGSLRLS-CAASGFTFSQYIMHWVRQAPGK-GLEWVSSIYPSGGNTK YADSVKGRFTIS-RDNSKNTLYLQMNSLRAEDTAVYYCTRQRYR-GPKYYYYMDVWGK GTTVTVSS (SEQ ID NO: 13);

(xv) the heavy chain variable region comprises the amino acid sequence EVQLLESGGGLVQPGGSLRLS-CAASGFTFSHYVMHWVRQAPGK-GLEWVSSIYPSGGLT KYADSVKGRFTIS-RDNSKNTLYLQMNSLRAEDTAVYYCTRQRYR-GPKYYYYMDVWG KGTTVTVSS (SEQ ID NO: 14);

(xvi) the heavy chain variable region comprises the amino acid sequence EVQLLESGGGLVQPGGSLRLS-CAASGFTFSWYTMHWVRQAPGK-GLEWVSSIYPSGGFT RYADSVKGRFTIS-RDNSKNTLYLQMNSLRAEDTAVYYCTRQRYR-GPKYYYYMDVWG KGTTVTVSS (SEQ ID NO: 15);

(xvii) the heavy chain variable region comprises the amino acid sequence EVQLLESGG-GLVQPGGSLRLS-CAASGFTFSFYHMHWVRQAPGK-GLEWVSRIVPSGGMT RYADSVKGRFTISRDNSKNTLYLQMNSLRAED-TAVYYCTRQRYRGPKYYYYMDVWG KGTTVTVSS (SEQ ID NO: 16);

(xviii) the heavy chain variable region comprises the amino acid sequence EVQLLESGG-GLVQPGGSLRLS-CAASGFTFSFYSMHWVRQAPGK-GLEWVSRIYPSGGVT KYADSVKGRFTISRDNSKNTLYLQMNSLRAED-TAVYYCTRQRYRGPKYYYYMDVWG KGTTVTVSS (SEQ ID NO: 17);

(xix) the heavy chain variable region comprises the amino acid sequence EVQLLESGGGLVQPGGSLRLS-CAASGFTFSQYVMHWVRQAPGK-GLEWVSSIWPSGGKT TYADSVKGRFTIS-RDNSKNTLYLQMNSLRAEDTAVYYCTRQRYR-GPKYYYYMDVWGK GTTVTVSS (SEQ ID NO: 18);

(xx) the heavy chain variable region comprises the amino acid sequence EVQLLESGGGLVQPGGSLRLS-CAASGFTFSQYVMHWVRQAPGK-GLEWVSSIWPSGGFT KYADSVKGRFTIS-RDNSKNTLYLQMNSLRAEDTAVYYCTRQRY-RGPKYYYYMDVWG KGTTVTVSS (SEQ ID NO: 19);

(xxi) the heavy chain variable region comprises the amino acid sequence EVQLLESGGGLVQPGGSLRLS-CAASGFTFSFYNMHWVRQAPGK-GLEWVSSIYPSGGVT RYADSVKGRFTIS-RDNSKNTLYLQMNSLRAEDTAVYYCTRQRY-RGPKYYYYMDVWG KGTTVTVSS (SEQ ID NO: 20);

(xxii) the heavy chain variable region comprises the amino acid sequence EVQLLESGG-GLVQPGGSLRLS-CAASGFTFSWYVMHWVRQAPGK-GLEWVSSIYPSGGKT SYADSVKGRFTISRDNSKNTLYLQMNSLRAED-TAVYYCTRQRYRGPKYYYYMDVWGK GTTVTVSS (SEQ ID NO: 21);

(xxiii) the heavy chain variable region comprises the amino acid sequence EVQLLESGG-GLVQPGGSLRLSCAASGFTFSPY-IMHWVRQAPGKGLEWVSVIYPSGSKTN YADSVKGRFTISRDNSKNTLYLQMNSLRAED-

TAVYYCTRQRYRGPKYYYYMDVWGK GTTVTVSS (SEQ ID NO: 22);

(xxiv) the heavy chain variable region comprises the amino acid sequence EVQLLESGG-GLVQPGGSLRLS-CAASGFTFSRYTMRWVRQAPGK-GLEWVSSIWPSGGMT RYADSVKGRFTISRDNSKNTLYLQMNSLRAED-TAVYYCTRQRYRGPKYYYYMDVWG QGTTVTVSS (SEQ ID NO: 23);

(xxv) the heavy chain variable region comprises the amino acid sequence EVQLLESGG-GLVQPGGSLRLS-CAASGFTFSQYVMHWVRQAPGK-GLEWVSSIYPSGGLT RYADSVKGRFTISRDNSKNTLYLQMNSLRAED-TAVYYCTRQRYRGPKYYYYMDVWG QGTTVTVSS (SEQ ID NO: 24);

(xxvi) the heavy chain variable region comprises the amino acid sequence EVQLLESGG-GLVQPGGSLRLSCAASGFTFSWY-IMGWVRQAPGKGLEWVSYIYPSGGNT RYADSVKGRFTISRDNSKNTLYLQMNSLRAED-TAVYYCTRQRYRGPKYYYYMDVWG KGTTVTVSS (SEQ ID NO: 25);

(xxvii) the heavy chain variable region comprises the amino acid sequence EVQLLESGG-GLVQPGGSLRLS-CAASGFTFSRYVMHWVRQAPGK-GLEWVSSIWPSGGMT KYADSVKGRFTISRDNSKNTLYLQMNSLRAED-TAVYYCTRQRYRGPKYYYYMDVWG KGTTVTVSS (SEQ ID NO: 26);

(xxviii) the heavy chain variable region comprises the amino acid sequence EVQLLESGG-GLVQPGGSLRLSCAASGFTFSFY-IMGWVRQAPGKGLEWVSRIYPSGGATQ YADSVKGRFTISRDNSKNTLYLQMNSLRAED-TAVYYCTRQRYRGPKYYYYMDVWGK GTTVTVSS (SEQ ID NO: 27);

(xxix) the heavy chain variable region comprises the amino acid sequence EVQLLESGG-GLVQPGGSLRLS-CAASGFTFSFYVMGWVRQAPGK-GLEWVSRIYPSGGLT QYADSVKGRFTISRDNSKNTLYLQMNSLRAED-TAVYYCTRQRYRGPKYYYYMDVWG KGTTVTVSS (SEQ ID NO: 28);

(xxx) the heavy chain variable region comprises the amino acid sequence EVQLLESGG-GLVQPGGSLRLS-CAASGFTFSFYSMHWVRQAPGK-GLEWVSRIYPSGGITS YADSVKGRFTISRDNSKNTLYLQMNSLRAED-TAVYYCTRQRYRGPKYYYYMDVWGK GTTVTVSS (SEQ ID NO: 29);

(xxxi) the heavy chain variable region comprises the amino acid sequence EVQLLESGG-GLVQPGGSLRLSCAASGFTFSMY-IMHWVRQAPGKGLEWVSSIYPSGGMT KYADSVKGRFTISRDNSKNTLYLQMNSLRAED-TAVYYCTRQRYRGPKYYYYMDVWG KGTTVTVSS (SEQ ID NO: 30);

(xxxii) the heavy chain variable region comprises the amino acid sequence EVQLLESGG-GLVQPGGSLRLS-CAASGFTFSMYVMHWVRQAPGK-GLEWVSSIYPSGGLT KYADSVKGRFTISRDNSKNTLYLQMNSLRAED-TAVYYCTRQRYRGPKYYYYMDVWG KGTTVTVSS (SEQ ID NO: 31);

(xxxiii) the heavy chain variable region comprises the amino acid sequence EVQLLESGG-GLVQPGGSLRLS-CAASGFTFSQYVMHWVRQAPGK-GLEWVSRIYPSGGLT NYADSVKGRFTISRDNSKNTLYLQMNSLRAED-TAVYYCTRQRYRGPKYYYYMDVWG KGTTVTVSS (SEQ ID NO: 32);

(xxxiv) the heavy chain variable region comprises the amino acid sequence EVQLLESGG-GLVQPGGSLRLS-CAASGFTFSWYVMQWVRQAPGK-GLEWVSSIYPSGGMT KYADSVKGRFTISRDNSKNTLYLQMNSLRAED-TAVYYCTRQRYRGPKYYYYMDVWG KGTTVTVSS (SEQ ID NO: 33);

(xxxv) the heavy chain variable region comprises the amino acid sequence EVQLLESGG-GLVQPGGSLRLSCAASGFTFSWY-IMGWVRQAPGKGLEWVSRIYPSGGST HYADSVKGRFTISRDNSKNTLYLQMNSLRAED-TAVYYCTRQRYRGPRYYYYIDAWGQ GTTVTVSS (SEQ ID NO: 34);

(xxxvi) the heavy chain variable region comprises the amino acid sequence EVQLLESGG-GLVQPGGSLRLS-CAASGFTFSQYTMVWVRQAPGK-GLEWVSRIYPSGGVT QYADSVKGRFTISRDNSKNTLYLQMNSLRAED-TAVYYCTRQRYRGPKYYYYMDVWG KGTTVTVSS (SEQ ID NO: 35);

(xxxvii) the heavy chain variable region comprises the amino acid sequence EVQLLESGG-GLVQPGGSLRLS-CAASGFTFSWYVMYWVRQAPGK-GLEWVSRIYPSGGIT HYADSVKGRFTISRDNSKNTLYLQMNSLRAED-TAVYYCTRQRYRGPKYYYYMDVWG KGTTVTVSS (SEQ ID NO: 36);

(xxxviii) the heavy chain variable region comprises the amino acid sequence EVQLLESGG-GLVQPGGSLRLS-CAASGFTFSFYVMLWVRQAPGK-GLEWVSSIWPSGGVT KYADSVKGRFTISRDNSKNTLYLQMNSLRAED-TAVYYCTRQRYRGPKYYYYMDVWG KGTTVTVSS (SEQ ID NO: 37);

(xxxix) the heavy chain variable region comprises the amino acid sequence EVQLLESGG-GLVQPGGSLRLS-CAASGFTFSWYVMQWVRQAPGK-GLEWVSYIYPSGGHT KYADSVKGRFTISRDNSKNTLYLQMNSLRAED-TAVYYCTRQRYRGPKYYYYMDVWG KGTTVTVSS (SEQ ID NO: 38); or (xxxx) the heavy chain variable region comprises the amino acid sequence EVQLLESGG-GLVQPGGSLRLS-CAASGFTFSRYSMNWVRQAPGK-GLEWVSGIYPSGGKT KYADSVKGRFTISRDNSKNTLYLQMNSLRAED-TAVYYCTRQRYRGPKYYYYMDVWG KGTTVTVSS (SEQ ID NO: 39); and and the light chain variable region comprises the amino acid sequence DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPWTFGQGTKVEIK (SEQ ID NO: 126) or the amino acid sequence DIQMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPWTFGQGTKVEIK (SEQ ID NO: 40).

11. A pharmaceutical composition, comprising
(a) the antibody of claim 1; and
(b) a pharmaceutically acceptable carrier.

12. An isolated nucleic acid or a set of nucleic acids, which collectively encode the antibody of claim 1.

13. A vector or vector set, comprising the nucleic acid or the set of nucleic acids of claim 12.

14. A host cell or host cell set, comprising the vector or vector set of claim 13.

15. A method of producing an antibody that binds to Factor XIIa (FXIIa), comprising:
culturing the cell or cell set of claim 14 in a culture medium; and
collecting the cultured cells or the culture medium for isolation of the antibody.

\* \* \* \* \*

UNITED STATES PATENT AND TRADEMARK OFFICE
CERTIFICATE OF CORRECTION

| | | |
|---|---|---|
| PATENT NO. | : 10,913,802 B2 | Page 1 of 1 |
| APPLICATION NO. | : 15/746048 | |
| DATED | : February 9, 2021 | |
| INVENTOR(S) | : Mason et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 103 days.

Signed and Sealed this
Seventeenth Day of June, 2025

Coke Morgan Stewart
*Acting Director of the United States Patent and Trademark Office*